United States Patent [19]

Shiokawa et al.

[11] Patent Number: 4,831,041
[45] Date of Patent: May 16, 1989

[54] IMIDAZOPYRIDINE COMPOUNDS AND PROCESSES FOR PREPARATION THEREOF

[75] Inventors: Youichi Shiokawa, Ibaraki; Masanobu Nagano, Kawanishi; Hiromichi Itani, Osaka, all of Japan

[73] Assignee: Fujisawa Pharmaceutical Co., Ltd., Osaka, Japan

[21] Appl. No.: 119,577

[22] Filed: Nov. 12, 1987

[30] Foreign Application Priority Data

Nov. 26, 1986 [GB] United Kingdom ................ 8628262
Oct. 6, 1987 [GB] United Kingdom ................ 8723439

[51] Int. Cl.$^4$ .................... A61K 31/44; C07D 471/04
[52] U.S. Cl. .................................... 514/300; 546/121
[58] Field of Search ......................... 546/121; 514/300

[56] References Cited

U.S. PATENT DOCUMENTS 4,450,164 5/1984 Bristol et al. ..................... 546/121
4,725,601 2/1988 Ueda et al. ......................... 546/121

FOREIGN PATENT DOCUMENTS 33094 8/1981 European Pat. Off. .
0204285 12/1986 European Pat. Off. .
0228006 7/1987 European Pat. Off. .

OTHER PUBLICATIONS

Yale, J. Medicinal and Pharmaceutical Chem., vol. 1 (2), p. 121-133 (1959).

Primary Examiner—Mary C. Lee
Assistant Examiner—Bernard I. Dentz
Attorney, Agent, or Firm—Oblon, Fisher, Spivak, McClelland & Maier

[57] ABSTRACT

The invention relates to an imidazopyridine compound of the formula:

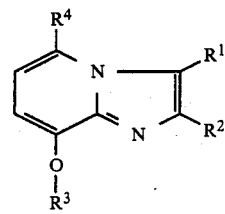

wherein
$R^1$ is lower alkynyl, lower alkynyloxy(lower)alkyl or N,N-di(lower)alkylamino(lower)alkynyl,
$R^2$ is lower alkyl,
$R^3$ is mono (or di or tri)-phenyl(lower)alkyl substituted by one or more substituent(s) selected from cyano, carbamoyl, mono (or di or tri(phenyl(lower)alkylamino, acylamino, carboxy, esterified carboxy, hydroxy, hydroxy(lower)alkyl, acyloxy(lower)alkyl, acyloxy, mono (or di or tri)phenyl(lower)alkoxy, lower alkoxy(lower)alkoxy, tetrahydropyranyloxy, and acylamino(lower)alkyl or mono (or di or tri) phenyl(lower)alkyl substituted by lower alkyl and one additional substituent selected from hydroxy(lower)alkyl, amino, N-lower alkyl-N-acylamino, mono (or di or tri)phenyl(lower)alkylamino, acylamino and lower alkylamino, and
$R^4$ is hydrogen or lower alkyl, and a pharmaceutically acceptable salt thereof, useful in the treatment of ulcers.

13 Claims, No Drawings

IMIDAZOPYRIDINE COMPOUNDS AND PROCESSES FOR PREPARATION THEREOF

The present invention relates to novel imidazopyridine compounds and pharmaceutically acceptable salt threof. More particularly, it relates to novel imidazopyridine compounds and pharmaceutically acceptable salts thereof which have antiulcerative activity, to processes for preparation thereof, to pharmaceutical composition comprising the same, and to method of using the same therapeutically in the treatment of ulcer in human being or animals.

Accordingly, one object of the present invention is to provide novel imidazopyridine compounds and pharmaceutically acceptable salt thereof, which are useful as a medicine for ulcer.

Another object of the present invention is to provide processes for preparation of said imidazopyridine compounds and pharmaceutically acceptable salts thereof.

A further object of the present invention is to provide pharmaceutical composition comprising, as an active ingredient, said imidazopyridine compounds or its pharmaceutically acceptable salt.

Still further object of the present invention is to provide method of using said imidazopyridine compounds or its pharmaceutically acceptable salt in the treatment of ulcer in human being or animal.

The imidazopyridine compounds of the present invention are novel and can be represented by the formula (I):

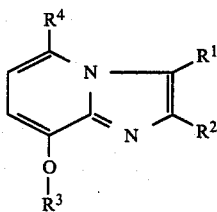

(I)

wherein
$R^1$ is lower alkynyl, lower alkynyloxy(lower)alkyl or N,N-di(lower)alkylamino(lower)alkynyl,
$R^2$ is lower alkyl,
$R^3$ is ar(lower)alkyl substituted by one or more substituent(s) selected from cyano, trihalo(lower)alkyl, carbamoyl, protected amino, carboxy, protected carboxy, hydroxy, hydroxy(lower)alkyl, protected hydroxy(lower)alkyl, protected hydroxy and protected amino(lower)alkyl, or ar(lower)alkyl substituted by lower alkyl and one additional substituent selected from hydroxy(lower)alkyl, amino, N-lower alkyl-N-protected amino, protected amino and lower alkylamino, and
$R^4$ is hydrogen or lower alkyl.

According to the present invention, the object compounds (I) can be prepared by the following processes.

Process 1

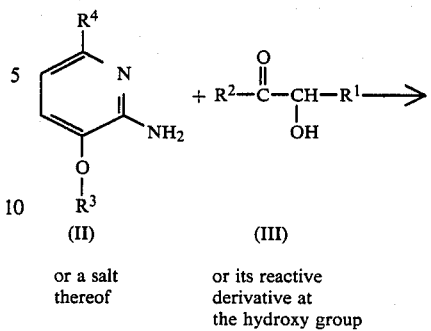

(II)     (III)

or a salt thereof     or its reactive derivative at the hydroxy group

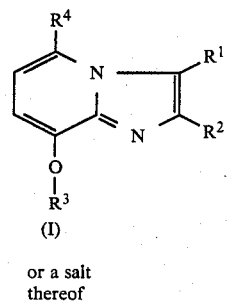

(I)

or a salt thereof

Process 2

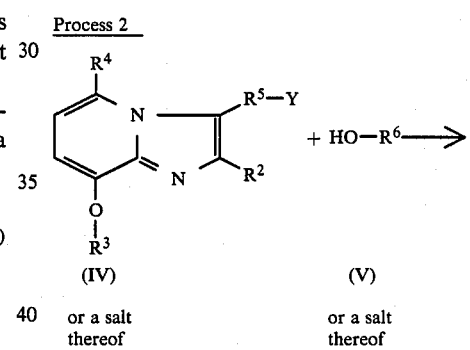

(IV)     (V)

or a salt thereof     or a salt thereof

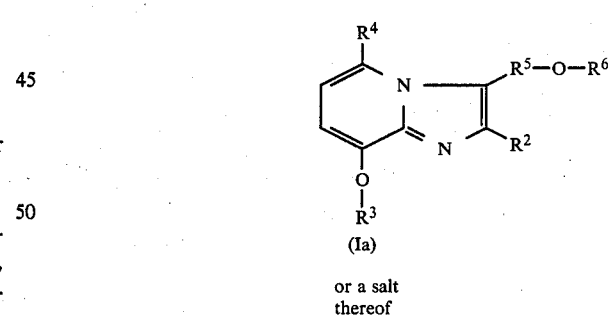

(Ia)

or a salt thereof

Process 3

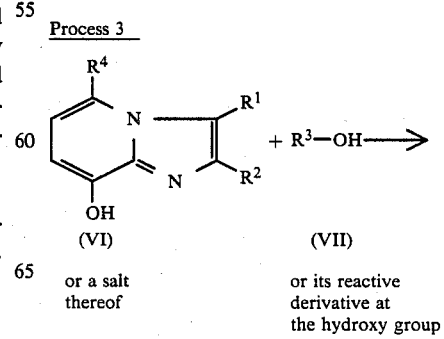

(VI)     (VII)

or a salt thereof     or its reactive derivative at the hydroxy group

-continued
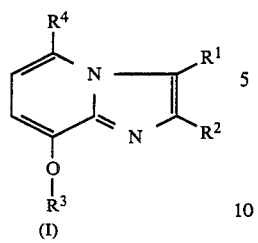
(I)
or a salt thereof
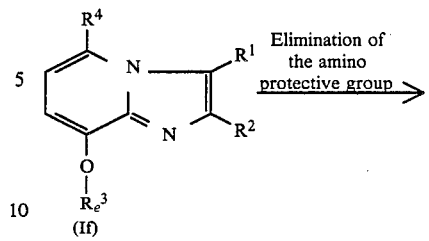
(If)
or a salt thereof
Process 4
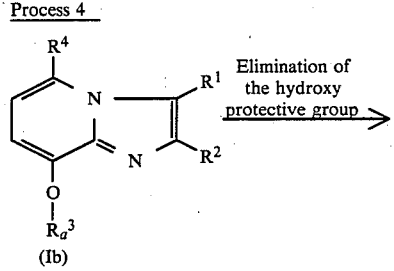
(Ib)
or a salt thereof
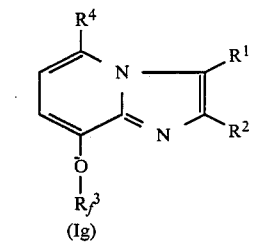
(Ig)
or a salt thereof
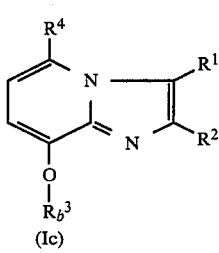
(Ic)
or a salt thereof
Process 7
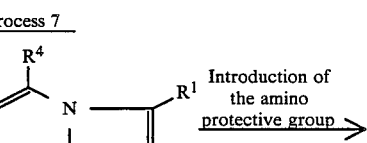
(Ig)
or its reactive derivative at the amino group or a salt thereof
Process 5
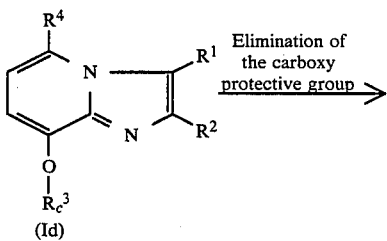
(Id)
or a salt thereof
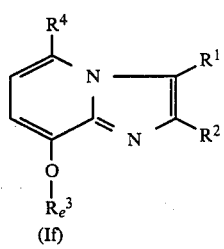
(If)
or a salt thereof
Process 8
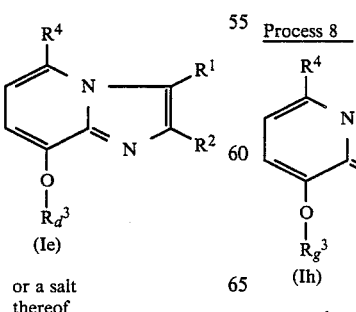
(Ie)
or a salt thereof
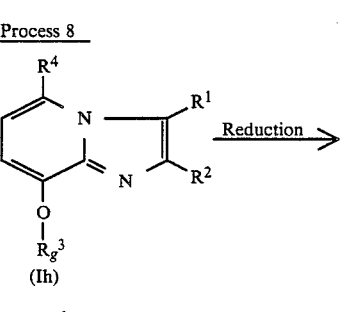
(Ih)
or a salt thereof
Process 6

-continued (Ii) or a salt thereof

Process 9

(Ij) or a salt thereof → Elimination of the amino protective group →

(Ik) or a salt thereof

Process 10

(II) or a salt thereof + $(R^7)_2NH$ (VIII) in the presence of formaldehyde →

(Im) or a salt thereof wherein
$R^1$, $R^2$, $R^3$ and $R^4$ are each
$R_b^1$ is N,N-di(lower)alkylamino(lower)alkynyl, $R_a^3$ is ar(lower)alkyl substituted by protected hydroxy(lower)alkyl,
$R_b^3$ is ar(lower)alkyl substituted by hydroxy-(lower)alkyl,
$R_c^3$ is ar(lower)alkyl substituted by protected carboxy,
$R_d^3$ is ar(lower)alkyl substituted by carboxy,
$R_e^3$ is ar(lower)alkyl substituted by lower alkyl and one additional substituent selected from protected amino and N-lower alkyl-N-protected amino,
$R_f^3$ is ar(lower)alkyl substituted by lower alkyl and one additional substituent selected from amino and lower alkylamino,
$R_g^3$ is ar(lower)alkyl substituted by lower alkyl and lower alkanoylcarbonylamino,
$R_h^3$ is ar(lower)alkyl substituted by lower alkyl and α-hydroxy(lower)alkanoylamino,
$R_i^3$ is ar(lower)alkyl substituted by lower alkyl and one additional substituent selected from protected amino(lower)alkanoylamino and protected thioureido,
$R_j^3$ is ar(lower)alkyl substituted by lower alkyl and one additional substituent selected from amino(lower)alkanoylamino and thioureido,
$R_6^5$ is lower alkylene,
$R^6$ is lower alkynyl,
$R^7$ is lower alkyl, and
Y is a leaving group.

As to the starting compounds (II), (III), (IV), (VI) and (VII), some of them are novel and can be prepared by the procedures disclosed in the following Preparations 1 to 41.

Suitable salts of the object compounds (I) are conventional non-toxic, pharmaceutically acceptable salts and may include a salt with a base or an acid addition salt such as a salt with an inorganic base, for example, an alkali metal salt (e.g. sodium salt, potassium salt, cesium salt, etc.), an alkaline earth metal salt (e.g. calcium salt, megnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), etc.: an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like.

In the above and subsequent descriptions of the present specification, suitable examples and illustrations of the various definitions which the present invention include within the scope thereof are explained in detail as follows.

The term "lower" is intended to mean 1 to 6, preferably 1 to 4 carbon atom(s), unless otherwise indicated.

Suitable "lower alkynyl" group and "lower alkynyl" moieties may be the ones having 2 to 6 carbon atoms and may include ethynyl, 1(or 2)-propynyl, 1(or 2 or 3)-butynyl, 1(or 2 or 3 or 4)-pentynyl, 1(or 2 or 3 or 4 or 5)-hexynyl, and the like.

Suitable "lower alkyl" group and "lower alkyl" moieties may be the ones having 1 to 6 carbon atom(s) and may include methyl, ethyl, propyl, isopropyl, n-butyl, t-butyl, pentyl, hexyl and the like.

Suitable "ar(lower)alkyl" may include mono(or di or tri)-phenyl(lower)alkyl such as benzyl, benzhydryl, trityl, phenethyl or the like.

Suitable "protected amino" group and "protected amino" moieties may include an amino group substituted by a conventional amino-protective group which is used in peptide chemistry, for example, ar(lower)alkyl as mentioned above and acyl as mentioned below.

Suitable "acyl" may include carbamoyl, thiocarbamoyl, sulfamoyl, an aliphatic acyl, an aromatic acyl, a heterocyclic acyl and an aliphatic acyl substituted with aromatic or heterocyclic group(s) derived from carbamic, sulfonic, carboxylic or carbonic acids and their thio acids.

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.,), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, isopropoxycarbonyl, butoxycrbonyl, tert-butoxycarbonyl, etc.), lower alkenoyl (e.g. acryloyl, methacryloyl, crotonoyl, etc.), ($C_3$–$C_7$)-cycloalkanecarbonyl (e.g. cyclohexanecarbonyl, etc.), lower alkoxalyl (e.g. methoxalyl, ethoxalyl, etc.), lower alkanoylcarbonyl (e.g. pyruvoyl, etc.), and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclic carbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include phenyl(lower)alkanoyl (e.g. phenylacetyl, phenylpropionyl, phenylhexanoyl, etc.), phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with suitable substituent(s) such as hydroxy, amino, carboxy, lower alkyl (e.g. methyl, ethyl, propyl, isopropyl, butyl, pentyl, hexyl, etc.), halogen (e.g. chloride, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro, protected amino in which the amino protective moiety may be the same as those herein, aryl (e.g. phenyl, etc.), aroyl(e.g. benzoyl, etc.), aryloxy (e.g., benzyloxy, tolyloxy, etc.), protected hydroxy such as acyloxy, for example, lower alkanoyloxy (e.g. formyloxy, acetyloxy, propionyloxy, butyryloxy, isobutyryloxy, valeryloxy, isovaleryloxy, pivaloyloxy, hexanoyloxy, etc.), lower alkylamino (e.g. methylamino, ethylamino, etc.), and the like, and the preferable acyl having such substituent(s) may be mono (or di or tri) halo(lower)alkanoyl (e.g.,chloroacetyl, bromoacetyl, dichloroacetyl, trifluoroacetyl, etc.), amino(lower)alkanoyl (e.g., glycyl, aminopropionyl, diaminobutyryl, etc.), phenyl(lower)alkoxycarbonylamino(lower)alkanoyl (e.g., benzyloxycarbonylglycyl, etc.), lower alkanoyloxy(lower)alkanoyl (e.g., acetoxyacetyl, etc.), lower alkylcarbamoyl (e.g. methylcarbamoyl, ethylcarbamoyl, etc.), lower alkoxycarbonylamino(lower)alkanoyl (e.g. t-butoxycarbonylaminoacetyl, etc.), phenyl(lower)alkoxycarbonylcarbamoyl (e.g., benzyloxycarbonylcarbamoyl) phenyl(lower)alkoxy(lower)alkanoyl (e.g. benzyloxyacetyl, benzyloxypropionyl, etc.), carboxy(lower)alkanoyl (e.g., carboxyacetyl, carboxypropionyl, etc.), hydroxy(lower)alkanoyl (e.g. glycoloyl, hydroxypropionyl, hydroxybutyryl etc.), aroylthiocarbamoyl (e.g., benzoylthiocarbamoyl, etc.), etc.

Suitable "protected carboxy" may include an esterified carboxy group.

Suitable examples of the ester moiety of an "esterified carboxy" may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(ior 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.) lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phtahlidylidene(lower)alkyl ester, or (5-lower alkyl-2-oxo-1,3-dioxol-4-yl)(lower)alkyl ester (e.g. (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

Preferable examples of the esterified carboxy as mentioned above may include lower alkoxycarbonyl (e.g. methoxycarbonyl, ethoxycarbonyl, propoxycarbonyl, isopropoxycarbonyl butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.).

Suitable "hydroxy-protective group" in the term "protected hydroxy" may include aforesaid acyl, ar(lower)alkyl (e.g. benzyl, trityl, etc.), lower alkoxy(lower)alkyl (e.g. methoxymethyl, 1-methyl-1-methoxyethyl, methoxypropyl, etc.), tetrahydropyranyl, and the like.

Suitable "N-lower alkyl-N-protected amino" may include N-lower alkyl-N-acylamino, in which the acyl moiety may be the same as the above, such as N-lower alkyl-N-lower alkoxycarbonylamino (e.g. N-methyl-N-methoxyarbonylamino, N-methyl-N-tert-butoxycarbonylamino, etc.), N-lower alkyl-N-lower alkanesulfonylamino (e.g. N-methyl-N-mesylamino, etc.), N-lower alkyl-N-carbamoylamino (e.g. N-methyl-N-carbamoylamino, etc.), N-lower alkyl-N-carbamoylamino substituted by lower alkyl (e.g. 1,3-dimethylureido, etc.), N-lower alkyl-N-lower alkanoylamino (e.g. N-methyl-N-acetylamino, etc.) and the like.

Suitable "lower alkynyloxy(lower)alkyl" may be 2-propynyloxymethyl, and the like.

Suitable "N,N-di(lower)alkylamino(lower)alkynyl" may be 4-N,N-dimethylamino-2-butynyl and the like.

Suitable "trihalo(lower)alkyl" may include trifluoro(lower)alkyl (e.g. trifluoromethyl, trifluoroethyl, etc.), and the like.

Suitable "hydroxy(lower)alkyl" may include hydroxymethyl, hydroxyethyl, hydroxypropyl and the like.

Suitable "protected hydroxy(lower)alkyl" may include acyloxy(lower)alkyl, in which the acyl moiety may be the same as the above, such as lower alkanoyloxy(lower)alkyl (e.g. formyloxymethyl, acetyloxymethyl, propionyloxymethyl, butyryloxymethyl, valeryloxymethyl, etc.), and the like.

Suitable "protected amino(lower)alkyl" may include acylamino(lower)alkyl, in which the acyl moiety may be the same as the above, such as lower alkoxycarbonylamino(lower)alkyl (e.g. methoxycarbonylaminomethyl, ethoxycarbonylaminomethyl, etc.), and the like.

Suitable "lower alkylamino" may include methylamino, ethylamino, propylamino, isopropylamino, butylamino, and the like.

Suitable "ar(lower)alkyl substituted by protected hydroxy(lower)alkyl" may include ar(lower)alkyl substituted by acyloxy(lower)alkyl such as lower alkanoyloxy(lower) alkylbenzyl (e.g. formyloxymethylbenzyl, acetyloxymethylbenzyl, propionyloxymethylbenzyl, butyryloxymethylbenzyl, valeryloxymethylbenzyl, etc.), and the like.

Suitable "ar(lower)alkyl substituted by hydroxy(lower)alkyl" may include hydroxy(lower)alkylbenzyl (e.g. hydroxymethylbenzyl, hydroxyethylbenzyl, hydroxypropylbenzyl, etc.), and the like.

Suitable "ar(lower)alkyl substituted by protected carboxy" may include ar(lower)alkyl substituted by esterified carboxy, in which the esterified carboxy may be the same as the above, such as lower alkoxycarbonylbenzyl (e.g. methoxycarbonylbenzyl, ethoxycarbonylbenzyl, etc.), and the like.

Suitable "ar(lower)alkyl substituted by carboxy" may include carboxybenzyl, and the like.

Suitable "ar(lower)alkyl substituted by lower alkyl and protected amino" may include ar(lower)alkyl substituted by lower alkyl and acylamino, in which the acyl moiety may be the same as the above, such as benzyl substituted by methyl and ureido (e.g. 2-methyl-6-ureidobenzyl, etc.), benzyl substituted by methyl and thioureido (e.g. b 2-methyl-6-thioureidobenzyl, etc.), benzyl substituted by methyl and lower alkanoylamino (e.g. 6-formamido-2-methylbenzyl, 3-acetamido-2-methylbenzyl, 5-acetamido-2-methylbenzyl, 2-acetamido-6-methylbenzyl, 2-methyl-6propionamidobenzyl, 2-acetamido-4-methylbenzyl, 2-butyramido-6-methylbenzyl, etc.), benzyl substituted by methyl and lower alkanesulfonylamino (e.g. 2-methanesulfonylamino-6-methylbenzyl, etc.), benzyl substituted by methyl and lower alkoxycarbonylamino (e.g. 2-methoxycarbonylamino-6-methylbenzyl, 2-ethoxycarbonylamino-6-methylbenzyl, 2-methyl-6-i-propoxycarbonylaminobenzyl, 2-t-butoxycarbonylamino-6-methylbenzyl, etc.), benzyl substituted by methyl and heterocyclic carbonylamino (e.g. 2-isonicotinamido-6methylbenzyl, etc.), benzyl substituted by methyl and acylamino substituted with suitable substituent (e.g. 6-methyl-2-(3-methylureido)benzyl, 2-(3-benzoylthioureido)-6-methylbenzyl, 2-t-butoxycarbonyl-aminoacetamido-6-methylbenzyl, 2-benzyloxycarbonylamino-6-methylbenzyl, 2-(N-methoxycarbonyl-N-methylamino-6-methylbenzyl, 2-hydroxyacetamido-6-methylbenzyl, 2-acetoxyacetamido-6-methylbenzyl, 2-methyl-6-pyruvamidobenzyl, 2-methoxalylamino-6-methylbenzyl, 2-methyl-6-sulfamidobenzyl, 2-lactamido-6-methylbenzyl, 2-aminoacetamido-6-methylbenzyl, etc.), and the like.

Suitable "ar(lower)alkyl substituted by lower alkyl and amino" may include benzyl substituted by methyl and amino (e.g. 2-amino-6-methylbenzyl, etc.) and the like.

Suitable "ar(lower)alkyl substituted by lower alkyl and lower alkanoylcarbonylamino" may include benzyl substituted by methyl and lower alkanoylcarbonylamino (e.g. 2-methyl-6-pyruvamidobenzyl, etc.), and the like.

Suitable "ar(lower)alkyl substituted by lower alkyl and α-hydroxy(lower)alkanoylamino" may include benzyl substituted by methyl and α-hydroxy(lower)alkanoylamino (e.g. 2-lactamido-6-methylbenzyl, etc.), and the like.

Suitable "ar(lower)alkyl substituted by lower alkyl and protected amino(lower)alkanoylamino" may include ar(lower)alkyl substituted by lower alkyl and acylamino(lower)alkanoylamino, in which the acyl moiety may be the same as the above, such as benzyl substituted by methyl and acylamino(lower)alkanoylamino (e.g. 2-t-butoxycarbonylaminoacetamido-6-methylbenzyl, etc.), and the like.

Suitable "ar(lower)alkyl substituted by lower alkyl and amino(lower)alkanoylamino" may include benzyl substituted by methyl and amino(lower)alkanoylamino (e.g. 2-aminoacetamido-6-methylbenzyl, etc.), and the like.

Suitable "ar(lower)alkyl substituted by lower alkyl and protected thioureido" may include ar(lower)alkyl substituted by lower alkyl and acylthioureido, in which the acyl moiety may be the same as those given above, such as benzyl substituted by methyl and 3-aroylthioureido (e.g. 2-(3-benzoylthioureido)-6methylbenzyl, etc.), and the like.

Suitable "ar(lower)alkyl substituted by lower alkyl and thioureido" may include benzyl substituted by methyl and thioureido (e.g. 2-methyl-6-thioureidobenzyl, etc.) and the like.

Suitable "ar(lower)alkyl substituted by lower alkyl and N-lower alkyl-N-protected amino" may include ar(lower)alkyl substituted by lower alkyl and N-lower alkyl-N-acylamino, in which the acyl moiety may be the same as the above, such as benzyl substituted by methyl and N-methyl-N-lower alkoxycarbonylamino (e.g. 2-methyl-6-N-methyl-N-methoxycarbonylamino)benzyl, 2-methyl-6-N-methyl-N-tert-butoxycarbonylamino)-benzyl, etc.), benzyl substituted by methyl and N-methyl-N-lower alkaneamino (e.g. 2-methyl-6-(N-methyl-N-mesylamino)benzyl, etc.), benzyl substituted by methyl and N-methyl-N-carbamoylamino (e.g. 2-methyl-6-(N- methyl-N-carbamoylamino)benzyl, etc.), benzyl substituted by methyl and 1,3-di(lower)alkylureido (e.g. 2-methyl-6-(1,3-dimethylureido)benzyl, etc.), benzyl substituted by methyl and N-methyl-N-lower alkanoylamino (e.g. 2-methyl-6-(N-methyl-N-acetylamino)benzyl, etc.) and the like.

Suitable "ar(lower)alkyl substituted by lower alkyl and lower alkylamino" may include benzyl substituted by methyl and lower alkylamino (e.g. 2-methyl-6-methylaminobenzyl, etc.) and the like.

Suitable "lower alkylene" may include methylene, ethylene, trimethylene, tetramethylene, pentamethylene, hexamethylene and the like.

Suitable "protective" moiety in the term "protected thioureido" may include acyl such as carbamoyl, sulfamoyl, an aliphatic acyl, an aromatic acyl, a heterocyclic acyl and an aliphatic acyl substituted with aromatic or heterocyclic group(s) as mentioned above.

Suitable "a leaving group" may include an acid residue such as halogen (e.g. fluorine, chlorine, bromine, iodine), acyloxy (e.g. acetoxy, tosyloxy, mesyloxy, etc.), and the like, a group of the formula:

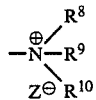

wherein
$R^8$, $R^9$ and are each lower alkyl as mentioned above, and
Z is an acid residue as mentioned above, and the like.

Preferred embodiments of the object compounds (I) are as follows.

Preferred embodiment of $R^1$ is lower alkynyl, lower alkynyloxy(lower)alkyl or N,N-di(lower)alkylamino(lower)alkynyl.

Preferred embodiment of $R^2$ is lower alkyl.

Preferred embodiment of $R^3$ is benzyl substituted with cyano, trihalo(lower)alkyl, carbamoyl, lower alkanoylamino, ureido, lower alkoxycarbonylamino, carboxy, lower alkoxycarbonyl, hydroxy, hydroxy(lower)alkyl, lower alkanoyloxy(lower)alkyl, or lower alkoxy(lower)alkoxy, or lower alkoxycarbonylamino(lower)alkyl; or
benzyl substituted with lower alkyl and one additional substituent selected from hydroxy, amino, lower alkanoylamino, lower alkanesulfonylamino, lower alkoxycarbonylamino, heterocyclic carbonylamino, ureido, ureido having lower alkyl, lower alkoxycarbonylamino(lower)alkanoylamino, phenyl(lower)alkoxycarbonylamino N-lower alkoxycarbonyl-N-lower alkylamino, hydroxy(lower)alkanoylamino, lower alkanoyloxy(lower)alkanoylamino, lower alkanoylcarbonylamino, lower alkoxycarbonylcarbonylamino, sulfamido, lower alkanoylamino having hydroxy, amino(lower)alkanoylamino, N-lower alkanoyl-N-lower alkylamino, N-carbamoyl-N-lower alkylamino, N-lower alkylaminocarbonyl-N-lower alkylamino, N-lower alkylsulfonyl-N-lower alkylamino, thioureido, protected thioureido, lower alkylamino.

Preferred embodiment of $R^4$ is hydrogen or lower alkyl.

The processes for preparing the object compounds of the present invention are explained in detail in the following.

PROCESS 1

The object compound (I) or a salt thereof can be prepared by reacting the compound (II) or a salt thereof with the compound (III) or its reactive derivative at the hydroxy group.

Suitable salts of the compound (II) can be referred to the acid addition salt as exemplified for the compound (I), and suitable reactive derivative of the compound (III) may be one, in which the hydroxy group is replaced by an acid residue such as halogen (e.g. halogen (e.g. fluorine, chlorine, bromine, iodine), acyloxy (e.g. acetoxy, tosyloxy, mesyloxy, etc.), and the like.

This reaction is usually carried out in a solvent such as alcohol [e.g. methanol, ethanol, etc.], benzene, N,N-dimethylformamide, tetrahydrofuran, diethyl ethyl or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. trimethylamine, triethylamine, etc.], pyridine or its derivative [e.g. picoline, lutidine, 4-dimethylaminopyridine, etc.], or the like. In case that the base to be used is liquid, it can also be used as a solvent.

In case that the compound (III) is used in a form of free hydroxy, the reaction can be carried out in the presence of a condensing agent such as N,N-dicyclohexylcarbodiimide; N-cyclohexyl-N'morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; 1,1'-(carbonyldioxy)dibenzotriazole, 1, 1'-dibenzotriazolyloxallate trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction temperature is not critical, and the reaction can be carried out under cooling, at ambient temperature or under warming or heating.

PROCESS 2

The object compound (Ia) or a salt thereof can be prepared by reacting the compound (IV) or a salt thereof with the compound (V) or a salt thereof.

Suitable salts of the compounds (IV) and (Ia) can be referred to the ones as exemplified for the object compound (I).

Suitable salts of the compound (V) are salts with a base such as an alkali metal salt (e.g. sodium salt, potassium salt, lithium salt, etc.), or the like.

This reaction is usually carried out in the presence of a base such as alkali metal hydride (e.g. sodium hydride, potassium hydride, lithium hydride, etc.), alkali metal alkoxide (e.g. potassium t-butoxide, etc.), an alkali metal (e.g. sodium, potassium, lithium, etc.) or the like.

This reaction is usually carried out in a solvent such as alcohol [e.g. methanol, ethanol, etc.], dimethyl sulfoxide, benzene, N,N-dimethylformamide, tetrahydrofuran, diethyl ether or any other solvent which does not adversely affect the reaction.

In case that the compound (V) or a salt thereof to be used is liquid, it can also be used as a solvent.

The reaction temperature is not critical, and the reaction can be carried out under cooling, at ambient temperature or under warming or heating.

PROCESS 3

The object compound (I) or a salt thereof can be prepared by reacting the compound (VI) or a salt thereof with the compound (VII) or its reactive derivative at the hydroxy group.

Suitable salts of the compound (VI) can be referred to the salt as exemplified for the compound (I) and suitable reactive derivative of the compound (VII) may be the same as those given for the compound (III) in Process 1.

This reaction is usually carried out in a solvent such as alcohol [e.g. methanol, ethanol, etc.], benzene, N,N-dimethylformamide, tetrahydrofuran, diethyl ether or any other solvent which does not adversely affect the reaction.

The reaction may be carried out in the presence of an inorganic or an organic base such as an alkali metal hydroxide [e.g. sodium hydroxide, potassium hydroxide, etc.], a- alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. trimethylamine, triethylamine, etc.], pyridine or its derivative [e.g. picoline, lutidine, 4-dimethylaminopyridine, etc.], or the like. In case that the base to be used is liquid, it can also be used as a solvent.

The reaction temperature is not critical, and the reaction can be carried out under cooling, at ambient temperature or under warming or heating.

PROCESS 4

The object compound (Ic) or a salt thereof can be prepared by subjecting the compound (Ib) or a salt thereof to elimination reaction of the hydroxy protective group in $R_a{}^3$.

Suitable salts of the compounds (Ib) and (Ic) can be referred to the salt as exemplified for the compound (I).

Suitable method for this elimination reaction may include conventional one such as hydrolysis, reduction, or the like. The hydrolysis is preferably carried out in the presence of a base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-one, 1,4-diazabicyclo[2,2,2]octane, 1,5-diazabicyclo[5,4,0]undecene-5 or the like. The hydrolysis using a base is often carried out in water or a hydrophilic o-ganic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitably be selected in accordance with the kind of the hydroxy protective group and the elimination method.

PROCESS 5

The object compound (Ie) or a salt thereof can be prepared by subjecting the compound (Id) or a salt thereof to elimination reaction of the carboxy protective group in $R_c{}^3$.

Suitable salts of the compounds (Id) and (Ie) can be referred to the salts as exemplified for the compound (I).

The present reaction can be carried out in a similar manner to that of Process 4 as mentioned above, and therefore the reaction mode and reaction conditions can be referred to those of Process 4.

PROCESS 6

The object compound (Ig) or a salt thereof can be prepared by subjecting the compound (If) or a salt thereof to elimination reaction of the amino protective group in $R_e{}^3$.

Suitable salts of the compounds (If) and (Ig) can be referred to the salts as exemplified for the compound (I).

The present reaction can be carried out in a similar manner to that of Process 4 as mentioned above, and therefore the reaction mode and reaction conditions can be referred to those of Process 4.

PROCESS 7

The object compound (If) or a salt thereof can be prepared by subjecting the compound (Ig) or its reactive derivative at the amino group or a salt thereof to introduction reaction of the amino protective group.

Suitable reactive derivative at the amino group of the compound (Ig) may include Schiff's base type imino or its tautomeric enamine type isomer formed by the reaction of the compound (Ig) with a carbonyl compound such as aldehyde, ketone or the like; a silyl derivative formed by the reaction of the compound (Ig) with a silyl compound such as bis(trimethylsilyl)acetamide, mono(trimethylsilyl)acetamide or the like; a derivative formed by reaction of the compound (Ig) with phosphorus trichloride or phosgene, and the like.

Suitable introducing agent to be used in the present reaction may include conventional one and can be shown by the formula:

$$R^{11}-OH \qquad (IX)$$

(wherein $R^{11}$ is acyl as exemplified above) or its reactive derivative or a salt thereof.

Suitable salt of the compound (Ig) and (IX) may include an acid addition salt such as an organic acid salt (e.g. acetate, maleate, tartrate, methanesulfonate, benzenesulfonate, toluenesulfonate, etc.) or an inorganic acid salt (e.g. hydrochloride, hydrobromide, sulfate, phosphate, etc.); a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative of the compound (IX) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl $[(CH_3)_2N^+=CH-]$ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (IX) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

When the compound (IX) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine, diphenylketene-N-cyclohexylimine; ethoxyacetylene; 1-alkoxy-1-chloroethylene; trialkyl phosphite; ethyl polyphosphate; isopropyl polyphosphate phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of dimethylformamide with thionyl, chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

PROCESS 8

The object compound (Ii) or a salt thereof can be prepared by reducing a compound (Ih) or a salt thereof.

The reduction can be carried out in a conventional manner, namely, chemical reduction or catalytic reduction.

Suitable reducing agents to be used in chemical reduction are a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, etc.], borane, diborane, aluminum halide [e.g. aluminum chloride, etc.], phosphorus trihalide [e.g. phosphorus trichloride, phosphorus tribromide, etc.], ferrous oxalate, a combination of metal [e.g. tin, zinc, iron, etc.]or metallic compound [e.g. chromium chloride, chromium acetate, etc.]and an organic or inorganic acid [e.g. formic acid, acetic acid, propionic acid, trifluoroacetic acid, p-toluenesulfonic acid, hydrochloric acid, hydrobromic acid, etc.]or the like.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nikel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.]or the like.

The reaction of this process is usually carried out in a solvent such as water, alcohol [e.g. methanol, ethanol, propanol, etc.], acetic acid, diethyl ether, dioxane, tetrahydrofuran, methylene chloride, chloroform, N,N-dimethylformamide, dimethylsulfoxide, or any other organic solvent which does not adversely influence the reaction, or a mixture thereof.

The reaction is preferably carried out under somewhat milder conditions such as under cooling to warming.

PROCESS 9

The object compound (Ik) or a salt thereof can be prepared by subjecting the compound (Ij) or a salt thereof to elimination reaction of the amino protective group in $R_j{}^3$.

Suitable salts of the compound (Ij) and (Ik) can be referred to the salts as exemplified for the compound (I).

The present reaction can be carried out in a similar manner to that of Process 4 as mentioned above and therefore the reaction mode and reaction conditions can be referred to those of Process 4.

PROCESS 10

The object compound (Im) or a salt thereof can be prepared by reacting the compound (Il) or a salt thereof with the compund (VIII) in the presence of formaldehyde.

Suitable salts of the compound (Il) and (Im) can be referred to the salts as exemplified for the compound (I).

The present reaction is carried out by the method of so-called Mannich reaction.

The reaction is usually carried out in a solvent such as water, methylene chloride, N,N-dimethylformamide, an alcohol (e.g. methanol, ethanol, etc.), tetrahydrofuran, dioxane, diethyl ether, a mixture thereof or any other solvent which does not adversely influence the reaction. A liquid acid can be also used as the solvent.

The reaction may be carried out in the presence of a catalyst such as cuprous chloride.

The reaction temperature is not critical and the reaction is usually carried out under cooling to heating.

The object compounds (I) and their pharmaceutically acceptable salts of the present invention are novel and exhibit high inhibitory activity on ulcer.

In order to illustrate the usefulness of the object compound (I), the pharmacological data of the representative compound of the object compound (I) are shown in the following.

(A) Inhibition on ethanol ulcer

Test Method

Five male Sprague-Dawley rats, aged 7 weeks and weighing about 200 g, were used per group for the study on ethanol ulcer after the fast for 24 hours.

Test compound was suspended in 0.1% methylcellulose aqueous solution, and the suspension (5 ml/kg) was orally given to each rat.

The control group was given a vehicle, i.e. 0.1% methylcellulose aqueous solution (5 ml/kg), alone in the same way.

Absolute ethanol (5 ml/kg) was orally administered 30 minutes after dosing with test compound, and one hour later, the rats were sacrificed and their stomachs were removed. The area of ulcers of each rat was measured. The mean area (mm) in the medicated group was compared with that in the control group.

Test Compound (1) 8-(2-Methoxycarbonylamino-6-methylbenzyloxy)-2methyl-3-(2-propynyl)imidazo[1,2-a]pyridine Test Result
Inhibition % at the dose of 32 mg/kg:

| Test Compound | Inhibition % |
| --- | --- |
| (1) | 93.2 |

(B) Inhibition on Stress Ulcer

Test Method

Five Sprague-Dawley rats weighing about 200 g were used per group. Each animal was immobilized in a small cage and put in a water bath allowing to respire. The temperature of the water bath kept at 22° C. The test compound was administered orally just before the immobilization. Seven hours later, the animals were sacrificed and their stomachs were removed. The stomach was then fixed with 2% formalin. The area of ulcers was measured for each animal. The mean area (mm$^2$) in the medicated animals was compared with that in the control animals.

Test Compounds (1) 8-(2-Methoxycarbonylamino-6-methylbenzyloxy)-2-methyl-3-(2-propynyl)imidazo[1,2-a]pyridine
(2) 8-(2-Acetamido-6-methylbenzyloxy)-2-methyl-3-(2-propynyl)imidazo[1,2-a]pyridine
(3) 2-methyl-8-(2-methyl-6-ureidobenzyloxy)-3-(2propynyl)imidazo[1,2-a]pyridine
(4) 2-Methyl-8-(2-methyl-6-thioureidobenzyloxy)-3(2-propynyl)imidazo[1,2-a]pyridine Test Result Inhibition % at the dose of 32 mg/kg:

| Test Compound | Inhibition % |
| --- | --- |
| (1) | 100 |
| (2) | 100 |
| (3) | 100 |
| (4) | 100 |

As being apparent from the above test results, the object compound (I) of the present invention are useful as antiulcer medicines.

For therapeutic purpose, the compounds according to the present invention can be used in a form of pharmaceutical preparation containing said compound as an active ingredient, in admixture with a pharmaceitically acceptable carrier such as an organic or inorganic solid or liquid excipient suitable for oral or parenteral administration. The pharmaceutical preparations may be capsules, tablets, dragees, solution, suspension, emulsion, and the like. If desired, there may be included in the above preparations auxiliary substances, stabilizing agents, wetting or emulsifying agents, buffers and other commonly used additives.

While the dosage of the compounds will vary depending upon the age and condition of the patient, an average single dose of about 5 mg, 10 mg, 50 mg, 100 mg, 250 mg, 500 mg, and 1000 mg of the compounds according to the present invention may be effective for treating ulcer. In general, amounts between 1 mg/body and about 2,000 mg/body or even more may be administered per day.

The following preparations and examples are given for the purpose of illustrating the present invention.

Preparation 1

2-Acetoxymethylbenzyl alcohol (0.91 g) was obtained by reacting 1,2-bis(hydroxymethyl)benzene (1.38 g) with acetic anhydride (0.94 ml) in methylene chloride (28 ml) in the presence of triethylamine (1.55 ml) by a conventional method.

IR (film): 3400 (broad), 1720 cm$^{-1}$

NMR (CDCl$_3$, δ): 2.06 (3H, s), 2.32 (1H, broad t, J=4Hz), 4.73 (2H, broad d, J=4Hz), 5.20 (2H, s), 7.23–7.53 (4H, m)

Preparation 2

Sodium borohydride (0.248 g) was added portionwise to a solution of 4-acetamido-2-methyl benzaldehyde (2.58 g) in methanol (26 ml) with ice-cooling. After being stirred for 3 hours, the mixture was evaporated in vacuo and the residue was washed with water and dried to give 4-acetamido-2-methylbenzyl alcohol (2.22 g).

mp : 133° to 134° C.

IR (Nujol): 3275, 3225, 1660, 1610, 1540, 1500, 1005 cm$^{-1}$

NMR (DMSO-d$_6$, δ): 2.03 (3H, s), 2.23 (3H, s), 4.43 (2H, d, J=5Hz), 4.90 (1H, t, J=5Hz), 7.10–7.56 (3H, m), 9.75 (1H, br s)

Preparation 3

A solution of 2-formamido-6-methylbenzyl alcohol (1.9 g) in tetrahydrofuran (26 ml) was added dropwise to a suspension of lithium aluminum hydride (0.873 g) in tetrahydrofuran (17 ml) at room temperature over a period of 10 minutes. After being refluxed for 4.5 hours, the excess reagent was decomposed with a small amount of water and the resulting precipitates were filtered off by suction. The filtrate was evaporated in vacuo and the residue was recrystallized from carbon tetrachloride to give 6-methyl-2-methylaminobenzyl alcohol (0.86 g).

mp 67° to 70° C.
IR (Nujol) : 3330, 3180, 1580, 1310, 1000 cm−1
NMR (CDCl$_3$δ): 2.32 (3H, s), 2.85 (3H, s), 3.00 (2H, br s), 4.70 (2H, s), 6.55 (2H, d, J=7.5Hz), 7.15 (1H, t, J=7.5Hz)

Preparation 4

A mixture of 3-hydroxy-2-nitropyridine (3.08 g) and potassium carbonate (3.04 g) in N,N-dimethylformamide (31 ml) was stirred at room temperature for 15 minutes and then 2-methoxycarbonylamino-6-methylbenzyl chloride (4.7 g) was added. After being stirred for 6 hours, the mixture was poured into water and the resulting precipitates were collected by filtration, washed with water, and air-dried to give 3-(2-methoxycarbonylamino-6-methylbenzyloxy)-2nitropyridine (6.35 g).

mp: 118° to 119° C. (recrystallized from ethanol)
IR (Nujol): 3280, 1700, 1595, 1515 cm−1
NMR (CDCl$_3$, δ): 2.40 (3H, s), 3.73 (3H, s), 5.23 (2H, s), 6.90–7.80 (6H, m), 8.07–8.20 (1H, m)

Preparation 5

The following compounds were prepared according to a similar manner to that of Preparation 4.
(1) 2-Amino-3-(2-trifluoromethylbenzyloxy)pyridine
mp: 112° to 113° C. (recrystallized from a mixture of ethyl acetate and n-hexane)
NMR (CDCl$_3$, δ): 4.77 (2H, br s), 5.26 (2H, s), 6.41–6.73 (1H, m), 6.91 (1H, dd, J=1Hz, 8Hz), 7.25–7.90 (5H, m)
3-(2-Acetamidobenzyloxy)-2-nitropyridine
mp: 107° to 108° C.
IR (Nujol): 3240, 1640, 1590, 1530 cm−1
NMR (CDCl$_3$δ): 2.25 (3H, s), 5.25 (2H, s), 7.06–8.23 (7H, m), 8.33 (1H, br s )
(3) 3-(2ethoxycarbonylaminobenzyloxy)-2-nitropyridine
mp: 92° to 94° C.
IR (Nujol) : 3400, 1722, 1585, 1535, 1275 cm−1
NMR (CDCl$_3$, δ): 3.80 (3H, s), 5.26 (2H, s), 6.98–8.00 (7H, m), 8.07–8.23 (1H, m)
(4) 3-(2-Formamidobenzyloxy)-2-nitropyridine
mp: 155° to 157° C.
IR (Nujol) : 3200, 1685, 1595, 1585, 1520 cm−1
NMR (CDCl$_3$, δ): 5.33,5.38 (2H, each s), 7.10–8.30 (8H, m), 9.60–10.00 (1H, broad m)
(5) 2-Amino-3-(2-cyanobenzyloxy)pyridine
IR (Nujol): 3450, 3250, 3100, 2225, 1625, 1595, 1560 cm−1
(6) 2-Amino-3-(2-methoxymethoxybenzyloxy)pyridine
mp: 85° to 87° C. (recrystallized from ethyl acetate)
IR (Nujol): 3460, 3280, 3150, 1620, 1595, 1555 cm−1
NMR (CDCl$_3$, δ): 3.46 (3H, s), 4.73 (2H, br s), 5.15 (2H, s), 5.23 (2H, s), 6.58 (1H, dd, J=5Hz, 8Hz), 6.86–7.56 (5H, m), 7.68 (1H, dd, J=2Hz, 5Hz)
(7) 2-Amino-3-(3-methoxymethoxybenzyloxy)pyridine
mp: 74° to 75° C.
IR (Nujol) : 3475, 3300, 3140, 1630, 1590, 1480, 1280 cm−1
NMR (CDCl$_3$, δ): 3.48 (3H, s), 4.73 (2H, broads), 5.03 (2H, s), 5.20 (2H, s), 6.43–6.73 (1H, m), 6.87–7.50 (5H, m), 7.60–7.80 (1H, m)
(8) 3-(2,6-Dimethylbenzyloxy)-2-nitropyridine
mp: 114° to 115° C. (recrystallized from a mixture of benzene and n-hexane)
IR (Nujol): 1590, 1515, 1420, 1270, 1110 cm−1
NMR (CDCl$_3$, δ): 2.37 (6H, s), 5.20 (2H, s), 6.90–7.30 (3H, m), 7.33–7.77 (2H, m), 8.00–8.20 (1H, m)
(9) 3-(2-Isonicotinamido-6-methylbenzyloxy)-2-nitropyridine pyridine
mp: 118° to 122° C.
IR (Nujol): 3160, 1650, 1595, 1520 cm−1
NMR (CDCl$_3$, δ): 2.43 (3H, s), 5.26 (2H, s), 7.16 (1H, d, J=8Hz), 7.37 (1H, t, J=8Hz), 7.43–7.83 (5H, m), 8.10–8.20 (1H, m), 8.66–8.80 (2H, m), 8.91 (1H, broad s)
(10) 3-(2-Methyl-6-propionamidobenzyloxy)-2-nitropyridine
mp: 134° to 135° C.
IR (Nujol) : 3210, 1635, 1580, 1550, 1530 cm−1
NMR (CDCl$_3$δ): 1.20 (3H, t, J=7.5Hz), 2.43 (3H, s), 2.45 (2H, q, J=7.5Hz), 5.24 (2H, s), 7.08 (1H, d, J=7Hz), 7.33 (1H, t, J=7Hz), 7.50–7.80 (3H, m), 8.08 (1H, broad s), 8.20 (1H, dd, J=2Hz, 4.5Hz)
(11) 3-(2-t-Butoxycarbonylaminoacetamido-6-methylbenzyloxy)-2-nitropyridine
mp: 156° to 158° C.
IR (Nujol) 3300, 1710, 1685, 1595, 1530 cm−1
(CDCl$_3$, δ): 1.30 (9H, s), 2.40 (3H, s), 3.95 (2H, d, J=6Hz), 5.20 (2H, s), 5.30 (1H, t, J=6Hz), 7.08 (1H, d, J=7.5Hz), 7.30 (1H, t, J=7.5Hz), 7.50–7.83 (3H, m), 8.17 (1H, dd, J=2Hz, 4.5Hz), 8.58 (1H, broad s)
(12) 3-(2-Benzyloxycarbonylamino-6-methylbenzyloxy)-2-nitropyridine
mp: 116° to 118° C. (recrystallized from a mixture of diethyl ether and n-hexane)
IR (Nujol) 3225, 1718, 1590, 1520 cm−1
NMR (CDCl$_3$, δ): 2.40 (3H, s), 5.21 (4H, s), 6.93–7.73 (12H, m), 8.06–8.20 (1H, m)
(13) 3-(2 Isopropoxycarbonylamino-6-methylbenzyloxy)-2-nitropyridine
mp: 106° to 107° C. (recrystallized from a mixture of diethyl ether and n-hexane)
IR (Nujol) : 3200, 1670, 1590, 1523 cm−1
NMR (CDCl$_3$, δ): 1.29 (6H, d, J=6Hz), 2.42 (3H, s), 5.0 (1H, septet, J=6Hz), 5.26 (2H, s),
6.93–7.76 (6H, m), 8.08–8.23 (1H, m) (14) 3-(4-Acetamido-2-methylbenzyloxy)-2-aminopyridine
mp: 189° to 193° C. (recrystallized from a mixture of ethanol and n-hexane)
IR (Nujol) : 3470, 3410, 3300, 1695, 1670, 1600, 1560, 1525 cm−1
NMR (DMSO d$_6$, δ) : 2.03 (3H, s), 2.30 (3H, s), 5.01 (2H, s), 5.52 (2H, br s), 6.50 (1H, dd, J=5Hz, 8Hz), 7.12 (1H, broad d, J=8Hz), 7.33–7.66 (4H, m), 9.84 (1H, br s)
(15) 3-[2-(N-Methoxycarbonyl-N-methylamino)-6-methylbenzyloxy]-2-nitropyridine
mp: 140° to 141° C. IR (Nujol) : 1690, 1590, 1520, 1310, 1265 cm−1
NMR (CDCl$_3$, δ): 2.40 (3H, s), 3.20 (3H, s), 3.63 (3H, s), 5.10 (2H, s), 6.93–7.83 (5H, m), 8.04–8.23 (1H, m)

(16) 3-(2-Acetoxyacetamido-6-methylbenzyloxy)-2-nitropyridine
mp: 140° to 141° C. (recrystallized from a mixture of ethyl acetate and n-hexane)
IR (Nujol) : 3200, 1740, 1655, 1595, 1525 cm$^{-1}$
NMR (CDCl$_3$, δ): 1.90 (3H, s), 2.40 (3H, s), 4.65 (2H, s), 5.18 (2H, s), 6.95–7.87 (5H, m), 8.11 (1H, dd, J=2Hz, 4Hz), 8.30 (1H, broad s)

(17) 3-(2-t-Butoxycarbonylamino-6-methylbenzyloxy)-2-nitropyridine
mp: 101°–103° C.
IR (Nujol) : 3290, 1710, 1585, 1525 cm−1
NMR (CDCl$_3$, δ) : 1.5 (9H, s), 2.4 (3H, s), 5.26 (2H, s), 6.9–7.8 (6H, m), 8.06–8.23 (1H, m)

Preparation 6

A mixture of 2-amino-3-(4-cyanobenzyloxy)pyridine (4.2 g) and 23% solution of hydrogen chloride in ethanol (84 ml) was refluxed for 10 hours. The mixture was filtered by suction and the filtrate was evaporated in vacuo. The residue was treated with an aqueous solution of sodium bicarbonate and the resulting precipitates were collected by filtration. The crude product was purified by column chromatography on silica gel (87 g) with chloroform and a mixture of chloroform and methanol (100:2) as eluents to give 2-amino-3-(4-ethoxycarbonylbenzyloxy)pyridine (3.17 g).
mp : 110° to 111° C.
IR (Nujol): 3480, 3290, 3125, 1715, 1635, 1480, 1280 cm$^{-1}$
NMR (CDCl$_3$, δ) : 1.40 (3H, t, J=7.5Hz), 4.36 (2H, d, J=7.5 Hz), 4.75 (2H, broad s), 5.10 (2H, s), 6.52 (1H, dd, J=5Hz, 7.5Hz), 6.88 (1H, dd, J=2Hz, 5Hz), 7.42 (2H, d, J=8Hz), 7.53–7.70 (1H, m), 8.02 (2H, d, J=8Hz)

Preparation 7

A mixture of 2-amino-3-(4-cyanobenzyloxy)pyridine (2.25 g) and 1N sodium hydroxide solution (22 ml) in methanol (45 ml) was refluxed for 4.5 hours and then cooled. The resulting precipitates were collected by filtration and dried to give 2-amino-3-(4-carbamoylbenzyloxy)pyridine (1.84 g).
IR (Nujol) : 3475, 3380, 3290, 3160, 3100, 1635, 1610, 1565 cm$^{-1}$
NMR (DMSO-d$_6$, δ): 5.15 (2H, s), 5.65 (2H, s), 6.47 (1H, dd, J=4.5Hz, 8Hz), 7.15 (1H, dd, J=2Hz, 8Hz), 7.33 (1H, br s), 7.42–7.62 (1H, m), 7.53 (2H, d, J=8Hz), 7.70–8.10 (1H, broad s), 7.88 (2H, d, J=8Hz)

Preparation 8

The following compound was prepared according to a similar manner to that of Preparation 7.
2-Amino-3-(2-carbamoylbenzyloxy)pyridine
mp 204° to 206° C.
IR (Nujol) : 3460, 3280, 3125, 1660, 1620, 1595, 1560 cm$^{-1}$
NMR (DMSO-d$_6$, δ): 5.26 (2H, s), 5.63 (2H, br s), 6.46 (1H, dd, J=5Hz, 8Hz), 7.03 (1H, dd, J=2Hz, 8Hz), 7.28–8.06 (7H, m)

Preparation 9

Raney nickel catalyst (8 ml) was added to a solution of 3-dimethylaminomethyl-2-methyl-8-(2nitrobenzyloxy)imidazo[1,2-a]pyridine (4 g) in methanol (60 ml) and the mixture was shaken under an atmospheric pressure until the absorption of hydrogen ceased. The catalyst was filtered off, the filtrate was evaporated in vacuo, and the residue was dissolved in methylene chloride. The solution was washed successively with aqueous sodium carbonate, water, and brine, dried over magnesium sulfate, and evaporated in vacuo. The residue was crystallized from diethyl ether to give 8-(2-aminobenzyloxy)-3-dimethylamino-methyl-2-methylimidazo[1,2-a]pyridine (2.07 g).
mp: 124° to 128° C.
IR (Nujol): 3450, 3300 cm−1
NMR (CDCl$_3$, δ): 2.23 (6H, s), 2.45 (3H, s), 3.53–4.23 (2H, b), 3.60 (2H, s), 5.26 (2H, s), 6.51–6.85 (4H, m), 6.96–7.33 (2H, m), 7.83 (1H, t, J=4Hz)

Preparation 10

To a mixture of iron powder (2.76 g) and ammonium chloride (0.275 g) in water (19 ml) and ethanol (63 ml) was added portionwise 3-(2-methoxycarbonylamino-6-methylbenzyloxy)-2-nitropyridine (6.27 g) under reflux and then stirred for an additional 30 minutes. The hot mixture was filtered by suction and the filtrate was made alkaline with sodium bicarbonate and evaporated in vacuo. The residue was washed with water, dried, and recrystallized from ethyl acetate to give 2-amino-3-(2-methoxycarbonylamino-6-methylbenzyloxy)pyridine.
mp: 146° to 148° C.
IR (Nujol) : 3430, 3375, 3270, 3150, 1730, 1620, 1585, 1520, 1230, 1190 cm$^{-1}$
NMR (CDCl$_3$, δ): 2.37 (3H, s), 3.73 (3H, s), 4.62 (2H, broad s), 5.03 (2H, s), 6.47–6.67 (1H, m), 6.90–7.35 (4H, m), 7.50–7.73 (2H, m)

Preparation 11

The following compounds were prepared according to similar manners to those of Preparations 9 or 10.
(1) 2-Amino-3-(2-acetamidobenzyloxy)pyridine
mp: 152° to 154° C. (recrystallized from ethyl acetate)
IR (Nujol) : 3425, 3390, 3300, 3150, 1680, 1638, 1600, 1585, 1520 cm$^{-1}$
NMR (DMSO-d$_6$, δ): 2.05 (3H, s), 5.07 (2H, s), 5.63 (2H, br s), 6.48 (1H, dd, J=5Hz, 8Hz), 6.93–7.70 (6H, m), 9.46 (1H, br s)
(2) 2-Amino-3-(2-methoxycarbonylaminobenzyloxy)pyridine
mp: 170° to 172° C.
IR (Nujol) : 3440, 3390, 3280, 3130, 1730, 1630, 1585, 1520 cm$^{-1}$
NMR (CDCl$_3$, δ) : 3.77 (3H, s), 5.07 (2H, s), 7.63–8.03 (2H, m)
(3) 2-Amino-3-(2-formamidobenzyloxy)pyridine
mp: 143° to 145° C.
IR (Nujol) : 3450, 3300, 1680, 1625, 1590, 1520 cm$^{-1}$
NMR (CDCl$_3$, δ): 4.30–4.90 (2H, broad s), 5.04 (2H, s), 6.47–6.70 (1H, m), 6.90–8.70 (8H, m)
(4) 2-Amino-3-(2-isonicotinamido-6-methylbenzyloxy)pyridine
mp: 186° to 188° C.
IR (Nujol): 3475, 3235, 3125, 1655, 1620, 1520 cm$^{-1}$
NMR (DMSO-d$_6$, δ): 2.43 (3H, s), 5.06 (2H, s), 5.51 (2H, s), 6.46 (1H, dd, J=4.5 Hz, 7.5 Hz), 7.13 (1H, broad d, J=7.5 Hz), 7.16–7.43 (3H, m), 7.51 (1H, dd, J=1.5 Hz, 4.5 Hz), 7.80–7.93 (2H, m), 8.73–8.86 (2H, m), 10.33 (1H, s)
(5) 2-Amino-3-(2-methyl-6-propionamidobenzyloxy)pyridine
mp: 161° to 162° C.
IR (Nujol): 3450, 3280, 3120, 1640, 1610, 1520 cm$^{-1}$
NMR (CDCl$_3$, δ): 1.15 (3H, t, J=8 Hz), 2.35 (2H, q, J=8 Hz), 2.41 (3H, s), 4.63 (2H, broad s), 5.05 (2H, s), 6.53–6.80 (1H, m), 6.96–7.87 (6H, m)

(6) 2-Amino-3-[2,6-bis(hydroxymethyl)benzyloxy]pyridine mp: 146° to 148° C.

IR (Nujol): 3480, 3325, 1620, 1200 cm$^{-1}$

NMR (DMSO-d$_6$, δ): 4.63 (4H, d, J=5 Hz), 5.12 (2H, s), 5.17 (2H, t, J=5 Hz), 5.50 (2H, broad s), 6.55 (1H, dd, J=5 Hz, 7.5 Hz), 7.23 (1H, broad d, J=7.5 Hz), 7.40 (3H, s), 7.57 (1H, broad d, J=5 Hz)

(7) 2-Amino-3-(2-hydroxymethyl-6-methylbenzyloxy)pyridine mp: 55° to 58° C.

IR (Nujol): 3480, 3300, 1610, 1200 cm$^{-1}$

NMR (CDCl$_3$, δ): 2.40 (3H, s), 2.20–2.60 (1H, br s), 4.63 (2H, broad s), 4.73 (2H, s), 5.13 (2H, s), 6.62 (1H, dd, J=5 Hz, 7.5 Hz), 7.12 (1H, broad d, J=7.5 Hz), 7.13–7.40 (3H, m), 7.65 (1H, broad)

(8) 2-Amino-3-(2-t-butoxycarbonylaminoacetamido-6-methylbenzyloxy)pyridine mp: 169° to 170° C.

IR (Nujol): 3480, 3435, 3360, 1703, 1685, 1615, 1200 cm$^{-1}$

NMR (CDCl$_3$, δ): 1.38 (9H, s), 2.40 (3H, s), 3.88 (2H, d, J=6 Hz), 4.70 (2H, broad s), 5.10 (2H, s), 5.33–5.70 (1H, m), 6.47–6.83 (1H, m), 6.83–7.50 (3H, m), 7.60–7.93 (2H, m), 8.75 (1H, broad s)

(9) 2-Amino-3-(2-benzyloxycarbonylamino-6-methylbenzyloxy)pyridine mp: 107° to 109° C. (recrystallized from diethyl ether)

IR (Nujol): 3460, 3350, 1700, 1615, 1585, 1540 cm$^{-1}$

NMR (CDCl$_3$, δ): 2.39 (3H, s), 4.63 (2H, br s), 5.06 (2H, s), 5.20 (2H, s), 6.63 (1H, dd, J=5 Hz, 8 Hz), 7.05 (1H, dd, J=2 Hz, 8 Hz), 7.16–7.50 (8H, m), 7.63 (1H, br s), 7.73 (1H, dd, J=2 Hz, 5 Hz)

(10) 2-Amino-3-(2-isopropoxycarbonylamino-6-methylbenzyloxy)pyridine mp: 112° to 114° C. (recrystallized from a mixture of diethyl ether and n-hexane)

IR (Nujol): 3450, 3280, 1685, 1620, 1510 cm$^{-1}$

NMR (CDCl$_3$, δ): 1.26 (6H, d, J=7 Hz), 2.37 (3H, s), 4.68 (2H, br s), 5.0 (1H, septet, J=7 Hz), 5.06 (2H, s), 6.62 (1H, dd, J=5 Hz, 8 Hz), 6.90–7.23 (3H, m), 7.38 (1H, d, J=8 Hz), 7.56–7.83 (2H, m)

(11) 2-Amino-3-[2-(N-methoxycarbonyl-N-methylamino)-6-methylbenzyloxy]pyridine mp: 115° to 117° C.

IR (Nujol): 3480, 3270, 3100, 1690, 1620, 1200 cm$^{-1}$

NMR (CDCl$_3$, δ): 2.43 (3H, s), 3.20 (3H, s), 3.65 (3H, s), 4.63 (2H, br s), 4.95 (2H, s), 6.53–6.77 (1H, m), 7.00–7.47 (4H, m), 7.63–7.80 (1H, m)

(12) 3-(2-Acetoxyacetamido-6-methylbenzyloxy)-2-aminopyridine mp: 151° to 152° C.

IR (Nujol): 3460, 3330, 1740, 1685, 1620, 1555 cm$^{-1}$

NMR (CDCl$_3$, δ): 1.73 (3H, s), 2.43 (3H, s), 4.67 (2H, s), 5.10 (2H, s), 6.57–6.87 (1H, m), 7.0–7.57 (3H, m), 7.67–8.02 (2H, m), 8.50 (1H, broad s)

(13) 2-Amino-3-(2-t-butoxycarbonylamino-6-methylbenzyloxy)pyridine mp: 116°–118° C.

IR (Nujol): 3475, 3425, 3275, 3125, 1725, 1620, 1595, 1580, 1510 cm$^{-1}$

NMR (CDCl$_3$, δ): 1.50 (9H, s), 2.38 (3H, s), 4.63 (2H, br s), 5.08 (2H, s), 6.65 (1H, dd, J=5 Hz, 8 Hz), 6.90–7.20 (3H, m), 7.30 (1H, t, J=8 Hz), 7.56–7.86 (2H, m)

PREPARATION 12

(1) To a suspension of 3-(2,6-dimethylbenzyloxy)-2-nitropyridine (2.6 g) in a mixture of acetic acid (26 ml), acetic anhydride (39 ml) and sulfuric acid (5 ml) was added chromium trioxide (2.5 g) portionwise during a period of 20 minutss at 10° C. After being stirred for 2 hours at the same temperature the reaction mixture was poured into ice-water and extracted with ethyl acetate. The extracts were washed with water, dried over magnesium sulfate and the solvent was evaporated under reduced pressure. The residue was dissolved in ethyl alcohol and the solution was made strongly basic to litmus with an aqueous solution of 24% sodium hydroxide with ice-cooling. After being stirred for 2.5 hours at an ambient temperature, the mixture was diluted with ice water. The resulting precipitates were filtrated off and dried to give a mixture (1.29 g) of 3-(2,6-diformylbenzyloxy)-2-nitropyridine and 3-(2-formyl-6-methylbenzyloxy)-2-nitropyridine.

(2) To a solution of a mixture (1.29 g) of 3-(2,6-diformylbenzyloxy)-2-nitropyridine and 3-(2-formyl-6-methylbenzyloxy)-2-nitropyridine in ethyl alcohol (30 ml) was added portionwise sodium borohydride (390 mg) with ice-cooling. After being stirred for 3 hours with ice-cooling, the reaction mixture was poured into ice-water and the resulting precipitates were filtrated off. The precipitates were subjected to column chromatography on silica gel (40 g), eluting with a mixture of chloroform and methanol (20:1) to give 3-(2-hydroxymethyl-6-methylbenzyloxy)-2-nitropyridine (330 mg) and 3-[2,6-bis(hydroxymethyl)benzyloxy]-2-nitropyridine (700 mg).

3-(2-Hydroxynethyl-6-methylbenzyloxy)-2-nitropyridine.

mp: 98° to 101° C.

IR (Nujol): 3225, 1595, 1560, 1530, 1285, 1110 cm$^{-1}$ (CDCl$_3$, δ): 1.97 (1H, t, J=5 Hz), 2.43 (3H, s), 4.74 (2H, s), 5.33 (2H, s), 7.25 (3H, s), 7.53 (1H, dd, J=4.5 Hz, 8 Hz), 7.73 (1H, dd, J=2 Hz, 8 Hz), 8.10 (1H, dd, J=2 Hz, 4.5 Hz)

3-[2,6-Bis(hydroxymethyl)benzyloxy]-2-nitropyridine.

mp: 141° to 142° C.

IR (Nujol): 3400, 1600, 1538, 1280, 1080 cm$^{-1}$

NMR (CDCl$_3$, DMSO-d$_6$,3:1, δ): 4.4–4.87 (2H, broad s), 4.70 (4H, s), 5.45 (2H, s), 7.40 (3H, s), 7.62 (1H, dd, J=4.5 Hz, 8 Hz), 7.93 (1H, dd, J=2 Hz, 8 Hz), 8.13 (1H, dd, J=2 Hz, 4.5 Hz)

PREPARATION 13

A solution of 2-amino-3-(4-ethoxycarbonylbenzyloxy)pyridine (1.04 g) in tetrahydrofuran (15 ml) was added dropwise to a suspension of lithium alminum hydride (0.24 g) in tetrahydrofran (24 ml) with ice cooling over a period of 10 minutes. After being stirred for 1.5 hours at room temperature, the excess reagent was decomposed with a small amount of water and the resulting precipitates were filtered off by suction. The filtrate was evaporated in vacuo and the crystalline residue was washed with diethyl ether to give 2-amino-3-(4-hydroxymethylbenzyloxy)pyridine (0.79 g).

mp: 120° to 121° C.

IR (Nujol): 3420, 3305, 1620, 1285, 1195

NMR (CDCl$_3$, δ): 4.67 (3H, s), 5.00 (2H, s), 6.50 (1H, dd, J=5 Hz, 7.5 Hz), 6.88 (1H, dd, J=1.5 Hz, 7.5 Hz), 7.33 (4H, s), 7.55 (1H, dd, J=1.5 Hz, 5 Hz)

PREPARATION 14

A mixture of 2-amino-3-(3-methoxymethoxybenzyloxy)pyridine (7.6 g) and 10% sulfuric acid (150 ml) was stirred at room temperature for 4 hours and the resulting precipitates were collected by filtration. The obtained sulfate was treated with an aqueous solution of sodium bicarbonate and the precipitates were collected by filtration, washed with water, and air-dried to give 2-amino-3-(3-hydroxybenzyloxy)pyridine (4.88 g).

mp 169° to 173° C.

IR (Nujol): 3450, 3340, 1610, 1290, 1210 cm$^{-1}$

NMR (DMSO-d$_6$, δ): 5.07 (2H, s), 5.30–6.00 (2H, broad s), 6.30–7.30 (7H, m), 7.43–7.60 (1H, m), 8.90–9.80 (1H, broad s)

PREPARATION 15

A solution of 2-amino-3-(2-acetoxyacetamido-6-methylbenzyloxy)pyridine (0.63 g) and 1N sodium hydroxide solution (2 ml) in methanol (20 ml) was stirred at room temperature for 1 hour. The resulting precipitates were collected by filtration to give 2-amino-3-(2-hydroxyacetamido-6-methylbenzyloxy)pyridine.

mp: 207° to 209° C. (dec.)

IR (Nujol): 3440, 3350, 1675, 1625, 1540 cm$^{-1}$

NMR (DMSO-d$_6$, δ): 2.43 (3H, s), 4.03 (2H, s), 5.12 (2H, s), 5.50 (2H, br s), 6.43–7.73 (1H, m), 7.0–7.8 (5H, m)

PREPARATION 16

Acetic anhydride (0.43 g) was added dropwise to a solution of 8-(2-aminobenzyloxy)-3-dimethylaminomethyl-2-methylimidazo[1,2 a]pyridine (1 g) in methylene chloride (13 ml) with ice cooling. After being stirred for 5 hours at room temperature the reaction solution was washed successively with aqueous sodium bicarbonate, water, and brine, dried over magnesium sulfate, and evaporated in vacuo. The residue was purified by column chromatography on silica gel (20 g) with a mixture of methylene chloride and methanol (50:1–20:1) as an eluent to give 8-(2-acetamidobenzyloxy)-3-dimethylaminomethyl-2-methylimidazo[1,2-a]pyridine (0.88 g)

mp: 193° to 195° C.

NMR (CDCl$_3$, δ): 2.26 (9H, s), 2.45 (3H, s), 3.63 (2H, s), 5.32 (2H, s), 6.56–6.80 (2H, m), 6.87–7.50 (3H, m), 7.76–8.20 (2H, m), 9.33 (1H, br s)

PREPARATION 17

Acetic formic anhydride (1.85 g) was added to a solution of 2-amino-6-methylbenzyl alcohol (2.74 g) in benzene (55 ml) at room temperature. After being stirred for 2 hours, the mixture was diluted with n-hexane (10 ml) and the precipitates were collected by filtration to give 2-formamido-6-methylbenzyl alcohol (2.8 g).

mp: 99° to 100° C.

IR (Nujol): 3240, 1660, 1595, 1575, 1520 cm$^{-1}$

NMR (DMSO-d$_6$, δ): 2.33 (3H, s), 4.48 (2H, s),

| 6.83–7.23 | } (3H, m), | 8.24 (s) | } (1H) |
| 7.43–7.63 | | 8.37 (s) | |

PREPARATION 18

A mixture of 2-amino-6-methylbenzyl alcohol (0.274 g) and methyl isocyanate (0.11 g) in benzene (5.2 ml) was stirred at room temperature for 15 minutes. The resulting precipitates were collected by filtration and dried to give 6-methyl-2-(3-methyl ureido)benzyl alcohol (0.24 g).

mp: 158° to 160° C. (dec.)

IR (Nujol): 3375, 3260, 1665, 1600, 1550, 990 cm$^{-1}$

NMR (DMSO-d$_6$, δ): 2.30 (3H, s), 2.62 (3H, d, J=4.5 Hz), 4.47 (2H, broad d), 4.7–5.3 (1H, m), 6.47–6.80 (1H, m), 6.80 (1H, dd, J=2 Hz, 8 Hz), 7.05 (1H, t, J=8 Hz), 7.53 (1H, dd, J=2 Hz, 8 Hz), 7.90 (1H, s)

PREPARATION 19

A solution of methyl chloroformate (0.416 g) in methylene chloride (1 ml) was added dropwise to a solution of 2-amino-6-methylbenzyl alcohol (0.549 g) and pyridine (0.364 g) in methylene chloride (10 ml) with ice cooling. After being stirred for 1 hour, the mixture was poured into 1N hydrochloric acid and extracted with methylene chloride. The extract was washed with water, dried over magnesium sulfate, and evaporated in vacuo. The crystalline residue was washed with n-hexane and dried to give 2-methoxycarbonylamino-6-methylbenzyl alcohol (0.64 g).

mp: 111° to 113° C.

IR (Nujol): 3450, 3260, 1685, 1602, 1580, 1540 cm$^{-1}$

NMR (CDCl$_3$, δ): 2.36 (3H, s), 2.46 (1H, t, J=6 Hz), 3.73 (3H, s), 4.67 (2H, d, J=6 Hz), 6.87 (1H, d, J=7.5 Hz), 7.11 (1H, t, J=7.5 Hz), 7.47 (1H, d, J=7.5 Hz), 7.40–7.70 (1H, broad s)

PREPARATION 20

To a solution of t-butoxycarbonylaminoacetic acid (3.5 g) in methylene chloride (50 ml) was added triethylamine (2.0 g) and then ethyl chloroformate (1.9 ml) with ice-cooling. After being stirred for 1 hour, 2-amino-6-methylbenzyl alcohol (2.74 g) was added thereto and the mixture was stirred for 7 days at an ambient temperature. To the mixture was added a saturated aqueous solution of sodium hydrogen carbonate and the organic layer was separated, washed with water and dried over magnesium sulfate. The solvent was distilled off and the residue was triturated with diethyl ether to give 2-(t-butoxycarbonylaminoacetamido)-6-methylbenzyl alcohol (1.04 g).

mp: 138° to 141° C.

IR (Nujol): 3410, 3270, 1705, 1645, 1595, 1575, 1240 cm$^{-1}$

NMR (CDCl$_3$, δ): 1.45 (9H, s), 2.35 (3H, s), 3.86 (2H, d, J=6 Hz), 4.63 (2H, s), 5.55 (1H, t, J=6 Hz), 6.86–7.06 (1H, m), 7.17 (1H, t, J=7.5 Hz), 7.57 (1H, broad d, J=7.5 Hz), 9.10 (1H, broad s)

PREPARATION 21

A solution of potassium cyanate (1.62 g) in water (5 ml) was dded dropwise to a mixture of 2-amino-6-methylbenzyl alcohol (1.37 g), water (5 ml), and acetic acid (6 ml) at room temperature. After being stirred for 2.5 hours, the resulting precipitates were collected by filtration, washed with water, and dried to give 6-methyl-2-ureidobenzyl alcohol (1.33 g).

mp: 161° to 163° C. (dec.) (recrystallized from ethanol)

IR (Nujol): 3350, 3270, 1655, 1590, 1530, 1000 cm$^{-1}$

NMR (DMSO-d$_6$, δ): 2.32 (3H, s), 4.45 (2H, d, J=5 Hz), 4.93 (1H, d, J=5 Hz), 6.08 (2H, broad s), 6.82 (1H, d, J=8 Hz), 7.05 (1H, t, J=8 Hz), 7.55 (1H, d, J=8 Hz), 7.93 (1H, s)

PREPARATION 22

The following compounds were prepared according to similar manners to those of Preparations 16 to 21.

(1) 2-Benzyloxycarbonylamino-6-methylbenzyl alcohol mp: 91° to 93° C.

IR (Nujol): 3430, 3375, 1700, 1600, 1585, 1525 cm$^{-1}$

NMR (CDCl$_3$, δ): 2.33 (3H, s), 2.23–2.73 (1H, br s), 4.66 (2H, s), 5.16 (2H, s), 6.92 (1H, d, J=8 Hz), 7.16 (1H, t, J=8 Hz), 7.26-7.50 (5H, m), 7.57 (1H, d, J=8 Hz), 7.80 (1H, br s)

(2) 2-Isopropoxycarbonylamino-6-methylbenzyl alcohol
mp: 59° to 61° C. (recrystallized from n-hexane)
IR (Nujol): 3420, 3325, 1700, 1600, 1590, 1520 cm$^{-1}$
NMR (CDCl$_3$, δ): 1.28 (6H, d, J=6 Hz), 2.36 (3H, s), 2.70 (1H, br s), 4.69 (2H, s), 5.00 (1H, septet, J=6 Hz), 6.96 (1H, d, J=7 Hz), 7.20 (1H, t, J=7 Hz), 7.50-7.66 (2H, m)

(3) 2 Ethoxycarbonylamino-6-methylbenzyl alcohol
mp: 58° to 59° C. (recrystallized from n-hexane)
IR (Nujol): 3415, 3320, 1695, 1685, 1620, 1600 cm$^{-1}$
NMR (CDCl$_3$, δ): 1.30 (3H, t, J=7 Hz), 2.36 (3H, s), 2.30-2.70 (1H, br s), 4.21 (2H, q, J=7 Hz), 4.70 (2H, s), 6.93 (1H, b, d,d, J=2 Hz, 8 Hz), 7.19 (1H, t, J=8 Hz), 7.55 (1H, b, d,d, J=2 Hz, 8 Hz), 7.50-7.80 (1H, br s)

(4) 2-Methanesulfonylamino-6-methylbenzyl alcohol
mp: 79° to 81° C. (recrystallized from cyclohexane)
IR (Nujol): 3380, 3225, 3050, 1580, 1515, 1140, 1095, 1070 cm$^{-1}$
NMR (CDCl$_3$, δ): 2.39 (3H, s), 2.87 (1H, b.t, J=5 Hz), 3.01 (3H, s), 4.82 (2H, b,d, J=5 Hz), 6.93-7.40 (3H, m), 7.69 (1H, br s)

(5) 3-Acetamido-2-methylbenzyl alcohol
mp: 117° to 118° C.
IR (Nujol) 3250, 1645, 1600, 1535, 1100 cm$^{-1}$
NMR (DMSO-d$_6$, δ): 2.02 (3H, s), 2.06 (3H, s), 4.50 (2H, d, J=5 Hz), 5.02 (1H, t, J=5 Hz), 7.00-7.30 (3H, m), 9.29 (1H, br s)

(6) 2-(N-Methoxycarbonyl-N-methylamino)-6-methylbenzyl alcohol
IR (film): 3400, 1680, 1580, 1370, 1310, 1190, 1160, 1000 cm$^{-1}$
NMR (CDCl$_3$, δ): 2.48 (3H, s), 3.23 (3H, s), 3.77 (3H, br s), 4.53 (2H, d, J=6 Hz), 6.93-7.37 (HH, m)

(7) 2-Acetoxyacetamido-6-methylbenzyl alcohol
mp: 108° to 110° C. (recrystallized from ethyl acetate)
IR (Nujol): 3280, 1760, 1660, 1605, 1580, 1530, 1210 cm$^{-1}$
NMR (CDCl$_3$, δ): 2.23 (3H, s), 2.40 (3H, s), 2.60 (1H, t, J=7.5 Hz), 4.70 (2H, s), 4.73 (2H, d, J=7.5 Hz), 6.87-7.43 (2H, m), 7.70-7.93 (1H, m), 9.23 (1H, br s)

(8) 2-t-Butoxycarbonylamino-6-methylbenzyl alcohol
mp 96° to 98° C.
IR (Nujol): 3450, 3320, 1695, 1600, 1580, 1520 cm$^{-1}$
NMR (CDCl$_3$, δ): 1.50 (9H, s), 2.40 (2H, s), 4.73 (2H, d, J=6 Hz), 6.80-7.63 (4H, m)

(9) 2-Acetamido-6-methylbenzyl alcohol
mp: 118° to 119° C.
IR (Nujol): 3360, 3280, 1645, 1600, 1530 cm$^{-1}$
NMR (DMSO-$_6$, δ): 2.07 (3H, s), 2.37 (3H, s), 4.50 (2H, s), 6.87-7.47 (3H, m), 9.33 (1H, br s)

(10) 2-Acetamidobenzyl alcohol
mp: 114° to 115° C.
IR (Nujol): 3275, 3190, 1650, 1580, 1525, 1037 cm$^{-1}$
NMR (DMSO-d$_6$, δ): 2.06 (3H, s), 3.63 (1H, br s), 4.61 (2H, b.d), 7.03-7.50 (3H, m), 7.76-8.06 (1H, m), 8.76 (1H, br s)

(11) 2-Ureidobenzyl alcohol
mp: 174° to 176° C.
IR (Nujol): 3420, 3300, 3180, 1640, 1595, 1540, 1045 cm$^{-1}$
NMR (DMSO-d$_6$, δ): 4.47 (2H, d, J=6 Hz), 5.23 (1H, t, J=6 Hz), 6.10 (2H, broad s), 6.80-7.40 (3H, m), 7.60-8.00 (2H, m)

(12) 2-Methoxycarbonylaminobenzyl alcohol
IR (film): 3330, 1700, 1590, 1520 cm$^{-1}$
NMR (CDCl$_3$, δ): 2.50-2.90 (1H, broad s), 3.75 (3H, s), 4.67 (2H, s), 6.83-7.53 (3H, m), 7.70-8.13 (2H, m)

(13) 2-Isonicotinamido-6-methylbenzyl alcohol
mp: 133° to 135° C. (recrystallized from benzene)
IR (Nujol): 3260, 1630, 1600, 1578, 1520, 1005 cm$^{-1}$
NMR (CDCl$_3$, δ): 2.30 (3H, s), 4.05 (1H, broad s), 4.83 (2H, s), 6.96 (1H, d, J=8 Hz), 7.21 (1H, t, J=8 Hz), 7.70-7.86 (2H, m), 8.01 (1H, d, J=8 Hz), 8.53-8,80 (2H, m), 10.21 (1H, s)

(14) 2-Methyl-6-propionamidobenzyl alcohol
mp: 75° to 76° C.
IR (Nujol): 3275, 1650, 1600, 1585, 1520, 1005 cm$^{-1}$
NMR (CDCl$_3$, δ): 1.20 (3H, t, J=7.5 Hz), 2.35 (3H, s), 2.37 (2H, q, J=7.5 Hz), 3.16 (1H, broad s), 4.60 (2H, s), 6.98 (1H, broad d, J=7.5 Hz), 7.16 (1H, t, J=7.5 Hz), 7.52 (1H, broad d, J=7.5 Hz), 8.52 (1H, broad s)

PREPARATION 23

A solution of methanesulfonyl chloride 1.7 g) in methylene chloride (3 ml) was added dropwise to a solution of 2-(N-methoxycarbonyl-N-methylamino)-6-methylbenzyl alcohol (1.04 g) and triethylamine (2.5 g) in methylene chloride (15 ml) at room temperature and the mixture was refluxed for 3 hours and the cooled. To the mixture was added an aqueous solution of sodium bicarbonate and extracted with methylene chloride. The extract was washed with water, dried over magnesium sulfate, and evaporated in vacuo to give 2-(N-methoxycarbonyl-N-methylamino)-6-methylbenzyl chloride (1.4 g).

IR (film): 1700, 1580, 1440, 1360, 1305, 1040, 1000, 960, 800 cm$^{-1}$
NMR (CDCl$_3$, δ): 2.46 (3H, s), 3.25 (3H, s), 3.63 (3H, br s), 4.46 (1H, d, J=12 Hz), 4.60 (1H, d, J=12 Hz), 6.87-7.33 (3H, m)

PREPARATION 24

A mixture of 6-methyl-2-ureidobenzyl alcohol (1 g) and thionyl chloride (0.66 g) in methylene chloride (20 ml) was stirred for 2 hours at room temperature and evaporated in vacuo. The residue was washed with water and dried in a desiccator to give 6-methyl-2-ureidobenzyl chloride (0.66 g).

IR (Nujol): 3250, 1650, 1540 cm$^{-1}$
NMR (DMSO-d$_6$, δ): 4.83 (2H, s)

PREPARATION 25

The following compounds were prepared according to similar manner to those of Preparations 23 or 24.

(1) 2-Acetoxyacetamido-6-methylbenzyl chloride (2.7 g)
mp: 113° to 115° C.
IR (Nujol): 3260, 1740, 1660, 1600, 1540, 1220 cm$^{-1}$
NMR (CDCl$_3$, δ): 2.27 (3H, s), 2.45 (3H, s), 4.67 (2H, s), 4.77 (2H, s), 7.10 (1H, d, J=8 Hz), 7.30 (1H, t, J=8 Hz), 7.77 (1H, d, J=8 Hz), 8.27 (1H, br s)

(2) 2-Acetamidobenzyl chloride
mp: 95° to 101° C.
IR (Nujol): 3250, 1650, 1585, 1530 cm$^{-1}$
NMR (CDCl$_3$, δ): 2.21 (3H, s), 4.62 (2H, s), 7.0-8.0 (5H, m)

(3) 2-Ureidobenzyl chloride
mp: 153° to 156° C. (dec.)
IR (Nujol): 3480, 3330, 3255, 1640, 1575, 1530 cm$^{-1}$
NMR (DMSO-d$_6$, δ): 4.82 (2H, s), 5.00-5.80 (2H, broad s), 6.83-7.60 (3H, m), 7.77-8.30 (2H, m)

(4) 2-Methoxycarbonylaminobenzyl chloride
mp: 109° to 110° C.
IR (Nujol): 3280, 1685, 1585, 1525, 1300 cm$^{-1}$
NMR (CDCl$_3$, δ): 3.80 (3H, s), 4.60 (2H, s), 6.80-7.50 (4H, m), 7.78-7.95 (1H, m)

(5) 2-Acetoxymethylbenzyl chloride
 IR (film): 1720 cm$^{-1}$
 NMR (CDCl$_3$, δ): 2.08 (3H, s), 4.69 (2H, s), 5.26 (2H, s), 7.23–7.56 (4H, m)
(6) 3-Methoxymethoxybenzyl chloride
 This compound was used as a starting compound of Preparation 5-(7) without isolation.
(7) 2-Isonicotinamido-6-methylbenzyl chloride mono hydrochloride
 mp: 247° C. (dec.)
 IR (Nujol): 3240, 3050, 1650, 1590, 1530 cm$^{-1}$
 NMR (DMSO-d$_6$, δ): 2.46 (3H, s), 4.93 (2H, s), 7.10–7.46 (3H, m), 8.40–8.63 (2H, m), 9.0–9.26 (2H, m), 10.57 (1H, broad s), 10.90 (1H, broad s)
(8) 2-Methyl-6-propionamidobenzyl chloride
 mp: 105° to 109° C. (dec.)
 IR (Nujol): 3260, 1650, 1585, 1520 cm$^{-1}$
 NMR (DMSO-d$_6$, δ) 1.10 (3H, t, J=7 Hz), 2.16–2.60 (3H, q, J=7 Hz), 2.39 (3H, s), 4.80 (2H, s), 7.0–7.43 (3H, m), 9.53 (1H, s)
(9) 2-t-Butoxycarbonylaminoacetamido-6-methylbenzyl chloride
 mp: 70° to 73° C.
 IR (Nujol): 3350, 1695, 1680, 1580, 1495 cm$^{-1}$
 NMR (CDCl$_3$, δ): 1.47 (9H, s), 2.40 (3H, s), 3.95 (2H, d, J=6 Hz), 4.63 (2H, s), 5.33 (1H, t, J=6 Hz), 7.03 (1H, d, J=8 Hz), 7.23 (1H, t, J=8 Hz), 7.63 (1H, d, J=8 Hz), 8.33 (1H, broad s)
(10) 2-Formamido-6-methylbenzyl chloride
 mp: 126° to 129° C.
 IR (Nujol): 3200, 1650, 1525, 1280 cm$^{-1}$
 MASS: M+ 183
 NMR (CDCl$_3$, δ): 2.43 (3H, s), 4.64 (2H, s), 6.90–7.80 (4H, m), 8.40, 8.52 (1H, each s)
(11) 2-Benzyloxycarbonylamino-6-methylbenzyl chloride
 mp: 114° to 115° C.
 IR (Nujol): 3290, 1685, 1600, 1590, 1525 cm$^{-1}$
 NMR (CDCl$_3$, δ): 2.41 (3H, s), 4.65 (2H, s), 5.22 (2H, s), 6.83 (1H, br s), 6.99 (1H, b. dd, J=2 Hz, 8 Hz), 7.17 (1H, d, J=8 Hz), 7.39 (5H, s), 7.62 (1H, b, dd, J=2 Hz, 8 Hz)
(12) 2-Isopropoxycarbonylamino-6-methylbenzyl chloride
 mp: 141° to 146° C.
 IR (Nujol): 3275, 1685, 1600, 1585, 1525 cm$^{-1}$
 NMR (DMSO-d$_6$, δ): 1.23 (6H, d, J=6 Hz), 2.39 (3H, s), 4.83 (2H, s), 4.87 (1H, septet, J=6 Hz), 6.93–7.45 (3H, m), 8.89 (1H, s)
(13) 2-Ethoxycarbonylamino-6-methylbenzyl chloride
 mp: 112° to 113° C.
 IR (Nujol): 3260, 1680, 1590, 1580, 1520 cm$^{-1}$
 NMR (CDCl$_3$, δ): 1.31 (3H, t, J=7 Hz), 2.41 (3H, s), 4.25 (2H, q, J=7 Hz), 4.66 (2H, s), 6.75 (1H, br s), 7.01 (1H, d, J=8 Hz), 7.25 (1H, t, J=8 Hz), 7.62 (1H, d, J=8 Hz)
(14) 2-Methanesulfonylamino-6-methylbenzyl chloride
 mp: 156° to 158° C.
 IR (Nujol): 3230, 1590, 1320, 1140 cm$^{-1}$
 NMR (CDCl$_3$, δ): 2.46 (3H, s), 3.10 (3H, s), 4.76 (2H, s), 6.69 (1H, br s), 7.05–7.50 (3H, m)
(15) 3-Acetamido-2-methylbenzyl chloride
 IR (Nujol): 3260, 1645, 1590, 1525 cm$^{-1}$
 NMR (DMSO-d$_6$, δ): 2.05 (3H, s), 2.22 (3H, s), 4.80 (2H, s), 7.03–7.50 (3H, m), 9.37 (1H, br s)
(16) 4-Acetamido-2-methylbenzyl chloride
 mp: 143° to 145° C.
 IR (Nujol): 3310, 3190, 3125, 1665, 1610, 1540 cm$^{-1}$
 NMR (DMSO-d$_6$, δ): 2.02 (3H, s), 2.32 (3H, s), 4.69 (2H, s), 7.10–7.43 (3H, m), 9.83 (1H, br s)
(17) 6-Methyl-2-(3-methylureido)benzyl chloride
 mp: 172° to 175° C.
 IR (Nujol): 3325, 3260, 1620, 1565, 1260 cm$^{-1}$
 NMR (CDCl$_3$, δ): 2.43 (3H, s), 3.80 (3H, s), 4.67 (2H, s), 6.50–7.75 (5H, m)
(18) 2-Methoxycarbonylamino-6-methylbenzyl chloride
 mp: 125° to 127° C.
 IR (Nujol): 3275, 1680, 1595, 1580, 1520 cm$^{-1}$ 4.65 (2H, s), 6.55–7.00 (1H, broad s), 7.00 (1H, dd, J=2 Hz, 7.5 Hz), 7.25 (1H, t, J=7.5 Hz), 7.60 (1H, dd, J=7.5 Hz)
(19) 5-Acetamido-2-methylbenzyl chloride
 mp: 76° to 79° C.
 IR (Nujol): 3220, 1650, 1590, 1320, 1260 cm$^{-1}$
 NMR (CDCl$_3$, δ): 2.23 (3H, s), 2.37 (3H, s), 4.55 (2H, s), 7.00–7.60 (3H, m), 8.20–8.70 (1H, broad s)
(20) 2-t-Butoxycarbonylamino-6-methylbenzyl chloride
 mp: 75° to 76° C.
 IR (Nujol): 3355, 1685, 1600, 1582, 1510 cm$^{-1}$
 NMR (CLC$_3$δ): 1.52 (9H, s), 2.42 (3H, s), 4.67 (2H, s), 6.60 (1H, broad s), 7.0 (1H, d, J=7.5 Hz), 7.40 (1H, t, J=7.5 Hz), 7.80 (1H, d, J=7.5 Hz)
(21) 2-Acetamido-6-methylbenzyl chloride
 mp: 182° to 186° C. (dec.)
 IR (Nujol): 3360, 1650, 1600, 1530 cm$^{-1}$
 NMR (CDCl$_3$, δ): 2.07 (3H, s), 2.40 (3H, s), 4.80 (2H, s), 7.00–7.40 (3H, m), 9.53 (1H, br s)

PREPARATION 26

The following compound was prepared according to a similar manner to that of Preparation 4.
8(2-Cyanobenzyloxy)-2-methylimidazo[1,2-a]pyridine
 mp: 163° to 165° C. (recrystallized from ethyl acetate)
 IR (Nujol): 2220, 1280, 1100 cm$^{-1}$
 NMR (CDCl$_3$, δ): 2.46 (3H, s), 5.50 (2H, s), 6.30–6.76 (2H, m), 7.20–8.00 (6H, m)

PREPARATION 27

To a solution of 37% aqueous formaldehyde (0.95 g) in acetic acid (14 ml) was added dropwise 50% aqueous dimethylamine (1.05 g) with ice-cooling over a period of 10 minutes and the mixture was stirred for an additional 10 minutes. The mixture was heated at 50° C. for 2 hours after an addition of 8-(2-cyanobenzyloxy)-2-methylimidazo[1,2-a]pyridine (2.8 g) thereto and then evaporated in vacuo. The residue was basified with aqueous sodium hydroxide and extracted with methylene chloride. The extract was washed with water, dried over magnesium sulfate and evaporated in vacuo. The residual solid was recrystallized from a mixture of diethyl ether and n-hexane to give 8-(2-cyanobenzyloxy-3-dimethylaminomethyl-2-methylimidazo[1,2-a]pyridine.

mp: 168° to 170° C.
 IR (Nujol): 2220 cm$^{-1}$
 NMR (CDCl$_3$, δ): 2.20 (6H, s), 2.45 (3H, s), 3.60 (2H, s), 5.50 (2H, s), 6.40–6.80 (2H, m), 7.20–7.96 (5H, m)

PREPARATION 28

Methyl iodide (1.33 g) was added dropwise to a solution of 8-(2-cyanobenzyloxy)-3-dimethylaminomethyl-2-methylimidazo[1,2-a]pyridine (3 g) in the mixture of acetone (30 ml) and trichloromethane (30 ml) at room temperature and the mixture was stirred for 24 hours. The resulting precipitate was collected by filtration, washed with acetone, and dried in a desiccator to give 8-(2-cyanobenzyloxy)-2-methyl-3-trimethylammoniomethylimidazo[1,2-a]pyridine iodide.
 mp: 132° C. (dec.)

NMR (DMSO-d$_6$, δ): 2.46 (3H, s), 3.13 (9H, s), 5.03 (2H, s), 5.46 (2H, s), 6.83–7.16 (2H, m), 7.40–8.16 (4H, m), 8.56–8.60 (1H, m)

PREPARATION 29

The following compound was prepared according to a similar manner to that of Preparation 28.

8-(2-Acetamidobenzyloxy)-2-methyl-3-trimethylammoniomethylimidazo[1,2-a]pyridine iodide mp: 155° C. (dec.)

IR (Nujol): 3380 cm$^{-1}$

NMR (DMSO-d$_6$, δ): 2.50 (3H, s), 2.52 (3H, s), 3.13 (9H, s), 4.96 (2H, s), 5.28 (2H, s), 6.73–7.0 (2H, m), 7.05–7.70 (4H, m), 8.28–8.52 (1H, m), 9.53 (1H, s)

PREPARATION 30

To a solution of 3-(2-aminomethylbenzyloxy)-2-nitropyridine (1.73 g) and triethylamine (1.05 ml) in dichloromethane (35 ml) was added dropwise methyl chloroformate (0.63 g) at 5° C. and the mixture was stirred at the same temperature for 30 minutes. The reaction mixture was washed with a saturated aqueous sodium bicarbonate and water in turn, and dried over magnesium sulfate. The solvent was evaporated under reduced pressure and the resultant residue was triturated with diethyl ether to give 3-(2-methoxycarbonylaminomethylbenzyloxy)-2-nitropyridine (1.33 g).

mp: 99° to 101° C.

NMR (CDCl$_3$, δ): 3.63 (3H, s), 4.43 (2H, d, J=6 Hz), 5.30 (2H, s), 7.20–7.70 (7H, m), 8.00–8.20 (1H, m)

PREPARATION 31

A solution of 2-nitro-3-(2-phthalimidomethylbenzyloxy)pyridine (2.71 g) and hydrazine hydrate (1.05 g) in ethanol (54 ml) was refluxed for 1.5 hours. After cooling, precipitates were filtered off, and the filtrate was evaporated under reduced pressure. The resultant residue was dissolved in diethyl ether and insoluble materials were filtered off. The solvent was evaporated under reduced pressure to give 3-(2-aminomethylbenzyloxy)-2-nitropyridine (1.75 g).

IR (film): 1590, 1455, 1380, 1280 cm$^{-1}$

NMR (CDCl$_3$, δ): 2.64 (2H, bs), 3.97 (2H, s), 5.37 (2H, s), 7.00–8.10 (7H, m)

PREPARATION 32

A solution of 3-(2-chloromethylbenzyloxy)-2-nitropyridine (4.09 g) and potassium phthalimide (2.99 g) in N,N-dimethylformamide (41 ml) was stirred at 50° C. for 9.5 hours. The reaction mixture was poured into water (200 ml) and extracted twice with ethyl acetate (250 ml). The combined extract was washed with water and dried over magnesium sulfate. The solvent was evaporated under reduced pressure and the resultant residue was recrystallized from ethyl acetate to give 2-nitro-3-(2-phthalimidomethylbenzyloxy)pyridine (2.7 g).

mp: 163° to 165° C.

IR (Nujol): 1710, 1530, 1285, 1270, 1110 cm$^{-1}$

NMR (DMSO-d$_6$, δ): 4.87 and 4.93 (2H, each s), 5.40 and 5.53 (2H each s), 7.30–8.20 (11H, m)

PREPARATION 33

To a solution of 3-(2-hydroxymethylbenzyloxy)-2-nitropyridine (4.09 g) in dichloromethane (40 ml) was added thionyl chloride (0.24 ml) and the mixture was stirred at room temperature for 2 hours. The solvent was evaporated under reduced pressure to give 3-(2-chloromethylbenzyloxy)-2-nitropyridine (4.10 g).

mp: 85° to 88° C.

IR (Nujol): 1530, 1310, 1250 cm$^{-1}$

NMR (CDCl$_3$, δ): 4.73 (2H, s), 5.17 (2H, s), 7.23–7.72 (6H, m), 8.00–8.23 (1H, m)

PREPARATION 34

A solution of 3-(2-acetoxymethylbenzyloxy)-2-nitropyridine (7.8 g) in methanol (39 ml) and 1N aqueous sodium hydroxide (23 ml) was stirred at room temperature for 0.5 hours. To the mixture was added water (50 ml) and the precipitates were collected by filtration to give 3-(2-hydroxymethylbenzyloxy)-2-nitropyridine (4.18 g).

mp: 99° to 100° C.

IR (Nujol): 3200, 1600, 1520, 1275 cm$^{-1}$

NMR (CDCl$_3$, δ): 2.23 (1H, t, J=5 Hz), 4.80 (2H, d, J=5 Hz), 5.40 (2H, s), 7.20–7.83 (6H, m), 8.00–8.20 (1H, m)

PREPARATION 35

A mixture of 2,6-dinitrobenzyl acetate (0.56 g), platinic oxide (73 mg), acetic acid (6 ml) and acetic anhydride (6 ml) was stirred in hydrogen gas at room temperature until the theoretical amount of hydrogen gas had been absorbed. The catalyst was removed by filtration and the filtrate was evaporated under reduced pressure. The resultant residue was subjected to column chromatography on silica gel (18 g) and eluted with a mixture of chloroform and methanol (100:3) to give 2,6-di(acetamido)benzyl acetate (0.45 g).

mp: 222° to 223° C.

IR (Nujol): 3260, 1725, 1650, 1220 cm$^{-1}$

NMR (DMSO-d$_6$, δ): 1.97 (3H, s), 2.03 (6H, s), 5.03 (2H, s), 7.13–7.32 (3H, m), 9.40 (2H, bs).

PREPARATION 36

To a solution of 2,6-di(acetamido)benzyl acetate (0.97 g) in methanol (70 ml) was added an aqueous solution (1.8 ml) of potassium carbonate (608 mg) and the mixture was stirred at room temperature for 1 hour. After methanol was evaporated under reduced pressure, the resultant residue was subjected to column chromatography on silica gel (18 g) and eluted with a mixture of chloroform and methanol (20:1) to give 2,6-di(acetamido)benzyl alcohol (0.67 g).

mp: 161° to 162° C.

IR (Nujol): 3270, 1650, 1380 cm$^{-1}$

NMR (DMSO-d$_6$, δ): 2.05 (6H, s) 4.50 (2H, d, J=5 Hz), 5.30 (1H, t, J=5 Hz), 7.17–7.53 (3H, m), 9.47 (2H, bs).

PREPARATION 37

The following compounds were prepared according to similar manners to those of Preparations 16 to 21.

(1) N-(2-Hydroxymethyl-3-methylphenyl)-N-methylmethanesulfonamide mp: 90° to 96° C.

NMR (CDCl$_3$, δ): 2.53 (3H, s), 2.96 (3H, s), 3.29 (3H, s), 3.35–3.62 (1H, b), 4.56 (1H, d, J=12 Hz), 4.93 (1H, d, J=12 Hz), 6.98–7.42 (3H, m).

(2) 1-2-(Hydroxymethyl-3-methylphenyl)-1-methylurea

IR (film): 3300 (broad), 1640, 1580 cm$^{-1}$

NMR (CDCl$_3$, δ): 2.46 (3H, s), 3.16 (3H, s), 4.57 (2H, s), 6.86–7.26 (3H, m)

MASS: M+=194

(3) t-Buthyl N-2-(hydroxymethyl-3-methylphenyl)-N-methylcarbamate

IR (film): 3450, 1690, 1595, 1580 cm$^{-1}$
NMR (CDCl$_3$, δ): 1.53 (9H, s), 2.50 (3H, s, 3.20 (3H, s), 4.55 (2H,d, J=6 Hz), 6.90-7.43 (3H, m)

PREPARATION 38

The following compounds were prepared according to similar manners to those of Preparations 23 or 24.
(1) N-(2-Chloromethyl-3-methylphenyl)-N-methylmethanesulfonamide
mp: 78° to 80° C.
IR (Nujol): 1595, 1585, 1330, 1150 cm$^{-1}$
NMR (CDCl$_3$, δ): 2.50 (3H, s), 3.00 (3H, s), 3.32 (3H, s), 4.58 (1H, bd, J=12 Hz), 5.20 (1H, bd, J=12 Hz), 7.03-7.53 (3H, m)
(2) 1-(2-Chloromethyl-3-methylphenyl)-1-methylurea
mp: 194° to 196° C. (dec.)
NMR (CDCl$_3$, δ): 2.51 (3H, s), 3.41 (3H, s), 4.57 (2H, s), 6.90-7.56 (3H, m), 8.63 (2H, bs)
(3) t-Butyl N-(2-chloromethyl-3-methylphenyl)-N-methylcarbamate
IR (film): 1700, 1595 cm$^{-1}$
NMR (CDCl$_3$, δ): 1.40 (9H, s), 2.46 (3H, s), 3.22 (3H, s), 4.54 (1H, d, J=1 Hz), 4.68 (1H, d, J=11 Hz) 6.93-7.40 (3H, m)

PREPARATION 39

The following compounds were prepared according to a similar manner to that of Preparation 4.
(1) 3-(2-Methoxycarbonylamino-6-methylbenzyloxy)-6-methyl-2-nitoropyridine.
mp: 113° to 117° C.
IR (Nujol): 3250, 1700, 1605, 1520 cm$^{-1}$
NMR (CDCl$_3$, δ): 2.39 (3H, s), 2.53 (3H, s), 3.75 (3H, s), 5.21 (2H, s), 7.03 (1H, d, J=8 Hz), 7.22-7.75 (5H, m)
(2) 3-[6-Methyl-2-(N-methyl-N-mesylamino)benzyloxy]-2-nitropyridine
IR (film): 1670, 1598, 1560, 1540, 1340, 1145 cm$^{-1}$
NMR (CDCl$_3$, δ): 2.43 (3H, s), 2.93 (3H, s), 3.23 (3H, s), 5.13 (1H, d, J=12 Hz), 5.72 (1H, d, J=12 Hz), 7.13-7.43 (3H, m), 7.57 (1H, dd, J=5, 9 Hz), 7.83 (1H, dd, J=2, 9 Hz), 8.12 (1H, dd, J=2, 5 Hz)
(3) 3-[6-Methyl-2-(1-methylureido)benzyloxy]-2-nitropyridine
mp: 177° to 179° C.
IR (Nujol): 3375, 3190, 3055, 1660, 1605, 1560, 1540 cm$^{-1}$
NMR (DMSO-d$_6$, δ): 2.36 (3H, s), 3.02 (3H, z) 5.23 (2H, s), 5.63 (2H, s), 7.06-7.53 (3H, m), 7.75-7.96 (1H, m), 8.10-8.30 (2H, m)
(4) 3-[6-Methyl-2-(N-methyl-N-t-butoxycarbonylamino)benzyloxy]-2-nitropyridine
mp: 115° to 117° C.
IR (Nujol): 1690, 1582, 1570, 1538 cm$^{-1}$
NMR (CDCl$_3$, δ): 1.37 (9H, s), 2.41 (3H, s), 3.15 (3H, s), 5.16 (2H, s), 6.98-7.80 (5H, m), 8.13 (1H, dd, J=2, 4.5 Hz)
(5) 3-(2-Acetoxymethylbenzyloxy)-2-nitropyridine
IR (film): 1735, 1600, 1560, 1540 cm$^{-1}$
NMR (CDCl$_3$, δ): 2.06 (3H, s), 5.23 (2H, s), 5.35 (2H, s), 7.26-7.80 (6H, m), 8.12 (1H, dd, J=2, 6 Hz)

PREPARATION 40

The following compounds were prepared according to a similar manner to that of Preparation 10.
(1) 2-Amino-3-(2-methoxycarbonylamino-6-methylbenzyloxy)-6-methylpyridine
mp: 135° to 136° C.
IR (Nujol): 3440, 3400, 3270, 3135, 1730, 1690, 1620, 1600, 1585 cm$^{-1}$
NMR (CDCl$_3$, δ): 2.32 (3H, s), 2.36 (3H, s), 3.73 (3H, s), 4.64 (2H, bs), 5.02 (2H, s), 6.46 (1H, d, J=8 Hz), 6.90-7.11 (2H, m), 7.20-7.43 (2H, m), 7.71 (1H, d, J=7.5 Hz)
(2) 2-Amino-3-[6-methyl-2-(N-methyl-N-mesylamino)benzyloxy]-pyridine.
mp: 184° to 186° C.
IR (Nujol): 3490, 3290, 3160, 1630, 1600, 1563 cm$^{-1}$
NMR (CDCl$_3$, δ): 2.43 (3H, s), 2.93 (3H, s), 3.22 (3H, s), 4.65 (2H, bs), 4.76-5.63 (2H, m), 6.64 (1H, dd, J=5, 7.5 Hz), 7.15 (1H, dd, J=2, 7.5 Hz), 7.20-7.50 (3H, m), 7.70 (1H, dd, J=2, 5 Hz)
(3) 2-Amino-3-[6-methyl-2-(1-methylureido)benzyloxy]pyridine
mp: 140° to 144° C.
IR (Nujol): 3475, 3405, 3300, 3150, 1655, 1625, 1595, 1575 cm$^{-1}$
NMR (CDCl$_3$, δ): 2.48 (3H, s), 3.20 (3H, s), 4.59 (4H, bs), 5.03 (2H, s), 6.65 (1H, dd, J=5,8 Hz), 7.12 (1H, dd, J=2, 8 Hz), 7.15-7.48 (3H, m), 7.70 (1H, d, d, J=2, 5 Hz)
(4) 2-Amino-3-[6-methyl-2-(N-methyl-N-t-butoxycarbonylamino)-benzyloxy]pyridine
mp: 127° to 128° C.
IR (Nujol): 3460, 3300, 3175, 1690, 1630, 1600, 1590, 1570 cm$^{-1}$
NMR (CDCl$_3$, δ): 1.38 (9H, s), 2.42 (3H, s), 3.16 (3H, s), 4.66 (2H, bs), 4.97 (2H, s), 6.65 (1H, dd, J=5, 8 Hz), 7.00-7.46 (4H, m) 7.71 (1H, d, J=5 Hz)
(5) 2-Amino-3-(2-methoxycarbonylaminomethylbenzyloxy) pyridine
mp: 99° to 101° C.
IR (Nujol): 3465, 3325, 3280, 1680, 1520 cm$^{-1}$
NMR (CDCl$_3$, δ): 3.65 (3H, s), 4.47 (2H, d, J=6 Hz), 4.70 (2H, bs), 5.12 (2H, s), 5.43 (1H, bs), 6.50-7.77 (7H, m)

PREPARATION 41

A solution of 2-amino-3-methoxymethoxypyridine (7.5 g) and 3-mesyloxy-5-hexyn-2-one (10.18 g) in ethanol (150 ml) was refluxed for 46.5 hours and then evaporated in vacuo. To the residue was added 20% sulfuric acid (75 ml) and the mixture was stirred for 5 hours at room temperature. The mixture was made alkaline with sodium bicarbonate and extracted with chloroform. The extract was washed with brine, dried over magnesium sulfate, and evaporated in vacuo. The residue was purified by column chromatography on silica gel (30 g) with chloroform and then a mixture of chloroform and methanol (30:1 to 20:1) as eluents. The eluates were evaporated in vacuo and the residue was recrystallized from a mixture of ethyl acetate and n-hexane to give 8-hydroxy-2-methyl-3-(2-propynyl)imidazo[1,2-a]pyridine (1.93 g).
mp: 175° to 177° C.
NMR (CDCl$_3$, δ): 2.03 (1H, t, J=3 Hz), 2.45(3H, s), 3.73 (2H, d, J=3 Hz), 6.70-6.90 (2H, m), 7.57-7.76 (1H, m), 11.29 (1H, s)

EXAMPLE 1

A mixture of 8-hydroxy-2-methyl-3-(2-propynyl) imidazo-[1,2-a]pyridine (0.571 g) and potassium carbonate (0.424 g) in N,N-dimethylformamide (11.5 ml) was stirred at room temperature for 20 minutes under a nitrogen atmosphere and then 6-methyl-2-ureidobenzyl chloride (0.6 g) was added. After being stirred for 2.5 hours. The mixture was poured into water and the resulting precipitates were collected by filtration. The crude product was purified by column chromatography on silica gel (25 g) with a mixture of chloroform and methanol (100:1 to 100:4) as eluents to give 2-methyl-8-(6-methyl-2-ureidobenzyloxy)-3-(2-propynyl-)imidazo[1,2-a]pyridine (0.13 g).

mp: 197° to 199° C. (dec.)

IR (Nujol): 3380, 3270, 3240, 3170, 1660, 1590, 1540, 1090 cm$^{-1}$

NMR (DMSO-d$_6$, δ): 2.30 (3H, s), 2.35 (3H, s), 2.97 (1H, t, J=3 Hz), 3.95 (2H, d, J=3 Hz), 5.23 (2H, s), 6.10 (2H, s), 6.70–7.43 (4H, m), 7.60–8.10 (2H, m), 8.20 (1H, s)

EXAMPLE 2

The following compounds were prepared according to a similar manner to that of Example 1.

(1) 8-(2-Acetoxymethylbenzyloxy)-2-methyl-3-(2-propynyl)imidazo[1,2-a]pyridine mp: 134° to 135° C.

IR (Nujol): 3280, 1715 cm$^{-1}$

NMR (CDCl$_3$, δ): 2.06 (3H, s), 2.0–2.13 (1H, t, J=3 Hz), 2.46 (3H, s), 3.78 (2H, d, J=3 Hz), 5.27 (2H, s), 5.41 (2H, s), 6.40–6.86 (2H, m), 7.26–7.63 (4H, m), 7.73 (1H, dd, J=2 Hz, 6 Hz)

(2) 8-(2-Formamido-6-methylbenzyloxy)-2-methyl-3-(2-propynyl)imidazo[1,2-a]pyridine mp: 189° to 190° C. (recrystallized from ethanol)

IR (Nujol): 3200, 1685, 1605, 1585, 1540, 1280 cm$^{-1}$

Mass: M+ $b$ 333

NMR (CDCl$_3$, δ): 2.08 (1H, t, J=3 Hz), 2.45, 2.50, 2.52, 2.57 (6H, each s), 3.75 (2H, d, J=3 Hz), 5.28, 5.33 (2H, each s), 6.55–7.30, 7.65–8.10 (6H, m), 8.40–8.63 (1H, m), 10.70–11.20 (1H, broad m)

(3) 8-(2-Ethoxycarbonylamino-6-methylbenzyloxy)-2-methyl-3-(2-propynyl)imidazo[1,2-a]pyridine mp: 175° to 177° C. (recrystallized from a mixture of ethyl acetate and n-hexane)

IR (Nujol): 3280, 1710, 1540 cm$^{-1}$

NMR (CDCl$_3$, δ): 1.29 (3H, t, J=6 Hz), 2.06 (1H, t, J=3 Hz), 2.47 (3H, s), 2.50 (3H, s), 3.76 (2H, d, J=3 Hz), 4.20 (2H, q, J=6 Hz), 5.38 (2H, s), 6.60–6.80 (2H, m), 6.92 (1H, d, J=7.5 Hz), 7.21 (1H, t, J=7.5 Hz), 7.63 (1H, d, J=7.5 Hz), 7.70–7.83 (1H, m), 8.89 (1H, br s)

(4) 8-(2-Methanesulfonylamino-6-methylbenzyloxy)-2-methyl-3-(2-propynyl)imidazo[1,2-a]pyridine mp: 135° to 136° C. (recrystallized from a mixture of ethyl acetate and n-hexane)

IR (Nujol): 3275, 1540, 1323, 1145 cm$^{-1}$

NMR (CDCl$_3$, δ): 2.06 (1H, t, J=3 Hz), 2.53 (6H, s), 2.93 (3H, s), 3.76 (2H, d, J=3 Hz), 5.47 (2H, s), 6.62–6.90 (2H, m), 6.96–7.33 (1H, br s), 7.03 (1H, b.d, J=7 Hz), 7.22 (1H, t, J=7 Hz), 7.52 (1H, dd, J=7 Hz), 7.83 (1H, dd, J=1.5 Hz, 6 Hz)

Analysis Calcd. for C$_{20}$H$_{21}$N$_3$O$_3$S: C 62.64, H 5.52, N 10.96, Found: C 62.72, H 5.57, N 10.16.

(5) 8-(3-Acetamido-2-methylbenzyloxy)-2-methyl-3-(2-propynyl)imidazo[1,2-a]pyridine mp: 207° to 208° C. (recrystallized form ethanol and diisopropyl ether)

IR (Nujol): 3200, 1635, 1540 cm$^{-1}$

NMR (DMSO-d$_6$, δ): 2.03 (3H, s), 2.17 (3H, s), 2.30 (3H, s), 2.90 (1H, t, J=3 Hz), 3.86 (2H, d, J=3 Hz), 5.21 (2H, s), 6.63–6.86 (2H, m), 6.96–7.36 (3H, m), 7.80 (1H, dd, J=3 Hz, 5 Hz), 9.26 (1H, s)

Analysis Calcd. for C$_{21}$H$_{21}$N$_3$O$_2$: C 72.60, H 6.09, N 12.10, Found: C 72.76, H 5.83, N 12.17.

(6) 2-Methyl-8-[6-methyl-2-(3-methylureido)benzyloxy]-3-(2-propynyl)imidazo[1,2-a]pyridine mp: 214° to 215° C. (dec.) (recrystallized from ethanol)

IR (Nujol): 3400, 3290, 1695, 1605 cm$^{-1}$

NMR (DMSO-d$_6$, δ): 2.30 (3H, s), 2.31 (3H, s), 2.62 (3H, d, J=5 Hz), 2.93 (1H, t, J=3 Hz), 3.89 (2H, d, J=3 Hz), 5.13 (2H, s), 6.45 (1H, q, J=5 Hz), 6.70–6.93 (3H, m), 7.14 (1H, t, J=7.5 Hz), 7.57 (1H, broad d, J=7.5 Hz), 7.85 (1H, t, J=4.5 Hz), 8.03 (1H, s)

(7) 8-(5-Acetamido-2-methylbenzyloxy)-2-methyl-3-(2-propynyl)imidazo[1,2-a]pyridine mp: 235° to 237° C. (dec.) (recrystallized from ethanol)

IR (Nujol): 3270, 1670, 1595, 1535, 1490 cm$^{-1}$

NMR (DMSO-d$_6$, δ): 2.00 (3H, s), 2.28 (3H, s), 2.30 (3H, s), 2.90 (1H, t, J=3 Hz), 3.87 (2H, d, J=3 Hz), 5.16 (2H, s), 6.57–6.88 (2H, m), 7.06 (1H, d, J=9 Hz), 7.35–7.56 (2H, m), 7.80 (1H, dd, J2 Hz, 6 Hz), 9.78 (1H, s)

(8) 8-(2-t-Butoxycarbonylamino-6-methylbenzyloxy)-2-methyl-3-(2-propynyl)imidazo[1,2-a]pyridine IR (CHC$_3$): 3400, 3300, 1710, 1580, 1535, 1370, 1270, 1150 cm$^{-1}$ NMR (CDCl$_3$, δ): 1.47 (9H, s), 2.05 (1H, t, J=3 Hz), 2.42 (3H, s), 2.47 (3H, s), 3.75 (2H, d, J=3 Hz), 5.35 (2H, s), 6.55–6.70 (2H, m), 6.88 (1H, d, J=7.5 Hz), 7.15 (1H, t, J=7.5 Hz), 7.51 (1H, d, J=7.5 Hz), 7.71 (1H, dd, J=3 Hz, 5 Hz), 7.98 (1H, broad s)

(9) 8-(2-Acetamido-6-methylbenzyloxy)-2-methyl-3-(2-propynyl)imidazo[1,2-a]pyridine mp: 194° to 195° C. (recrystallized from a mixture of ethanol and diisopropyl ether)

IR (Nujol): 3340, 3270, 1683, 1603, 1585, 1280 cm$^{-1}$

NMR (CDCl$_3$, δ): 2.07 (1H, t, J=3 Hz), 2.17 (3H, s), 2.43 (6H, s), 3.76 (2H, d, J=3 Hz), 5.30 (2H, s), 6.63–6.73 (2H, m), 6.90 (1H, bd, J=7.5 Hz), 7.17 (1H, t, J=7.5 Hz), 7.60–7.83 (2H, m), 9.07 (1H, br s)

Analysis Calcd. for C$_{21}$H$_{21}$N$_3$O$_2$: C 72.60, H 6.09, N 12.09, Found: C 73.10, H 6.21, N 11.72.

EXAMPLE 3

A mixture of 2-amino-3-(2-methoxycarbonylamino-6-methylbenzyloxy)pyridine (4.22 g) and 3-mesyloxy-5-hexyn-2-one (2.74 g) in ethanol (42 ml) was refluxed for 62 hours and then evaporated in vacuo. To the residue was added and aqueous solution of sodium bicarbonate and the insoluble material was collected by filtration. The crude product was purified by column chromatography on silica gel (150 g) with methylene chloride and then a mixture of methylene chloride and acetonitrile (10:1) as eluents to afford a solid, which was recrystallized from a mixture of ethyl acetate and cyclohexane to give 8-(2-methoxycarbonylamino-6-methylbenzyloxy)-2-methyl-3-(2-propynyl)imidazo[1,2-a]pyridine.

mp: 179° to 180° C.

analysis Calcd. for C$_{21}$H$_{21}$N$_3$O$_3$: C 69.40, H 5.82, N 11.56, Found: C 69.79, H 5.76, N 11.68.

EXAMPLE 4

The following compounds were prepared according to a similar manner to that of Example 3.

(1) 2-Methyl-3-(2-propynyl)-8-(2-trifluoromethylbenzyloxy)imidazo[1,2-a]pyridine mp: 146° to 147° C. (recrystallized from a mixture of ethyl acetate and n-hexane)

IR (Nujol): 3290 cm$^{-1}$

NMR (CDCl$_3$, δ): 2.06 (1H, t, J=3 Hz), 2.47 (3H, s), 3.76 (2H, d, J=3 Hz), 5.53 (2H, s), 6.37 (1H, d, J=8 Hz), 6.63 (1H, t, J=7 Hz), 7.23–8.0 (5H, m)

(2) 8-(2-Acetamidobenzyloxy)-2-methyl-3-(2-propynyl)imidazo[1,2-a]pyridine mp: 193° to 194° C. (recrystallized from isopropyl alcohol)

IR (Nujol): 3300, 1685, 1585, 1540, 1525 cm$^{-1}$

NMR (DMSO-d$_6$, δ): 2.08 (3H, s), 2.35 (3H, s), 2.93 (1H, t, J=3 Hz), 3.92 (2H, d, J=3 Hz), 5.30 (2H, s), 6.70 (1H, dd, J=1.5 Hz, 6 Hz), 6.83 (1H, t, J=6 Hz), 7.08–7.70 (4H, m), 7.93 (1H, dd, J=1.5 Hz, 6 Hz), 9.63 (1H, s)

Analysis Calcd. for C$_{20}$H$_{19}$N$_3$O$_2$: C 72.05, H 5.74, N 12.60, Found: C 71.97, H 5.46, N 12.54.

(3) 2-Methyl-3-(2-propynyl)-8-(2-ureidobenzyloxy)imidazo[1,2-a]pyridine mp: 210° to 213° C. (dec.)

IR (Nujol): 3460, 3220, 1700, 1585, 1540 cm$^{-1}$

NMR (DMSO-d$_6$, δ): 2.36 (3H, s), 2.95 (1H, t, J=3 Hz), 3.95 (2H, d, J=3 Hz), 5.24 (2H, s), 6.20 (2H, broad s), 6.70–7.47 (5H, m), 7.80–8.00 (2H, m), 8.22 (1H, broad s)

(4) 8-(2-Methoxycarbonylaminobenzyloxy)-2-methyl-3-(2-propynyl)imidazo[1,2-a]pyridine mp: 146° to 147° C. (recrystallized from ethyl acetate)

IR (Nujol): 3310, 1720, 1590, 1540 cm$^{-1}$

NMR (CDCl$_3$, δ): 2.07 (1H, t, J=3 Hz), 2.47 (3H, s), 3.77 (3H, s), 3.73–3.87 (2H), 5.34 (2H, s), 6.60–6.87 (2H, m), 6.97–7.52 (3H, m), 7.73–8.12 (2H, m), 9.10 (1H, broad s)

(5) 8-(2-Formamidobenzyloxy)-2-methyl-3-(2-propynyl)imidazo[1,2-a]pyridine mp: 190° to 191° C. (recrystallized from ethyl acetate)

IR (Nujol): 3280, 1690, 1590, 1540, 1285 cm$^{-1}$

NMR (CDCl$_3$, δ): 2.10 (1H, t, J=3 Hz), 2.47, 2.57 (3H, each s), 3.77 (2H, d, J=3 Hz), 5.25 (2H, s), 6.63–7.57, 7.73–7.93, 8.23–8.45 (7H, m), 8.57–8.77 (1H, m), 11.10 (1H, broad m)

Analysis Calcd. for C$_{19}$H$_{17}$N$_3$O$_2$: C 71.46, H 5.37, N 13.16, Found: C 71.68, H 5.39, N 13.22.

(6) 8-(2-Carbamoylbenzyloxy)-2-methyl-3-(2-propynyl)imidazo1,2-a]pyridine mp: 188° to 190° C. (recrystallized from isopropanol)

IR (Nujol): 3425, 3300, 3140, 1660, 1600, 1540 cm$^{-1}$

NMR (DMSO-d$_6$, δ): 2.33 (3H, s), 2.94 (1H, t, J=3 Hz), 3.94 (2H, d, J=3 Hz), 5.51 (2H, s), 6.55–7.0 (2H, m), 7.30–8.06 (7H, m)

Analysis Calcd for C$_{19}$H$_{17}$N$_3$O: C 71.46, H 5.37, N 13.16, Found: C 71.61, H 5.33, N 12.89.

(7) 8-(2-Methoxymethoxybenzyloxy)-2-methyl-3-(2-propynyl)imidazo[1,2-a]pyridine mp: 122° to 123° C. (recrystallized from a mixture of ethyl acetate and n-hexane)

IR (Nujol): 3150, 2100, 1600, 1530 cm$^{-1}$

NMR (CDCl$_3$, δ): 2.05 (1H, t, J=3 Hz), 2.46 (3H, s), 3.50 (3H, s), 3.75 (2H, d, J=3 Hz), 5.24 (2H, s), 5.40 (2H, s), 6.46 (1H, dd, J=1.5 Hz, 7 Hz), 6.65 (1H, t, J=7 Hz), 6.86–7.40 (3H, m), 7.46–7.63 (1H, m), 7.68 (1H, dd, J=1.5 Hz, 7 Hz)

Analysis Calcd. for C$_{20}$H$_{20}$N$_2$O$_3$: C 71.41, H 5.99, N 8.33, Found: C 71.82, H 6.34, N 8.23.

(8) 8-(4-Hydroxymethylbenzyloxy)-2-methyl-3-(2-propynyl)imidazo[1,2-a]pyridine mp: 198° to 200° C.

IR (Nujol): 3220, 3150, 1535, 1280 cm$^{-1}$

NMR (DMSO-d$_6$, δ) 2.30 (3H, s), 2.90 (1H, t, J=3 Hz), 3.87 (2H, d, J=3 Hz), 4.47 (2H, d, J=6 Hz), 5.12 (1H, t, J=6 Hz), 5.20 (2H, s), 6.53–6.87 (2H, m), 7.27 (2H, d, J=8 Hz), 7.39 (2H, d, J=8 Hz), 7.70–7.87 (1H, m)

(9) 8-(4-Ethoxycarbonylbenzyloxy)-2-methyl-3-(2-propynyl)imidazo[1,2-a]pyridine mp: 152° to 155° C. (recrystallized from ethanol)

IR (Nujol): 3300, 1710, 1610, 1540, 1280 cm$^{-1}$

NMR (CDCl$_3$, δ): 1.40 (3H, t, J=7.5 Hz), 2.07 (1H, t, J=3 Hz), 2.47 (3H, s), 3.78 (2H, d, J=3 Hz), 4.38 (2H, q, J=7.5 Hz), 5.40 (2H, s), 6.42 (1H, d, J=7.5 Hz), 6.67 (1H, t, J=7.5 Hz), 7.58 (2H, d, J=8 Hz), 7.75 (1H, d, J=7.5 Hz), 8.07 (2H, d, J=8 Hz)

(10) 8-(4-Carbamoylbenzyloxy)-2-methyl-3-(2-propynyl)imidazo[1,2-a]pyridine mp: 242° to 243° C. (recrystallized from a mixture of chloroform and methanol)

IR (Nujol): 3350, 3290, 3170, 1645, 1610, 1280 cm$^{-1}$

NMR (DMSO-d$_6$, δ): 2.33 (3H, s), 2.93 (1H, t, J=3 Hz), 3.90 (2H, d, J=3 Hz), 5.33 (2H, s), 6.60–6.90 (2H, m), 7.30 (1H, br s), 7.51 (2H, d, J=8 Hz), 7.73–8.00 (2H, m), 7.88 (2H, d, J=8 Hz)

Analysis Calcd. for C$_{19}$H$_{17}$N$_3$O$_2$: C 71.46, H 5.36, N 13.16, Found: C 71.87, H 5.60, N 13.02.

(11) 8-(3-Hydroxybenzyloxy)-2-methyl-3-(2-propynyl)imidazo[1,2-a]pyridine mp: 219° to 221° C. (recrystallized from a mixture of ethanol and chloroform)

IR (Nujol): 3270, 1585, 1540, 1290 cm$^{-1}$

NMR (DMSO-d$_6$, δ): 2.33 (3H, s), 2.90 (1H, t, J=3 Hz), 3.90 (2H, d, J=3 Hz), 5.20 (2H, s), 6.60–7.37 (6H, m), 7.77–8.00 (1H, m), 9.40 (1H, s)

Analysis Calcd. for C$_{18}$H$_{16}$N$_2$O$_2$: C 73.95, H 5.52, N 9.58, Found: C 73.86, H 5.71, N 9.21.

(12) 8-(2-Isonicotinamido-6-methylbenzyloxy)-2-methyl-3-(2-propynyl)imidazo[1,2-a]pyridine mp: 174° to 175° C. (recrystallized from ethyl acetate and n-hexane)

IR (Nujol): 3375, 3245, 1680, 1600, 1540, 1520 cm$^{-1}$

NMR (CDCl$_3$, δ): 2.10 (1H, t, J=3 Hz), 2.34 (3H, s), 2.49 (3H, s), 3.76 (2H, d, J=3 Hz), 5.45 (2H, s), 6.63–6.86 (2H, m), 7.07 (1H, d, J=8 Hz), 7.33 (1H, t, J=8 Hz), 7.75–8.00 (4H, m), 8.56–8.70 (2H, m), 9.90 (1H, broad s)

Analysis Calcd for C$_{25}$H$_{22}$N$_4$O$_2$: C 73.15, H 5.40, N 13.65, Found: C 74.48, H 5.38, N 13.70.

(13) 2-Methyl-8-(2-methyl-6-propionamidobenzyloxy)-3-(2-propynyl)imidazo[1,2-a]pyridine mp: 164° to 165° C. (recrystallized form ethyl acetate)

IR (Nujol): 3310, 1690, 1600, 1585, 1540 cm$^{-1}$

NMR (DMSO-d$_6$, δ): 1.05 (3H, t, J=7.5 Hz), 2.31 (3H, s), 2.40 (3H, s), 2.20–2.56 (2H, q, J=7.5 Hz), 2.94 (1H, t, J=3 Hz), 3.91 (2H, d, J=3 Hz), 5.23 (2H, s), 6.73–7.30 (2H, m), 7.03–7.50 (3H, m), 7.95 (1H, dd, J=3.6 Hz), 9.60 (1H, s)

Analysis Calcd for C$_{22}$H$_{23}$N$_3$O$_2$: C 73.11, H 6.41, N 11.63, Found: C 73.14, H 6.37, N 14.49.

(14) 8-[2,6-Bis(hydroxymethyl)benzyloxy]-2-methyl-3-(2-propynyl)imidazo[1,2-a]pyridine mp: 185° to 187° C. (recrystallized from ethyl acetate)

IR (Nujol): 3300, 1543, 1290, 1090 cm$^{-1}$

NMR (DMSO-d$_6$, δ): 2.28 (3H, s), 2.95 (1H, t, J=3 Hz), 3.92 (2H, d, J=3 Hz), 4.63 (4H, d, J=5 Hz), 5.20 (2H, t, J=5 Hz), 5.33 (2H, s), 6.80–7.03 (2H, m), 7.40 (3H, s), 7.87–8.00 (1H, m)

(15) 8-(2-Hydroxymethyl-6-methylbenzyloxy)-2-methyl-3-(2-propynyl)imidazo[1,2-a]pyridine mp: 59° to 61° C.

IR (Nujol): 3200, 1540, 1285 cm$^{-1}$

NMR (CDCl$_3$, δ): 2.08 (1H, t, J=3 Hz), 2.40 (3H, s), 2.47 (3H, s), 3.77 (2H, d, J=3 Hz), 4.73 (2H, s), 5.41 (2H, s), 6.67–6.93 (2H, m), 7.10–7.40 (3H, m), 7.73–7.87 (1H, m)

(16) 8-(2-t-Butoxycarbonylaminoacetamido-6-methylbenzyloxy)-2-methyl-3-(2-propynyl)imidazo[1,2a]pyridine NMR (CDCl$_3$, δ): 1.30 (9H, s), 2.08 (1H, t, J=3 Hz), 2.47 (6H, s), 3.78 (2H, d, J=3 Hz), 4.03 (2H, d, J=6 Hz), 5.42 (2H, s), 6.70–7.40 (5H, m), 7.77–8.10 (2H, m), 9.67 (1H, broad s)

(17) 8-(2-Benzyloxycarbonylamino-6-methylbenzyloxy)-2-methyl-3-(2-propynyl)imidazo[1,2-a]pyridine mp: 160° to 161° C. (recrystallized from a mixture of ethyl acetate and diisopropyl ether)

IR (Nujol): 3290, 1705, 1540 cm$^{-1}$

NMR (CDCl$_3$, δ): 2.06 (1H, t, J=3 Hz), 2.33 (3H, s), 2.47 (3H, s), 3.74 (2H, d, J=3 Hz), 5.20 (2H, s), 5.40 (2H, s), 6.63–6.86 (2H, m), 6.98 (1H, d, J=7 Hz), 7.23–7.46 (6H, m), 7.66–7.93 (2H, m), 9.22 (1H, s)

Analysis Calcd. for C$_{27}$H$_{25}$N$_3$O$_3$: C 73.79, H 5.73, N 9.56, Found: C 73.41, H 5.61, N 9.61.

(18) 8-(2-Isopropoxycarbonylamino-6-methylbenzyloxy)-2-methyl-3-(2-propynyl)imidazo[1,2-a]pyridine mp: 119° to 120° C. (recrystallized from a mixture of diisopropyl ether and n-hexane)

IR (Nujol): 3280, 1705, 1540 cm$^{-1}$

NMR (CDCl$_3$, δ): 1.26 (6H, d, J=7 Hz), 2.07 (1H, t, J=3 Hz), 2.47 (3H, s), 2.52 (3H, s), 3.78 (2H, d, J=3 Hz), 5.03 (1H, septet, J=7 Hz), 5.43 (2H, s), 6.75 (2H, d, J=4 Hz), 6.99 (1H, d, J=8 Hz), 7.26 (1H, t, J=8 Hz), 7.69 (1H, d, J=8 Hz), 7.83 (1H, t, J=4 Hz), 8.63 (1H, s)

Analysis Calcd. for C$_{23}$H$_{25}$N$_3$O$_3$: C 70.57, H 6.44, N 10.78, Found: C 70.60, H 6.43, N 10.48.

(19) 8-(4-Acetamido-2-methylbenzyloxy)-2-methyl-3-(2-propynyl)imidazo[1,2-a]pyridine mp: 189° to 191° C. (recrystallized from a mixture of ethyl acetate and n-hexane)

IR (Nujol): 3250, 1680, 1590, 1540 cm$^{-1}$

NMR (CDCl$_3$, δ): 1.96 (3H, s), 2.06 (1H, t, J=3 Hz), 2.26 (3H, s), 2.40 (3H, s), 3.76 (2H, d, J=3 Hz), 5.10 (1H, s), 6.55 (1H, d, J=7 Hz), 6.75 (1H, t, J=7 Hz), 7.13 (1H, d, J=9 Hz), 7.29 (1H, dd, J=2 Hz, 9 Hz), 7.45 (1H, d, J=2 Hz), 7.73 (1H, d, J=7 Hz), 9.41 (1H, br s)

Analysis Calcd. for C$_{21}$N$_3$O$_2$: C 72.60, H 6.09, N 12.10, Found: C 72.45, H 6.01, N 11.80.

(20) 8-[2-(N-Methoxycarbonyl-N-methylamino)-6methylbenzyloxy]-2-methyl-3-(2-propynyl)imidazo[1,2-a]pyridine mp: 125° to 126° C. (recrystallized from a mixture of ethyl acetate and n-hexane)

IR (Nujol): 3260, 1695, 1570, 1530, 1275 cm$^{-1}$

NMR (CDCl$_3$, δ): 2.06 (1H, t, J=3 Hz), 2.42 (3H, s), 2.47 (3H, s), 3.23 (3H, s), 3.67 (3H, s), 3.77 (2H, d, J=3 Hz), 5.13 (2H, s), 6.47–7.37 (5H, m), 7.73 (1H, dd, J=2 Hz, 7 Hz)

Analysis Calcd for C$_{22}$H$_{23}$N$_3$O$_3$: C 70.01, H 6.14, N 11.13, Found: C 70.00, H 6.07, N 11.13.

(21) 8-(2-Hydroxyacetamido-6-methylbenzyloxy)-2-methyl-3-(2-propynyl)imidazo[1,2-a]pyridine mp: 220° to 222° C. (dec.)

IR (Nujol): 3320, 3190, 1680, 1520, 1280 cm$^{-1}$

NMR (DMSO-d$_6$, δ): 2.33 (3H, s), 2.47 (3H, s), 2.95 (1H, t, J=3 Hz), 3.93 (2H, d, J=3 Hz), 4.02 (2H, s), 5.38 (2H, s), 6.80–7.63 (4H, m), 7.63–8.03 (2H, m), 9.67 (1H, br s)

(22) 8-(2-Acetoxyacetamido-6-methylbenzyloxy)-2-methyl-3-(2-propynyl)imidazo[1,2-a]pyridine mp: 159° to 160° C.

IR (Nujol): 3390, 3275, 1740, 1685, 1600, 1525, 1270, 1220 cm$^{-1}$

NMR (DMSO-d$_6$, δ): 1.97 (3H, s), 2.30 (3H, s), 2.40 (3H, s), 2.93 (1H, t, J=3 Hz), 3.92 (2H, d, J=3 Hz), 4.67 (2H, s), 5.23 (2H, s), 6.77–7.50 (5H, m), 7.83–8.03 (1H, m), 9.73 (1H, br s)

EXAMPLE 5

A mixture of 8-(2-acetoxymethylbenzyloxy)-2-methyl-3-(2-propynyl)imidazo [1,2-a]pyridine (0.36 g) and potassium carbonate (0.214 g) in water (1.8 ml) and methanol (10 ml) was stirred at room temperature for 1.2 hours and then diluted with water. The resulting precipitates were collected by filtration and recrystallized from ethyl acetate to give 8-(2-hydroxymethylbenzyloxy)-2-methyl-3-(2-propynyl)imidazo[1,2-a]pyridine (0.179 g).

mp: 137° to 138° C.

IR (Nujol): 3360, 3300, 1535 cm$^{-1}$

NMR (CDCl$_3$, δ): 2.06 (1H, t, J=3 Hz), 2.41 (3H, s), 3.75 (2H, d, J=3 Hz), 4.26 (1H, br s), 4.76 (2H, s), 5.39 (2H, s), 6.60–6.80 (2H, m), 7.20–7.56 (4H,m), 7.66–7.86 (1H, m)

Analysis Calcd. for C$_{19}$H$_{18}$N$_2$O$_2$: C 74.49, H 5.92, N 9.14, Found: C 74.84, H 5.68, N 8.94.

EXAMPLE 6

A mixture of 8-(4-ethoxycarbonylbenzyloxy)-2-methyl-3-(2-propynyl)imidazo[1,2-a]pyridine (1.04 g) in ethanol (15 ml) and 20% sulfuric acid (40 ml) was refluxed for 5 hours and then ethanol was evaporated in vacuo. The mixture was cooled and the resulting precipitates were collected by filtration. The obtained sulfate was treated with an aqueous solution of sodium bicarbonate and then the mixture was adjusted to pH 4.5 with acetic acid. The resulting precipitates were collected by filtration and air-dried to give 8-(4-carboxybenzyloxy)-2-methyl-3-(2-propynyl)imidazo[1,2-a]pyridine (0.66 g).

mp: 235° to 238° C. (dec.)

IR (Nujol): 3200, 1670, 1550, 1285 cm$^{-1}$

NMR (CF$_3$COOH, δ): 2.25 (1H, t, J=3Hz), 2.63 (3H, s), 3.98 (2H, d, J=3Hz), 5.53 (2H, s), 7.33–7.60 (2H, m), 7.68 (2H, d, J=8Hz), 8.17–8.43 (1H, m), 8.30 (2H, d, J=8Hz)

EXAMPLE 7

To a solution of 8-(2-t-butoxycarbonylamino-6-methylbenzyloxy)-2-methyl-3-(2-propynyl)imidazo[1,2-a]pyridine (1.04 g) in ethanol (15.5 ml) was added dropwise 25% ethanolichydrogen chloride (8.4 ml) with ice-cooling. After being stirred for 3 hours at ambient temperature, the mixture was diluted with diethyl ether. The resulting precipitates were collected by filtration, treated with a saturated aqueous solution of sodium hydrogen carbonate and extracted with methylene chloride. The extract was washed with water, dried over magnesium sulfate, and the solvent was evaporated under reduced pressure. The residue was triturated with diethyl ether to give 8-(2-amino-6-methylbenzyloxy)-2-methyl-3-(2-propynyl)imidazo[1,2-a]pyridine (0.58 g).

mp: 144° to 146° C. (recrystallized from a mixture of ethyl acetate and n-hexane)

IR (Nujol): 3450, 3360, 3300, 1630, 1590, 1535 cm$^{-1}$

NMR (CDCl$_3$, δ): 2.06 (1H, t, J=3 Hz), 2.37 (3H, s), 2.43 (3H, s), 3.75 (2H, d, J=3Hz), 3.80–4.40 (2H, broad s), 5.32 (2H, s), 6.46–6.82 (4H, m), 7.01 (1H, t, J=7.5 Hz), 7.66–7.80 (1H, m)

Analysis Calcd. for C$_{19}$H$_{19}$N$_3$O: C 74.73, H 6.27, N 13.76, Found: C 74.38, H 6.09, N 13.79.

EXAMPLE 8

A mixture of dimethylformamide (277 mg) and phosphorus oxychloride (0.35 ml) was warmed for 1 hour at 40° C. After cooling, dry methylene chloride (4 ml) was added thereto. Pyruvic acid (303 mg) was added thereto with stirring at −20° C. and the mixture was stirred for 1 hour at the same temperature to produce an activated acid solution. On the other hand, 8-(2-amino-6-methylbenzyloxy)-2-methyl-3-(2-propynyl)imidazo[1,2-a]pyridine (0.7 g) was dissolved in a solution of bis(trimethylsilyl)acetamide(1.2 g) in dry methylene chloride (10 ml). To the solution was at a time added the above obtained activated acid solution at −30° C. and the mixture was stirred for 30 minutes at the same temperature. To the reaction mixture was added a saturated aqueous solution of sodium hydrogen carbonate and the organic layer was separated, washed with water and dried over magnesium sulfate.

The solvent was distilled off, and the residue was subjected to column chromatography on silica gel (20 g) and eluted with a mixture of chloroform and methanol (100.1) to give 2-methyl-3-(2-propynyl)-8-(2-pyruvamido-6-methylbenzyloxy)imidazo[1,2-a]pyridine (419 mg).

mp: 158° to 160° C. (recrystallized from a mixture of ethyl acetate and n-hexane)

IR (Nujol): 3330, 3260, 1725, 1690, 1600, 1545 cm$^{-1}$

NMR (CDCl$_3$, $\delta$): 2.08 (1H, t, J=3 Hz), 2.43 (6H, s), 2.48 (3H, s), 3.78 (2H, d, J=3Hz), 5.38 (2H, s), 6.65–6.92 (2H, m), 7.07 (1H, d, J=7.5 Hz), 7.32 (1H, t, J=7.5 Hz), 7.75–7.95 (2H, m), 9.67 (1H, broad s)

EXAMPLE 9

The following compounds were prepared according to a similar manner to that of Example 8.

(1) 8-(2-n-Butyramido-6-methylbenzyloxy)-2-methyl-3-(2-propynyl)imidazo[1,2-a]pyridine mp: 158° to 160° C. (recrystallized from a mixture of ethyl acetate and n-hexane)

IR (Nujol): 3275, 1680, 1600, 1583, 1535 cm$^{-1}$

NMR (CDCl$_3\delta$): 0.90 (3H, t, J=7.5 Hz), 1.69 (2H, sextet, J=7.5 Hz), 2.08 (1H, t, J=3 Hz), 2.44 (2H, t, J=7.5 Hz), 2.45 (6H, s), 3.79 (2H, d, J=3 Hz), 5.35 (2H, s), 6.65–6.90 (2H, m), 7.0 (1H, broad d, J=7.5 Hz), 7.25 (1H, t, J=7.5 Hz), 7.71–7.93 (2H, m), 9.0 (1H, broad s)

(2) 2-Methyl-8-(2-methoxalylamino-6-methylbenzyloxy)-3-(2-propynyl)imidazo[1,2-a]pyridine mp: 140° to 141° C. (recrystallized from ethyl acetate and n-hexane)

IR (Nujol): 3300, 1738, 1680, 1605, 1585, 1540 cm$^{-1}$

NMR (CDCl$_3$, $\delta$): 2.06 (1H, t, J=3 Hz), 2.43 (6H, s), 3.70–3.83 (2H, t, J=3 Hz), 3.75 (3H, s), 5.40 (2H, s), 6.70–6.90 (2H, m), 7.06 (1H, d, J=8 Hz), 7.30 (1H, t, J=8 Hz), 7.75–7.93 (2H, m), 9.95 (1H, br s)

Analysis Calcd. for C$_{22}$H$_{21}$N$_3$O$_4$: C 67.51, H 5.41, N 10.74, Found: C 66.97, H 5.18, N 10.84.

EXAMPLE 10

To a solution of 8-(2-amino-6-methylbenzyloxy)-2-methyl-3-(2-propynyl)imidazo[1,2-a]pyridine (0.4 g) in a mixture of triethylamine (189.2 mg) and methylene chloride (9 ml) was added dropwise sulfamoyl chloride (216 mg) with ice-cooling. After being stirred for 2 hours at ambient temperature, the reaction mixture was diluted with a mixture of chloroform and methanol (95.5). The resultant organic layer was washed with a saturated aqueous solution of sodium hydrogen carbonate, and then with water. The organic layer was dried over magnesium sulfate and the solvent was evaporated under reduced pressure. The crystalline residue was recrystallized from ethanol to give 2-methyl-3-(2-propynyl)-8-(2-sulfamido-6-methylbenzyloxy)imidazo[1,2-a]pyridine.

mp: 138° to 140° C.

IR (Nujol): 3400, 3310, 3270, 1570, 1545 cm$^{-1}$

NMR (DMSO-d$_6$, $\delta$): 2.33 (3H, s), 2.43 (3H, s), 2.93 (1H, t, J=3 Hz), 3.93 (2H, d, J=3 Hz), 5.38 (2H, s), 6.83–7.50 (5H, m), 7.10 (2H, s), 7.86–8.06 (1H, m), 9.06 (1H, broad s)

Analysis Calcd for C$_{19}$H$_{20}$N$_4$O$_3$S:

C 59.36, H 5.24, N 14.57, Found: C 59.96, H 5.30, N 14.07.

EXAMPLE 11

To a solution of 2-methyl-3-(2-propynyl)-8-(2-pyruvamido-6-methylbenzyloxy)imidazo[1,2-a]pyridine (287 mg) in the mixture of acetic acid (0.13 ml) and ethanol (3 ml), sodium cyanoborohydride (72 mg) was added portionwise for 2.5 hours at 5° C. The mixture was poured into a saturated aqueous solution of sodium hydrogen carbonate and extracted with chloroform. The extract was washed with water, dried over magnesium sulfate and the solvent was evaporated under reduced pressure. The residue was subjected to column chromatography on silica gel (10 g) and eluted with a mixture of chloroform and methanol (100.1) to give 8-(2-lactamido-6-methylbenzyloxy)-2-methyl-3-(2-propynyl)imidazo[1,2-a]pyridine (138 mg).

mp: 186° to 188° C. (recrystallized from a mixture of ethyl acetate and n-hexane)

IR (Nujol): 3320, 3270, 1675, 1540, 1275, 1080 cm$^{-1}$

NMR (CDCl$_3$, $\delta$): 1.53 (3H, d, J=7 Hz), 2.04 (1H, t, J=3 Hz), 2.42 (3H, s), 2.50 (3H, s), 3.71 (2H, d, J=3 Hz), 4.29 (1H, q, J=7 Hz), 5.57 (2H, s), 6.43–6.80 (2H, m), 6.90 (1H, broad d, J=8 Hz), 7.17 (1H, broad t, J=8 Hz), 7.68 (1H, broad d, J=7.5 Hz), 8.25 (1H, broad d, J=8 Hz), 10.28 (1H, broad s)

EXAMPLE 12

To a solution of 8-(2-t-butoxycarbonylaminoacetamido-6-methylbenzyloxy)-2-methyl-3-(2-propynyl)imidazo[1,2-a]pyridine (435 mg) in ethanol (2 ml) was added 25% ethanolic hydrogen chloride (0.53 ml) with ice-cooling. After being stirred for 3 hours with ice-cooling, the solvent was evaporated under reduced pressure. To the residue was added a saturated aqueous solution of sodium hydogen carbonate and the aqueous layer was extracted with chloroform. The extract was washed with a water and dried over magnesium sulfate. The solvent was distilled off and the residue was triturated with diethyl ether to give 8-(2-aminoacetamido-6-methylbenzyloxy)-2-methyl-3-(2-propynyl)imidazo[1,2-a]pyridine (215 mg).

mp: 180° to 183° C.

IR (Nujol): 3300, 3120, 1690, 1605, 1540, 1280 cm$^{-1}$

NMR (CDCl$_3$, $\delta$): 1.80 (2H, broad s), 2.08 (1H, t, J=3 Hz), 2.45 (6H, s), 3.45 (2H, s), 3.77 (2H, d, J=3 Hz), 5.37 (2H, s), 6.57–6.87 (2H, m), 7.03 (1H, d, J=8 Hz), 7.28 (1H, t, J=8 Hz), 7.80 (1H, dd, J=2 Hz, 6 Hz), 7.93 (1H, d, J=8 Hz), 9.90 (1H, broad s)

EXAMPLE 13

To a solution of sodium hydride (60% in mineral oil dispersion, 0.14 g) in 2-propynyl alcohol (6 ml) was added 8-(2-cyanobenzyloxy)-3-trimethylammoniomethyl-2-methylimidazo[1,2-a]pyridine iodide (1.5 g) and the mixture was heated at 90°-95° C. with stirring for 2 hours. After being cooled, the mixture was poured into ice-water and the resulting precipitate was collected by filtration and dissolved in methylene chloride. The solution was treated successively with silica gel (1 g) and activated charcoal and evaporated in vacuo. The crystalline residue was recrystallized from a mixture of methylene chloride and n-hexane to give 8-(2-cyanobenzyloxy)-2-methyl-3-(2-propynyloxymethyl-)imidazo[1,2-a]pyridine (0.76 g).

mp: 144° C. (recrystallized from a mixture of ethyl acetate and n-hexane)

IR (Nujol): 3270, 2215, 1280, 1060 cm$^{-1}$

NMR (CDCL$_3$, δ): 2.40–2.66 (1H, m), 2.50 (3H, s), 4.10 (2H, d, J=2 Hz), 4.86 (2H, s), 5.50 (2H, s), 6.43–6.90 (2H, m), 7.20–7.96 (5H, m)

EXAMPLE 14

The following compound was prepared according to a similar manner to that of Example 13.

8-(2-Acetamidobenzyloxy)-2-methyl-3-(2-propynyloxymethyl)imidazo[1,2-a]pyridine mp: 153° to 155° C. (recrystallized from a mixture of ethyl acetate and n-hexane)

IR (Nujol): 3325 (shoulder), 3275, 1685 cm$^{-1}$

NMR (CDCl$_3$δ): 2.25 (3H, s), 2.43–2.60 (1H, m), 2.53 (3H, s), 4.12 (2H, d, J=3 Hz), 4.88 (2H, s), 5.33 (2H, s), 6.65–6.80 (2H, m), 7.00–7.56 (3H, m), 7.75–8.20 (2H, m), 9.23 (1H, br s)

Analysis Calcd. for C$_{21}$H$_{21}$N$_3$O$_3$ C 69.41, H 5.83, N 11.56, Found: C 69.18, H 6.13, N 11.02.

EXAMPLE 15

To a solution of 8-(2-amino-6-methylbenzyloxy)-2-methyl-3-(2-propynyl)imidazo[1,2-a]pyridine (9.3 g) in dichloromethane (140 ml) was added dropwise benzoyl isothiocyanate and the mixture was stirred for 1 hour. The solvent was evaporated under reduced pressure and the residue was triturated with ether (50 ml) to give a crystalline product. The crystals were recrystallized from ethanol to give 8-{2-[3-(benzoyl)thioureido]-6-methylbenzyloxy}-2-methyl-3-(2-propynyl-)imidazo[1,2-a]pyridine (11.7 g).

mp: 159°–160° C.

IR (Nujol): 3290, 3270, 1645, 1525, 1255

NMR (CDCl$_3$, δ): 2.06 (1H, t, J=3 Hz), 2.40 (3H, s), 2.49 (3H, s), 3.40 (2H, d, J=3 Hz), 5.30 (2H, s), 6.60–6.86 (2H, m), 7.13–7.90 (9H, m), 9.20 (1H, br s), 12.23 (1H, br s)

EXAMPLE 16

To a solution of 8-{2-[3-(benzoyl)thioureido]-6-methylbenzyloxy}-2-methyl-3-(2-propynyl-)imidazo[1,2-a]pyridine (1.08 g) in methanol (6.5 ml) and tetrahydrofuran (19 ml) was added a solution of potassium carbonate (0.32 g) in water (6.5 ml) and the mixture was stirred at room temperature for 4 hours. The reaction mixture was diluted with water (150 ml) and then the precipitates were collected by filtration. The precipitates were recrystallized from an aqueous ethanol to give 2-methyl-8-(6-methyl-2-thioureidobenzyloxy)-3-(2-propynyl)imidazo[1,2-a]pyridine (0.55 g).

mp: 155° to 153° C.

IR (Nujol): 3460, 3340, 3300, 3150, 1600, 1545 cm$^{-1}$

NMR (DMSO-d$_6$, δ): 2.29 (3H, s), 2.36 (3H, s), 2.96 (1H, t, J=3 Hz), 3.89 (2H, d, J=3 Hz), 5.15 (2H, s), 6.70–7.0 (2H, m), 7.06–7.53 (5H, m), 7.88 (1H, dd, J=2, 6 Hz), 9.46 (1H, s)

Analysis Calcd for C$_{20}$H$_{20}$N$_4$OS: C 65.91, H 5.53, N 15.37, Found: C 65.91, H 5.48, N 15.30.

EXAMPLE 17

To a solution of 8-(2-methoxycarbonylamino-6-methylbenzyloxy)-2-methyl-3-(2-propynyl)imidazo[1,2-a]pyridine (230 mg) in 1.4-dioxane (4.6 ml) were added 36% formaldehyde (105 mg), 50% dimethylamine in water (142 mg) and cuprous chloride (12.5 mg). After the mixture was stirred at 50° C. for 5 hours, 1.4-dioxane was evaporated under reduced pressure. The resultant residue was dissolved in chloroform (20 ml) and insoluble material was filtered off. The filtrate was washed with an aqueous solution of sodium bicarbonate and water in turn, and dried over magnesium sulfate. The solvent was evaporated under reduced pressure and the residue was recrystallized from a mixture of ethyl acetate and n-hexane to give 3-(4-N,N-dimethylamino-2-butynyl(-8-(2-methoxycarbonylamino-6-methylbenzyloxy)-2-methylimidazo-[1,2-a]pyridine (175 mg).

mp: 142° to 144° C.

IR (Nujol): 1715, 1540, 1270 cm$^{-1}$

NMR (CDCl$_3$, δ): 2.25 (6H, s), 2.50 (6H, s), 3.20 (2H, t, J=2 Hz), 3.77 (3H, s), 3.83 (2H, t, J=2 Hz), 5.43 (2H, s), 6.63–6.87 (2H, m), 7.00 (1H, m), 7.18–7.40 (1H, m), 7.70–7.97 (2H, m) 9.38 (1H, bs)

Mass: M+ 420

EXAMPLE 18

The following compound was prepared according to similar manners to those of Preparation 24 and further Example 1 from 2,6-di(acetamido)benzyl alcohol. 8-[2,6-Di(acetamido)benzyloxy]-2-methyl-3-(2-propynyl) imidazo[1,2-a]pyridine.

mp: 230 to 231° C. (dec.)

IR (Nujol): 3230, 1650, 1520, 1285 cm$^{-1}$

NMR (DMSO-d$_6$, δ): 2.05 (6H, s), 2.33 (3H, s), 2.93 (1H, t, J=3 Hz), 3.92 (2H, d, J=3 Hz), 5.27 (2H, s), 6.66–7.00(2H, m), 7.27–7.50(3H, m), 7.90–8.07 (1H, m), 9.70 (2H, s)

EXAMPLE 19

The following compounds were prepared according to a similar manner to that of Example 3.

(1) 8-(2-Methoxycarbonylaminomethylbenzyloxy)-2-methyl-3-(2-propynyl)imidazo[1,2-a]pyridine.

mp: 167° to 169° C.

IR (Nujol): 3270, 1700, 1550, 1530, 1290, 1265 cm$^{-1}$

NMR (CDCl$_3$, δ): 2.07 (1 H, t, J=3 Hz), 2.45 (3H, s), 3.67 (3H, s), 3.78 (2H, d, J=3 Hz), 4.42 (2H, d, J=6 Hz), 5.30 (2H, s), 6.50–6.97 (2H, m), 7.23–8.00 (6H, m)

Analysis Calcd. for C$_{21}$H$_{21}$N$_3$O$_3$: C 69.40, H 5.82, N 11.56, Found: C 69.41, H 5.77, N 11.47.

(2) 2-Methyl-8-[2-methyl-6-(N-methyl-N-t-butoxycarbonylamino)benzyloxy]-3-(2-propynyl)imidazo[1,2-a]pyridine IR (film): 3300, 1690, 1542 cm$^{-1}$ NMR (CDCl$_3$, δ): 1.41 (9H, s), 2.07(1 H, t, J=3 Hz), 2.43 (3H, s), 2.46 (3H, s), 3.27 (3H, s), 3.78 (2H, d, J=3 Hz), 5.16 (2H, s), 6.50–6.83 (2H, m), 6,90–7.33 (3H, m), 7.75 (1, dd, J=2, 6 Hz)

(3) 2-Methyl-8-[2-methyl-6-(1-methylureido)benzyloxy]-3-(2-propynyl)imidazo[1,2-a]pyridine mp: 139° to 141° C.

IR (Nujol): 3475, 3280, 3180, 1655, 1580, 1540 cm$^{-1}$

NMR (CDCl$_3$, δ): 2.08 (1H, t, J=3 Hz), 2.40 (3H, s), 2.50 (3H, s), 3.20 (3H, s), 3.76 (2H, d, J=3 Hz), 4.45 (2H, s), 5.12 (2H, s), 6.61–6.93 (2H, m), 7.12–7.49 (3H, m), 7.77 (1H, dd, J=2, 6 Hz)

Analysis Calcd. for $C_{21}H_{22}N_4O_2$: C 67.36, H 5.92, N 14.96, Found: C 67.83, H 5.71, N 14.96.

(4) 2-Methyl-8-[2-methyl-6-(N-methyl-N-mesylamino)-benzyloxy]-3-(2-propynyl)imidazo[1,2-a]pyridine mp: 168° to 170° C.

IR (Nujol): 3245, 1530, 1330, 1140 cm$^{-1}$

NMR (CDCl$_3$, δ): 2.06 (1H, t, J=3 Hz), 2.41 (3H, s), 2.48 (3H, s), 2.95 (3H, s), 3.27 (3H, s), 3.76 (2H, d, J=3 Hz), 5.20 (1H, br s), 5.61 (1H, br s), 6.67–6.92 (2H, m), 7.10–7.46 (3H, m), 7.71–7.88 (1H, m)

Analysis Calcd. for $C_{21}H_{23}N_3O_3S$: C 63.46, H 5.83, N 10.57, Found: C 63.60, H 5.39, N 10.48.

(5) 8-(2-Methoxycarbonylamino-6-methylbenzyloxy)-2,5-dimethyl-3-(2-propynyl)imidazo[1,2-a]pyridine mp: 165° to 166° C.

IR (Nujol): 3280, 3190, 1730, 1605, 1580, 1540, 1500 cm$^{-1}$

NMR (CDCl$_3$, δ): 2.17 (1H, t, J=3 Hz), 2.47 (6H, s), 2.93 (3H, s), 3.75 (3H, s), 3.96 (2H, d, J=3 Hz), 5.30 (2H, s), 6.37 (1H, d, J=7.5 Hz), 6.69 (1H, d, J=7.5 Hz), 6.99 (1H, d, J=8 Hz), 7.29 (1H, t, J=8 Hz), 7.80 (1H, d, J=8 Hz), 9.48 (1H, s)

Analysis Calcd. for $C_{22}H_{23}N_3O_3$: C 70.01, H 6.14, N 11.13, Found: C 70.08, H 6.24, N 11.06.

EXAMPLE 20

The following compound was prepared according to a similar manner to that of Example 7.

2-Methyl-8-(2-methyl-6-methylaminobenzyloxy)-3-(2-propynyl)imidazo[1,2-a]pyridine mp: 107° to 110° C.

NMR (CDCl$_3$, δ): 2.06 (1H, t, J=3 Hz), 2.38 (3H, s), 2.45 (3H, s), 2.84 (3H, s), 3.75 (2H, d, J=3 Hz), 5.10 (1H, br s), 5.27 (2H, s), 6.51 (2H, d, J=7.5 Hz), 6.77 (2H, d, J=4 Hz), 7.10 (1H, t, J=7.5 Hz), 7.71 (1H, t, J=4 Hz).

EXAMPLE 21

To a solution of 8-(2-methyl-6-methylaminobenzyloxy)-2-methyl-3-(2-propynyl)imidazo[1,2-a]pyridine (0.47 g) in a mixture of triethylamine (0.613 ml) and methylene chloride (5 ml) was added dropwise acetyl chloride (0.209 ml) with ice-cooling. After being stirred for 1 hour at ambient temperature, the reaction mixture was treated in a conventional manner to give 2-methyl-8-[2-methyl-6-(N-methylacetamido)benzyloxy]-3-(2-propynyl)imidazo[1,2-a]pyridine (0.22 g).

mp: 76° C.

IR (Nujol): 3190, 1655, 1580, 1540 cm$^{-1}$

NMR (CDCl$_3$, δ): 1.85 (3H, s), 2.06 (1H, t, J=3 Hz), 2.41 (3H, s), 2.50 (3H, s), 3.22 (3H, s), 3.76 (2H, d, J=3 Hz), 5.13 (2H, s), 6.56–6.93 (2H, m), 7.05 (1H, dd, J=3.6 Hz), 7.20–7.43 (2H, m), 7.77 (1H, dd, J=1.5 Hz, 6 Hz)

EXAMPLE 22

To a suspension of 8-[2,6-bis(hydroxymethyl)benzyloxy]-2-methyl-3-(2-propynyl)imidazo[1,2-a]pyridine (4.9 g) in methanol (80 ml) was added 1 N hydrochloric acid (15 ml) at room temperature. The obtained clear solution was concentrated under reduced pressure and the residue was recrystallized from a mixture of acetone (100 ml) and water (8 ml) to give 8-[2,6-bis(hydroxymethyl)benzyloxy]-2-methyl-3-(2-propynyl)imidazo[1,2-a]pyridine hydrochloride (4.44g)

mp: 192° to 194° C.

IR (Nujol): 3280, 1660, 1565, 1520, 1280 cm$^{-1}$

NMR (DMSO-d$_6$, δ): 2.46 (3H, s), 3.17 (1H, t, J=3 Hz), 4.15 (2H, d, J=3 Hz), 4.65 (4H, s), 5.53 (2H, s), 7.43 (3H, s), 7.50 (1H, d, J=6 Hz), 7.70 (1H, t, J=6 Hz), 8.40 (1H, d, J=6 Hz)

Analysis Calcd. for $C_{20}H_{20}N_2O_3HCl$: C 64.43, H 5.68, N 7.51 Found: C 64.67, H 5.75, N 7.66.

EXAMPLE 23

The following compounds were prepared according to a similar manner to that of Example 22.

(1) 8-(2-Hydroxyacetamido-6-methylbenzyloxy)-2-methyl-3-(2-propynyl)imidazo[1,2-a]pyridine hydrochloride hydrate mp: 164° to 168° C.

IR (Nujol): 3500, 3350, 3300, 3220, 1685, 1565, 1540 cm$^{-1}$

NMR (DMSO-d$_6$, δ): 2.43 (3H, s), 2.48 (3H, s), 3.17 (1H, t, J=3 Hz), 3.95 (2H, s), 4.17 (2H, d, J=3 Hz), 5.45 (2H, s), 7.06–7.83 (5H, m), 8.23–8.53 (1H, m), 9.58 (1H, br s)

| Analysis Calcd. for $C_{21}H_{21}N_3O_3HCl.H_2O$ | | | | |
|---|---|---|---|---|
| C | H | N | Cl | H$_2$O |
| 60.35 | 5.55 | 10.06 | 8.48 | 4.31 |
| Found: 60.00 | 5.58 | 9.98 | 8.39 | 4.34 |

(2) 8-(2-Methoxycarbonylamino-6-methylbenzyloxy)-2-methyl-3-(2-propynyl)imidazo[1,2-a]pyridine sulfate mp: 170° to 171° C.

IR (Nujol): 3390, 3260, 1720, 1660, 1598, 1565, 1515 cm$^{-1}$

NMR (DMSO-d$_6$, δ): 2.40 (3H, s), 2.46 (3H, s), 3.15 (1H, t, J=3 Hz), 3.62 (3H, s), 4.16 (2H, d, J=3 Hz), 5.41 (2H, s), 7.07–7.74 (5H, m), 8.42 (1H, dd, J=2, 6 Hz), 9.26 (1H, s)

Analysis Calcd for $C_{21}H_{23}N_3O_7S$: C 54.66, H 5.02, N 9.11, S 6.95, Found: C 54.82, H 5.02, N 9.01, S 6.76.

(3) 8-(2-Methoxycarbonylamino-6-methylbenzyloxy)-2-methyl-3-(2-propynyl)imidazo[1,2-a]pyridine hydrochloride mp: 178° to 179° C.

IR (Nujol): 3195, 2105, 1720, 1660, 1560, 1520 cm$^{-1}$

NMR (DMSO-d$_6$, δ): 2.41 (3H, s), 2.50 (3H, s), 3.20 (1H, t, J=2Hz), 3.61 (3H, s), 4.19 (2H, d, J=2 Hz), 5.44 (2H, s), 7.04–7.77 (5H, m), 8.45 (1H, bd, J=6 Hz), 9.45 (1H, s)

Analysis Calcd. for $C_{21}H_{22}ClN_3O_3.\frac{1}{2}H_2O$: C 61.69, H 5.65, N 10.28, Cl 8.67, Found: C 61.83, H 5.34, N 10.29, Cl 9.22.

EXAMPLE 24

The following compound was obtained according to a similar manner to that of Example 21.

2-Methyl-8-[2-(1,3-dimethylureido)-6-methylbenzyloxy]-3-(2-propynyl)imidazo[1,2-a]pyridine mp: 96° C. (dec.)

IR (Nujol): 3375, 3240, 1635, 1535 cm$^{-1}$

NMR (CDCl$_3$, δ): 2.06 (1H, t, J=3 Hz), 2.40 (3H, s), 2.49 (3H, s), 2.58 (3H, s), 2.58 (3H, d, J=7 Hz), 3.20 (3H, s), 3.77 (2H, d, J=3 Hz), 4.45 (1H, bq, J=7Hz), 5.15 (2H, s), 6.58–6.92 (2H, m), 7.06–7.50 (3H, m), 7.78 (1H, dd, J=2, 6 Hz)

Analysis Calcd. for $C_{22}H_{24}N_4O_2.H_2O$: C 66.99, H 6.64, N 14.20, Found: C 67.49, H 6.03, N 14.15.

EXAMPLE 25

The following compounds were prepared according to a similar manner to that of Example 3.

(1) 2-Methyl-8-(6-methyl-2-ureidobenzyloxy)-3-(2-propynyl)imidazo[1,2-a]pyridine
IR (Nujol): 3380, 3270, 3240, 3170, 1660, 1590, 1540, 1090 cm$^{-1}$ (2) 8-(2-Acetoxymethylbenzyloxy)-2-methyl-3-(2-propynyl)imidazo[1,2-a]pyridine
IR (Nujol): 3280, 1715 cm$^{-1}$ (3) 8-(2-Formamido-6-methylbenzyloxy)-2-methyl-3-(2-propynyl)imidazo[1,2-a]pyridine
IR (Nujol): 3200, 1685, 1605, 1585, 1540, 1280 cm$^{-1}$ (4) 8-(2-Ethoxycarbonylamino-6-methylbenzyloxy)-2-methyl-3-(2-propynyl)imidazo[1,2-a]pyridine
IR (Nujol): 3280, 1710, 1540 cm$^{-1}$ (5) 8-(2-Methanesulfonylamino-6-methylbenzyloxy)-2-methyl-3-(2-propynyl)imidazo[1,2-a]pyridine
IR (Nujol): 3275, 1540, 1323, 1145 cm$^{-1}$ (6) 8-(3-Acetamido-2-methylbenzyloxy)-2-methyl-3-(2-propynyl)imidazo[1,2-a]pyridine
IR (Nujol): 3200, 1635, 1540 cm$^{-1}$ (7) 2-Methyl-8-[6-methyl-2-(3-methylureido)benzyloxy]-3-(2-propynyl)imidazo[1,2-a]pyridine
IR (Nujol): 3400, 3290, 1695, 1605 cm$^{-1}$ (8) 8-(5-Acetamido-2-methylbenzyloxy)-2-methyl-3-(2-propynyl)imidazo[1,2-a]pyridine
IR (Nujol): 3270, 1670, 1595, 1535, 1490 cm$^{-1}$ (9) 8-(2-t-Butoxycarbonylamino-6-methylbenzyloxy)-2-methyl-3-(2-propynyl)imidazo[1,2-a]pyridine
IR (CHCl$_3$): 3400, 3300, 1710, 1580, 1535, 1370, 1270, 1150 cm$^{-1}$

(10) 8-(2-Acetamido-6-methylbenzyloxy)-2-methyl-3-(2-propynyl)imidazo[1,2-a]pyridine
IR (Nujol): 3340, 3270, 1683, 1603, 1585, 1280 cm$^{-1}$

(11) 8-(2-Hydroxymethylbenzyloxy)-2-methyl-3-(2-propynyl)imidazo[1,2-a]pyridine
IR (Nujol): 3360, 3300, 1535 cm$^{-1}$

(12) 8-(4-Carboxybenzyloxy)-2-methyl-3-(2-propynyl)imidazo[1,2-a]pyridine
IR (Nujol): 3200, 1670, 1550, 1285 cm$^{-1}$

(13) 8-(2-Amino-6-methylbenzyloxy)-2-methyl-3-(2-propynyl)imidazo[1,2-a]pyridine
IR (Nujol): 3450, 3360, 3300, 1630, 1590, 1535 cm$^{-1}$

(14) 2-Methyl-3-(2-propynyl)-8-(2-pyruvamido-6-methylbenzyloxy)imidazo[1,2-a]pyridine
IR (Nujol): 3330, 3260, 1725, 1690, 1600, 1545 cm$^{-1}$

(15) 8-(2-n-Butyramido-6-methylbenzyloxy)-2-methyl-3-(2-propynyl)imidazo[1,2-a]pyridine
IR (Nujol): 3275, 1680, 1600, 1583, 1535 cm$^{-1}$

(16) 2-Methyl-8-(2-methoxalylamino-6-methylbenzyloxy)-3-(2-propynyl)imidazo[1,2-a]pyridine
IR (Nujol): 3300, 1738, 1680, 1605, 1585, 1540 cm$^{-1}$

(17) 2-Methyl-3-(2-propynyl)-8-(2-sulfamido-6-methylbenzyloxy)imidazo[1,2-a]pyridine
IR (Nujol): 3400, 3310, 3270, 1570, 1545 cm$^{-1}$

(18) 8-(2-Lactamido-6-methylbenzyloxy)-2-methyl-3-(2-propynyl)imidazo[1,2-a]pyridine
IR (Nujol): 3320, 3270, 1675, 1540, 1275, 1080 cm$^{-1}$

(19) 8-(2-Aminoacetamido-6-methylbenzyloxy)-2-methyl-3-(2-propynyl)imidazo[1,2-a]pyridine
IR (Nujol): 3300, 3120, 1690, 1605, 1540, 1280 cm$^{-1}$

(20) 8-(2-Cyanobenzyloxy)-2-methyl-3-(2-propynyloxymethyl)imidazo[1,2-a]pyridine
IR (Nujol): 3270, 2215, 1280, 1060 cm$^{-1}$

(21) 8-(2-Acetamidobenzyloxy)-2-methyl-3-(2-propynyloxymethyl)imidazo[1,2-a]pyridine
IR (Nujol): 3325 (shoulder), 3275, 1685 cm$^{-1}$

(22) 8-{2-[3-(Benzoyl)thioureido]-6-methylbenzyloxy}-2-methyl-3-(2-propynyl)imidazo[1,2-a]pyridine
IR (Nujol): 3290, 3270, 1645, 1525, 1255

(23) 2-Methyl-8-(6-methyl-2-thioureidobenzyloxy)-3-(2-propynyl)imidazo[1,2-a]pyridine
IR (Nujol): 3460, 3340, 3300, 3150, 1600, 1545 cm$^{-1}$

(24) 3-(4-N,N-Dimethylamino-2-butynyl)-8-(2-methoxycarbonylamino-6-methylbenzyloxy)-2-methylimidazo[1,2-a]pyridine.
IR (Nujol): 1715, 1540, 1270 cm$^{-1}$

(25) 8-[2,6-Di(acetamido)benzyloxy]-2-methyl-3-(2-propynyl)imidazo[1,2-a]pyridine
IR (Nujol): 3230, 1650, 1520, 1285 cm$^{-1}$

(26) 2-Methyl-8-(2-methyl-6-methylaminobenzyloxy)-3-(2-propynyl)imidazo[1,2-a]pyridine
mp: 107° to 110° C.

(27) 2-Methyl-8-[2-methyl-6-(N-methylacetamido)benzyloxy]-3-(2-propynyl)imidazo[1,2-a]-pyridine
IR (Nujol): 3190, 1655, 1580, 1540 cm$^{-1}$

(28) 2-Methyl-8-[2-(1,3-dimethylureido)-6-methylbenzyloxy]-3-(2-propynyl)imidazo[1,2-a]pyridine
IR (Nujol): 3375, 3240, 1635, 1535 cm$^{-1}$.

EXAMPLE 26

The following compounds were prepared according to a similar manner to that of Example 1.

(1) 2-Methyl-3-(2-propynyl)-8-(2-trifluoromethylbenzyloxy)imidazo[1,2-a]pyridine
IR (Nujol): 3290 cm$^{-1}$ (2) 8-(2-Acetamidobenzyloxy)-2-methyl-3-(2-propynyl)imidazo[1,2-a]pyridine
IR (Nujol): 3300, 1685, 1585, 1540, 1525 cm$^{-1}$ (3) 2-Methyl-3-(2-propynyl)-8-(2-ureidobenzyloxy)imidazo[1,2-a]pyridine
IR (Nujol): 3460, 3220, 1700, 1585, 1540 cm$^{-1}$ (4) 8-(2-Methoxycarbonylaminobenzyloxy)-2-methyl-3-(2-propynyl)imidazo[1,2-a]pyridine
IR (Nujol): 3310, 1720, 1590, 1540 cm$^{-1}$ (5) 8-(2-Formamidobenzyloxy)-2-methyl-3-(2-propynyl)imidazo[1,2-a]pyridine
IR (Nujol): 3280, 1690, 1590, 1540, 1285 cm$^{-1}$ (6) 8-(2-Carbamoylbenzyloxy)-2-methyl-3-(2-propynyl)imidazo[1,2-a]pyridine
IR (Nujol): 3425, 3300, 3140, 1660, 1600, 1540 cm$^{-1}$ (7) 8-(2-Methoxymethoxybenzyloxy)-2-methyl-3-(2-propynyl)imidazo[1,2-a]pyridine
IR (Nujol): 3150, 2100, 1600, 1530 cm$^{-1}$ (8) 8-(4-Hydroxymethylbenzyloxy)-2-methyl-3-(2-propynyl)imidazo[1,2-a]pyridine
IR (Nujol): 3220, 3150, 1535, 1280 cm$^{-1}$ (9) 8-(4-Ethoxycarbonylbenzyloxy)-2-methyl-3-(2-propynyl)imidazo[1,2-a]pyridine
IR (Nujol): 3300, 1710, 1610, 1540, 1280 cm$^{-1}$

(10) 8-(4-Carbamoylbenzyloxy)-2-methyl-3-(2-propynyl)imidazo[1,2-a]pyridine
IR (Nujol): 3350, 3290, 3170, 1645, 1610, 1280 cm$^{-1}$

(11) 8-(3-Hydroxybenzyloxy)-2-methyl-3-(2-propynyl)imidazo[1,2-a]pyridine
IR (Nujol): 3270, 1585, 1540, 1290 cm$^{-1}$

(12) 8-(2-Isonicotinamido-6-methylbenzyloxy)-2-methyl-3-(2-propynyl)imidazo[1,2-a]pyridine
IR (Nujol): 3375, 3245, 1680, 1600, 1540, 1520 cm$^{-1}$

(13) 2-Methyl-8-(2-methyl-6-propionamidobenzyloxy)-3-(2-propynyl)imidazo[1,2-a]pyridine
IR (Nujol): 3310, 1690, 1600, 1585, 1540 cm$^{-1}$

(14) 8-[2,6-Bis(hydroxymethyl)benzyloxy]-2-methyl-3-(2-propynyl)imidazo[1,2-a]pyridine
IR (Nujol): 3300, 1543, 1290, 1090 cm$^{-1}$

(15) 8-(2-Hydroxymethyl-6-methylbenzyloxy)-2-methyl-3-(2-propynyl)imidazo[1,2-a]pyridine
IR (Nujol): 3200, 1540, 1285 cm$^{-1}$

(16) 8-(2-t-Butoxycarbonylaminoacetamido-6-methylbenzyloxy)-2-methyl-3-(2-propynyl)imidazo[1,2-a]pyridine
NMR (CDCl$_3$, δ): 1.30 (9H, s), 2.08 (1H, t, J=3 Hz), 2.47 (6H, s), 3.78 (2H, d, J=3 Hz), 4.03 (2H, d, J=6 Hz), 5.42 (2H, s), 6.70–7.40 (5H, m), 7.77–8.10 (2H, m), 9.67 (1H, broad s)
(17) 8-(2-Benzyloxycarbonylamino-6-methylbenzyloxy)-2-methyl-3-(2-propynyl)imidazo[1,2-a]pyridine
IR (Nujol): 3290, 1705, 1540 cm$^{-1}$
(18) 8-(2-Isopropoxycarbonylamino-6-methylbenzyloxy)-2-methyl-3-(2-propynyl)imidazo[1,2-a]pyridine
IR (Nujol): 3280, 1705, 1540 cm$^{-1}$
(19) 8-(4-Acetamido-2-methylbenzyloxy)-2-methyl-3-(2-propynyl)imidazo[1,2-a]pyridine
IR (Nujol): 3250, 1680, 1590, 1540 cm$^{-1}$
(20) 8-[2-(N-Methoxycarbonyl-N-methylamino)-6-methylbenzyloxy]-2-methyl-3-(2-propynyl)imidazo[1,2-a]pyridine
IR (Nujol): 3260, 1695, 1570, 1530, 1275 cm$^{-1}$
(21) 8-(2-Hydroxyacetamido-6-methylbenzyloxy)-2-methyl-3-(2-propynyl)imidazo[1,2-a]pyridine
IR (Nujol): 3320, 3190, 1680, 1520, 1280 cm$^{-1}$
(22) 8-(2-Acetoxyacetamido-6-methylbenzyloxy)-2-methyl-3-(2-propynyl)imidazo[1,2-a]pyridine
IR (Nujol): 3390, 3275, 1740, 1685, 1600, 1525, 1270, 1220 cm$^{-1}$
(23) 8-(2-Hydroxymethylbenzyloxy)-2-methyl-3-(2-propynyl)imidazo[1,2-a]pyridine
IR (Nujol): 3360, 3300, 1535 cm$^{-1}$
(24) 8-(4-Carboxybenzyloxy)-2-methyl-3-(2-propynyl)imidazo[1,2-a]pyridine
IR (Nujol): 3200, 1670, 1550, 1285 cm$^{-1}$
(25) 8-(2-Amino-6-methylbenzyloxy)-2-methyl-3-(2-propynyl)imidazo[1,2-a]pyridine
IR (Nujol): 3450, 3360, 3300, 1630, 1590, 1535 cm$^{-1}$
(26) 2-Methyl-3-(2-propynyl)-8-(2-pyruvamido-6-methylbenzyloxy)imidazo[1,2-a]pyridine
IR (Nujol): 3330, 3260, 1725, 1690, 1600, 1545 cm$^{-1}$
(27) 8-(2-n-Butyramido-6-methylbenzyloxy)-2-methyl-3-(2-propynyl)imidazo[1,2-a]pyridine
IR (Nujol): 3275, 1680, 1600, 1583, 1535 cm$^{-1}$
(28) 2-Methyl-8-(2-methoxalylamino-6-methylbenzyloxy)-3-(2-propynyl)imidazo[1,2-a]pyridine
IR (Nujol): 3300, 1738, 1680, 1605, 1585, 1540 cm$^{-1}$
(29) 2-Methyl-3-(2-propynyl)-8-(2-sulfamido-6-methylbenzyloxy)imidazo[1,2-a]pyridine
IR (Nujol): 3400, 3310, 3270, 1570, 1545 cm$^{-1}$
(30) 8-(2-Lactamido-6-methylbenzyloxy)-2-methyl-3-(2-propynyl)imidazo[1,2-a]pyridine
IR (Nujol): 3320, 3270, 1675, 1540, 1275, 1080 cm$^{-1}$
(31) 8-(2-Aminoacetamido-6-methylbenzyloxy)-2-methyl-3-(2-propynyl)imidazo[1,2-a]pyridine
IR (Nujol): 3300, 3120, 1690, 1605, 1540, 1280 cm$^{-1}$
(32) 8-(2-cyanobenzyloxy)-2-methyl-3-(2-propynyloxymethyl)imidazo[1,2-a]pyridine
IR (Nujol): 3270, 2215, 1280, 1060 cm$^{-1}$
(33) 8-(2-Acetamidobenzyloxy)-2-methyl-3-(2-propynyloxymethyl)imidazo[1,2-a]pyridine
IR (Nujol): 3325 (shoulder), 3275, 1685 cm$^{-1}$
(34) 8-{2-[3-(Benzoyl)thioureido]-6-methylbenzyloxy}-2-methyl-3-(2-propynyl)imidazo[1,2-a]pyridine
IR (Nujol): 3290, 3270, 1645, 1525, 1255
(35) 2-Methyl-8-(6-methyl-2-thioureidobenzyloxy)-3-(2-propynyl)imidazo[1,2-a]pyridine
IR (Nujol): 3460, 3340, 3300, 3150, 1600, 1545 cm$^{-1}$
(36) 3-(4-N,N-Dimethylamino-2-butynyl)-8-(2-methoxycarbonylamino-6-methylbenzyloxy)-2-methy 1,2-a]pyridine
IR (Nujol): 1715, 1540, 1270 cm$^{-1}$
(37) 8-(2-Methoxycarbonylaminomethylbenzyloxy)-2-methyl-3-(2-propynyl)imidazo[1,2-a]pyridine
IR (Nujol): 3270, 1700, 1550, 1530, 1290, 1265 cm$^{-1}$
(38) 2-Methyl-8-[2-methyl-6-(N-methyl-N-t-butoxycarbonylamino)benzyloxy]-3-(2-propynyl)imidazo[1,2-a]pyridine
IR (Film): 3300, 1690, 1542 cm$^{-1}$
(39) 2-Methyl-8-[2-methyl-6-(1-methylureido)benzyloxy]-3-(2-propynyl)imidazo[1,2-a]pyridine
IR (Nujol): 3475, 3280, 3180, 1655, 1580, 1540 cm$^{-1}$
(40) 2-Methyl-8-[2-methyl-6-(N-methyl-N-mesylamino)benzyloxy]-3-(2-propynyl)imidazo[1,2-a]pyridine
IR (Nujol): 3245, 1530, 1330, 1140 cm$^{-1}$
(41) 8-(2-Methoxycarbonylamino-6-methylbenzyloxy)-2,5-dimethyl-3-(2-propynyl)imidazo[1,2-a]pyridine
IR (Nujol): 3280, 3190, 1730, 1605, 1580, 1540, 1500 cm$^{-1}$
(42) 2-Methyl-8-(2-methyl-6-methylaminobenzyloxy)-3-(2-propynyl)imidazo[1,2-a]pyridine
mp: 107° to 110° C.
NMR (CDCl$_3$, δ): 2.06 (1H, t, J=3 Hz), 2.38 (3H, s), 2.45 (3H, s), 2.84 (3H, s), 3.75 (2H, d, J=3 Hz), 5.10 (1H, br s), 5.27 (2H, s), 6.51 (2H, d, J=7.5 Hz), 6.77 (2H, d, J=4 Hz), 7.10 (1H, t, J=7.5 Hz), 7.71 (1H, t, J=4 Hz)
(43) 2-Methyl-8-[2-methyl-6-(N-methylacetamido)benzyloxy]-3-(2-propynyl)imidazo[1,2-a]pyridine
IR (Nujol): 3190, 1655, 1580, 1540 cm$^{-1}$
(44) 2-Methyl-8-[2-(1,3-dimethylureido-6-methylbenzyloxy]-3-(2-propynyl)imidazo[1,2-a]pyridine
IR (Nujol): 3375, 3240, 1635, 1535 cm$^{-1}$

EXAMPLE 27

The following compound was prepared according to a similar manner to that of Example 5.
8-(4-Hydroxymethylbenzyloxy)-2-methyl-3-(2-propynyl)imidazo[1,2-a]pyridine
IR (Nujol): 3220, 3150, 1535, 1280 cm$^{-1}$

EXAMPLE 28

The following compounds were prepared according to a similar manner to that of Example 8.
(1) 2-Methyl-8-(6-methyl-2-ureidobenzyloxy)-3-(2-propynyl)imidazo[1,2-a]pyridine
IR (Nujol): 3380, 3270, 3240, 3170, 1660, 1590, 1540, 1090 cm$^{-1}$
(2) 8-(2-Formamido-6-methylbenzyloxy)-2-methyl-3-(2-propynyl)imidazo[1,2-a]pyridine
IR (Nujol): 3200, 1685, 1605, 1585, 1540, 1280 cm$^{-1}$
(3) 8-(2-Ethoxycarbonylamino-6-methylbenzyloxy)-2-methyl-3-(2-propynyl)imidazo[1,2-a]pyridine
IR (Nujol): 3280, 1710, 1540 cm$^{-1}$
(4) 8-(2-Methanesulfonylamino-6-methylbenzyloxy)-2-methyl-3-(2-propynyl)imidazo[1,2-a]pyridine
IR (Nujol): 3275, 1540, 1323, 1145 cm$^{-1}$
(5) 8-(3-Acetamido-2-methylbenzyloxy)-2-methyl-3-(2-propynyl)imidazo[1,2-a]pyridine
IR (Nujol): 3200, 1635, 1540 cm$^{-1}$
(6) 2-Methyl-8-[6-methyl-2-(3-methylureido)benzyloxy]-3-(2-propynyl)imidazo[1,2-a]pyridine
IR (Nujol): 3400, 3290, 1695, 1605 cm$^{-1}$
(7) 8-(2-Methoxycarbonylamino-6-methylbenzyloxy)-2-methyl-3-(2-propynyl)imidazo[1,2-a]pyridine
IR (Nujol): 3300, 1710, 1535, 1360, 1275, 1255 cm$^{-1}$
(8) 8-(5-Acetamido-2-methylbenzyloxy)-2-methyl-3-(2-propynyl)imidazo[1,2-a]pyridine
IR (Nujol): 3270, 1670, 1595, 1535, 1490 cm$^{-1}$
(9) 8-(2-t-Butoxycarbonylamino-6-methylbenzyloxy)-2-methyl-3-(2-propynyl)imidazo[1,2-a]pyridine
IR (CHCl$_3$): 3400, 3300, 1710, 1580, 1535, 1370, 1270, 1150 cm$^{-1}$
(10) 8-(2-Acetamido-6-methylbenzyloxy)-2-methyl-3-(2-propynyl)imidazo[1,2-a]pyridine
IR (Nujol): 3340, 3270, 1683, 1603, 1585, 1280 cm$^{-1}$
(11) 8-(2-Isonicotinamido-6-methylbenzyloxy)-2-methyl-3-(2-propynyl)imidazo[1,2-a]pyridine
IR (Nujol): 3375, 3245, 1680, 1600, 1540, 1520 cm$^{-1}$
(12) 2-Methyl-8-(2-methyl-6-propionamidobenzyloxy)-3-(2-propynyl)imidazo[1,2-a]pyridine IR (Nujol): 3310, 1690, 1600, 1585, 1540 cm⁻¹
(13) 8-(2-t-Butoxycarbonylaminoacetamido-6-methylbenzyloxy)-2-methyl-3-(2-propynyl)imidazo[1,2-a]pyridine
NMR (CDCl₃, δ): 1.30 (9H, s), 2.08 (1H, t, J=3 Hz), 2.47 (6H, s), 3.78 (2H, d, J=3 Hz), 4.03 (2H, d, J=6 Hz), 5.42 (2H, s), 6.70–7.40 (5H, m), 7.77–8.10 (2H, m), 9.67 (1H, broad s)
(14) 8-(2-Benzyloxycarbonylamino-6-methylbenzyloxy)-2-methyl-3-(2-propynyl)imidazo[1,2-a]pyridine
IR (Nujol): 3290, 1705, 1540 cm⁻¹
(15) 8-(2-Isopropoxycarbonylamino-6-methylbenzyloxy)-2-methyl-3-(2-propynyl)imidazo[1,2-a]pyridine
IR (Nujol): 3280, 1705, 1540 cm⁻¹
(16) 8-(4-Acetamido-2-methylbenzyloxy)-2-methyl-3-(2-propynyl)imidazo[1,2-a]pyridine
IR (Nujol): 3250, 1680, 1590, 1540 cm⁻¹
(17) 8-(2-Hydroxyacetamido-6-methylbenzyloxy)-2-methyl-3-(2-propynyl)imidazo[1,2-a]pyridine
IR (Nujol): 3320, 3190, 1680, 1520, 1280 cm⁻¹
(18) 8-(2-Acetoxyacetamido-6-methylbenzyloxy-2-methyl-3-(2-propynyl)imidazo[1,2-a]pyridine
IR (Nujol): 3390, 3275, 1740, 1685, 1600, 1525, 1270, 1220 cm⁻¹
(19) 8-(2-Lactamido-6-methylbenzyloxy)-2-methyl-3-(2-propynyl)imidazo[1,2-a]pyridine
IR (Nujol): 3320, 3270, 1675, 1540, 1275, 1080 cm⁻¹
(20) 8-(2-Aminoacetamido-6-methylbenzyloxy)-2-methyl-3-(2-propynyl)imidazo[1,2-a]pyridine
IR (Nujol): 3300, 3120, 1690, 1605, 1540, 1280 cm⁻¹
(21) 8-{2-(3-Benzoylthioureido)-6-methylbenzyloxy}-2-methyl-3-(2-propynyl)imidazo[1,2-a]pyridine
IR (Nujol): 3290, 3270, 1645, 1525, 1255
(22) 2-Methyl-8-(6-methyl-2-thioureidobenzyloxy)-3-(2-propynyl)imidazo[1,2-a]pyridine
IR (Nujol): 3460, 3340, 3300, 3150, 1600, 1545 cm⁻¹

EXAMPLE 29

The following compounds were prepared according to a similar manner to that of Example 21.
(1) 8-[2-(N-Methoxycarbonyl-N-methylamino)-6-methylbenzyloxy]-2-methyl-3-(2-propynyl)imidazo[1,2-a]pyridine
IR (Nujol): 3260, 1695, 1570, 1530, 1275 cm⁻¹
(2) 2-Methyl-8-[2-Methyl-6-(N-methyl-N-t-butoxycarbonylamino)benzyloxy]-3-(2-propynyl)imidazo[1,2-a]pyridine
IR (Film): 3300, 1690, 1542 cm⁻¹
(3) 2-Methyl-8-[2-methyl-6-(1-methylureido)benzyloxy]-3-(2-propynyl)imidazo[1,2-a]pyridine
IR (Nujol): 3475, 3280, 3180, 1655, 1580, 1540 cm⁻¹
(4) 2-Methyl-8-[2-methyl-6-(N-methyl-N-mesylamino)benzyloxy]-3-(2-propynyl)imidazo[1,2-a]pyridine
IR (Nujol): 3245, 1530, 1330, 1140 cm⁻¹

EXAMPLE 30

A mixture of 8-hydroxy-2-methyl-3-(2-propynyl)imidazo[1,2-a]pyridine (0.372 g) and potassium carbona (0.276 g) in N,N-dimethylformamide (7.4 ml) was stirred at room temperature for 20 minutes under a nitrogen atmosphere and then 2-methoxycarbonylamino-6-methylbenzylchloride (0.427 g) was added. After being stirred for 2 hours. The mixture was poured into water and the resulting precipitates were collected by filtration. The crude product was purified by column chromatography on silica gel (10 g) with chloroform as eluents to give 8-(2-methoxycarbonylamino-6-methylbenzyloxy)-2-methyl-3-(2-propynyl)imidazo[1,2-a]pyridine (0.048 g).

mp: 180° to 181° C. (recrystallized from a mixture of ethyl acetate and cyclohexane)
IR (Nujol): 3300, 1710, 1535, 1360, 1275, 1255 cm⁻¹
NMR (CDCl₃, δ): 2.06 (1H, t, J=3 Hz), 2.48 (6H, s), 3.73 (3H, s), 3.75 (2H, d, J=3 Hz), 5.35 (2H, s), 6.53–6.80 (2H, m), 6.90 (1H, d, J=7.5 Hz), 7.18 (1H, t, J=7.5 Hz), 7.50–7.80 (2H, m), 9.17 (1H, broad s)

EXAMPLE 31

8-(2-Methoxycarbonylamino-6-methylbenzyloxy)-2-methyl-3-(2-propynyl)imidazo[1,2-a]pyridine (Compound 1) prepared by Example 3, 28-(7) or 30 can be obtained as A-form and B-form according to the following methods.

(1) Compound 1 (50.0 g) was dissolved in ethanol (1,500 ml) under reflux and the hot solution was poured into water (1,500 ml). The precipitate formed was collected by filtration, washed with ethanol and dried under vacuum to give the crystals of A-form (47.4 g).
IR (Nujol): 3300, 1710, 1535, 1360, 1275, 1255 cm⁻¹
X-ray powedr diffraction: 2θ=8.8°
Similarly, the crystals of A-form could be obtained by recrystallization of Compound 1 from the following solvents:

Solvents ethyl acetate-cyclohexane, tetrahydrofuran-water, isopropyl-alcohol-water ethyl acetate-heptane (2) Compound 1 (50,0 g) was dissolved in ethyl acetate (850 ml) under reflux and cooled at 10 ° C. The precipitate formed was collected by filtration, washed with ethyl acetate, and dried under vacuum to give the crystals of B-form (43.2 g).
IR (Nujol): 3300, 1710, 1535, 1360, 1275, 1255, 1245 cm⁻¹
X-ray powder diffraction: 2θ=9.2°
Similarly, the crystals of B-form could be obtained by recrystallization of Compound 1 from the following solvents:

Solvents tetrahydrofuran, acetonitrile, methylene chloride, methyl ethyl ketone, methyl isobuthyl ketone, tetrahydrofuran-heptane, acetonitrile-heptane (3) Compound 1 (5.0 g) was dissolved in ethanol (75 ml) under reflux and allowed to stand. After an hour, the solution was cooled at 10° C. The precipitate formed was collected by filtration, washed with ethanol, and dried under vacuum to give the crystals of the mixture of A-form and B-form (4.62 g).

Similarly, the crystals of the mixture of A-form and B-form could be obtained by recrystallization of Compound 1 from the following solvent:

Solvent ethanol-cyclohexane

What we claim is:
1. An imidazopyridine compound of the formula:

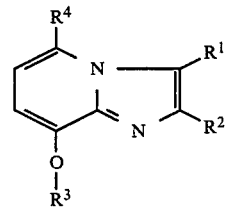

wherein

R¹ is lower alkynyl, lower alkynyloxy(lower)alkyl or N,N-di(lower)alkylamino(lower)alkynyl, R² is lower alkyl, R³ is mono (or di or tri)phenyl(lower)alkyl substituted by one or more substituent(s) selected from cyano, carbamoyl, mono (or di or tri)phenyl(lower)alkylamino, acylamino, carboxy, esterified carboxy, hydroxy, hydroxy(lower)alkyl, acyloxy(lower)alkyl, acyloxy, mono (or di or tri)-phenyl(lower)alkoxy, lower alkoxy(lower)alkoxy, tetrahydropyranyloxy, and acylamino(lower)alkyl or mono (or di or tri) phenyl (lower) alkyl substituted by lower alkyl and one additional substituent selected from hydroxy(lower)alkyl, amino, N-lower alkyl-N-acylamino, mono (or di or tri)phenyl(lower)alkylamino, acylamino and lower alkylamino, and R⁴ is hydrogen or lower alkyl, and a pharmaceutically acceptable salt thereof.

2. A compound of claim 1, wherein

R³ is mono (or di or tri)phenyl(lower)alkyl substituted by one or more substituent(s) selected from cyano, carbamoyl, acylamino, carboxy, esterified carboxy, hydroxy, hydroxy(lower)alkyl, acyloxy(lower)alkyl, lower alkoxy(lower)alkoxy and acylamino(lower)alkyl or mono (or di or tri)-phenyl(lower)alkyl substituted by lower alkyl and one additional substituent selected from hydroxy(lower)alkyl, amino, N-lower alkyl-N-acylamino, acylamino and lower alkylamino.

3. A compound of claim 2, wherein

R³ is mono (or di or tri)phenyl(lower)alkyl substituted by one or more substituent(s) selected from cyano, carbamoyl, lower alkanoylamino, lower alkoxycarbonylamino, ureido, carboxy, lower alkoxycarbonyl, hydroxy, hydroxy(lower)alkyl, lower alkanoyloxy(lower)alkyl, lower alkoxy(lower)alkoxy and lower alkoxycarbonylamino(lower)alkyl; or mono (or di or tri)phenyl(lower)alkyl substituted by lower alkyl and one additional substituent selected from hydroxy(lower)alkyl, amino, lower alkanoylamino, lower alkanesulfonylamino, lower alkoxycarbonylamino, isonicotinamido, ureido, ureido having lower alkyl, lower alkoxycarbonylamino(lower)alkanoylamino, phenyl(lower)alkoxycarbonylamino, N-lower alkoxycarbonyl-N-lower alkylamino, N-lower alkanoyl-N-lower alkylamino, N-carbamoyl-N-lower alkylamino, 1,3-di(lower)alkylureido, N-lower alkanesulfonyl-N-lower alkylamino, lower alkylamino, 3-aroylthioureido, thioureido, hydroxy(lower)alkanoylamino, lower alkanoyloxy(lower)alkanoylamino, lower alkanoylcarbonylamino, lower alkoxycarbonylcarbonylamino, sulfamido, lower alkanoylamino substituted by hydroxy and amino(lower)alkanoylamino.

4. A compound of claim 3, wherein

R³ is benzyl substituted by one or more substituent(s) selected from cyano, carbamoyl, lower alkanoylamino, lower alkoxycarbonylamino, ureido, carboxy, lower alkoxycarbonyl, hydroxy, hydroxy(lower)alkyl, lower alkanoyloxy(lower)alkyl, lower alkoxy(lower)alkoxy and lower alkoxycarbonylamino(lower)alkyl.

5. A compound of claim 4, wherein

R¹ is propynyl or propynyloxymethyl,

R² is methyl,

R³ is benzyl substituted by one or more substituent(s) selected from cyano, carbamoyl, formamido, acetamido, methoxycarbonylamino, ureido, carboxy, ethoxycarbonyl, hydroxy, hydroxymethyl, acetoxymethyl, methoxymethoxy and methoxycarbonylaminomethyl, and R⁴ is hydrogen.

6. A compound of claim 5, wherein

R¹ is 2-propynyl or 2-propynyloxymethyl,

R³ is 2-cyanobenzyl, 2-carbamoylbenzyl, 4-carbamoylbenzyl, 2-formamidobenzyl, 2-acetamidobenzyl, 2,6-bis(acetamido)benzyl, 2-methoxycarbonylaminobenzyl, 2-ureidobenzyl, 4-carboxybenzyl, 4-ethoxycarbonylbenzyl, 3-hydroxybenzyl, 2-hydroxymethylbenzyl, 4-hydroxymethylbenzyl, 2,6-bis(hydroxymethyl)benzyl, 2-acetoxymethylbenzyl, 2-methoxymethoxybenzyl and 2-methoxycarbonylaminomethylbenzyl.

7. A compound of claim 3, wherein

R³ is benzyl substituted by lower alkyl and one additional substituent selected from hydroxy(lower)alkyl, amino, lower alkanoylamino, lower alkanesulfonylamino, lower alkoxycarbonylamino, isonicotinamido, ureido, ureido having lower alkyl, lower alkoxycarbonylamino(lower)alkanoylamino, phenyl(lower)alkoxycarbonylamino, N-lower alkoxycarbonyl-N-lower alkylamino, N-lower alkanoyl-N-lower alkylamino, N-carbamoyl-N-lower alkylamino, 1,3-di(lower)alkylureido, N-lower alkanesulfonyl-N-lower alkylamino, lower alkylamino, 3-aroylthioureido, thioureido, hydroxy(lower)alkanoylamino, lower alkanoyloxy (lower) alkanoylamino, lower alkanoylcarbonylamino, lower alkoxycarbonylcarbonylamino, sulfamido, lower alkanoylamino substituted by hydroxy and amino(lower)alkanoylamino.

8. A compound of claim 7, wherein

R¹ is propynyl or N,N-dimethylaminobutynyl,

R² is methyl,

R³ is benzyl substituted by methyl and one additional substituent selected from hydroxymethyl, amino, formamido, acetamido, propionamido, n-butyramido, methanesulfonylamino, methoxycarbonylamino, ethoxycarbonylamino, iso-propoxycarbonylamino, tert-butoxyarbonylamino, isonicotinamido, ureido, methylureido, tert-butoxycarbonylaminoacetamido, benzyloxycarbonylamino, N-methoxycarbonyl-N-methylamino, N-tert-butoxycarbonyl-N-methylamino, N-acetyl-N-methylamino, N-carbamoyl-N-methylamino, 1,3-dimethylureido, N-mesyl-N-methylamino, methylamino,3-benzoylthioureido, thioureido, hydroxyacetamido, acetoxyacetamido, pyruvamido, methoxalylamino, sulfamido, lactamido and aminoacetamido, and R⁴ is hydrogen or methyl.

9. A compound of claim 8, wherein

R¹ is 2-propynyl or N,N-dimethylamino-2-butynyl,

R³ is 2-hydroxymethyl-6-methylbenzyl, 2-amino-6-methylbenzyl, 2-formamido-6-methylbenzyl, 2-acetamido-6-methylbenzyl, 3-acetamido-2-methylbenzyl, 4-acetamido-2-methylbenzyl, 5-acetamido-2-methylbenzyl, 2-methyl-6-propionamidobenzyl, 2-n-butyramido-6-methylbenzyl, 2-methanesulfonylamino-6-methylbenzyl, 2-methoxycarbonylamino-6-methylbenzyl, 2-ethoxycarbonylamino-6-methylbenzyl, 2-iso-propoxycarbonylamino-6-methylbenzyl, 2-methyl-6-tertbutoxycarbonylaminobenzyl, 2-isonicotinamido-6-methylbenzyl, 2-methyl-6-ureidobenzyl, 2-methyl-6-(3-methylureido)benzyl, 2-methyl-6-tert-butoxycarbonylaminoacetamidobenzyl, 2-benzyloxycarbonylamino-6-methylbenzyl, 2-(N-methoxycarbonyl-N-methylamino)-6-methylbenzyl, 2-methyl-6-(N-tert-butoxycarbonyl-N-methylamino)benzyl, 2-(N-acetyl-N-methylamino)-6-methylbenzyl, 2-(N-carbamoyl-N-methylamino)-6-methylbenzyl, 2-(1,3-dimethylureido)-6-methylbenzyl, 2-(N-mesyl-N-methylamino)-6-methylbenzyl, 2-methyl-6-methylaminobenzyl, 2-(3-benzoylthioureido)-6-methylbenzyl, 2-methyl-6-thioureidobenzyl, 2-hydroxyacetamido-6-methylbenzyl, 2-acetoxyacetamido-6-methylbenzyl, 2-methyl-6-pyruvamidobenzyl, 2-methoxalylamino-6-methylbenzyl, 2-methyl-6-sulfamidobenzyl, 2-lactamido-6-methylbenzyl, 2-aminoacetamido-6-methylbenzyl.

10. A compound of claim 9, which is 8-(2-methoxycarbonylamino-6-methylbenzyloxy)-2-methyl-3-(2-propynyl)imidazo[1,2-a]pyridine, its hydrochloride or its sulfate.

11. A compound of claim 9, which is 2-methyl-8-(2-methyl-6-thioureidobenzyloxy)-3-(2-propynyl)imidazo[1,2-a]pyrridine.

12. A pharmaceutical composition which comprises, as an active ingredient, an antiulcerative effective amount of a compound of claim 1 or a pharmaceutically acceptable salt thereof in admixture with pharmaceutically acceptable carriers.

13. A method for the treatment of ulcer which comprises administering an antiulcerative effective amount of a compound of claim 1 or a pharmaceutically acceptable salt thereof to human or animal.

* * * * *